(12) United States Patent
Bedi et al.

(10) Patent No.: US 8,348,129 B2
(45) Date of Patent: Jan. 8, 2013

(54) SURGICAL STAPLER HAVING A CLOSURE MECHANISM

(75) Inventors: James J. Bedi, Cincinnati, OH (US); John P. Measamer, Cincinnati, OH (US); Chester O. Baxter, III, Loveland, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 311 days.

(21) Appl. No.: 12/622,099

(22) Filed: Nov. 19, 2009

(65) Prior Publication Data

US 2011/0084115 A1    Apr. 14, 2011

Related U.S. Application Data

(60) Provisional application No. 61/250,377, filed on Oct. 9, 2009.

(51) Int. Cl.
*A61B 17/064* (2006.01)
(52) U.S. Cl. .................................... 227/179.1; 227/19
(58) Field of Classification Search ............... 227/175.1, 227/179.1, 19
See application file for complete search history.

(56) References Cited

U.S. PATENT DOCUMENTS

| | | | |
|---|---|---|---|
| 3,490,675 A | 1/1970 | Green et al. |
| 3,499,591 A | 3/1970 | Green |
| 3,551,987 A | 1/1971 | Wilkinson |
| 3,643,851 A | 2/1972 | Green et al. |
| 3,662,939 A | 5/1972 | Bryan |
| 3,717,294 A | 2/1973 | Green |
| 3,819,100 A | 6/1974 | Noiles et al. |
| 4,296,881 A | 10/1981 | Lee |
| 4,304,236 A | 12/1981 | Conta et al. |
| 4,331,277 A | 5/1982 | Green |
| 4,383,634 A | 5/1983 | Green |
| 4,396,139 A | 8/1983 | Hall et al. |
| 4,402,445 A | 9/1983 | Green |
| 4,415,112 A | 11/1983 | Green |
| 4,429,695 A | 2/1984 | Green |
| 4,475,679 A | 10/1984 | Fleury, Jr. |
| 4,489,875 A | 12/1984 | Crawford et al. |
| 4,500,024 A | 2/1985 | DiGiovanni et al. |
| 4,505,273 A | 3/1985 | Braun et al. |
| 4,505,414 A | 3/1985 | Filipi |

(Continued)

FOREIGN PATENT DOCUMENTS

CA    2458946 A1    3/2003

(Continued)

OTHER PUBLICATIONS

Disclosed Anonymously, "Motor-Driven Surgical Stapler Improvements," Research Disclosure Database No. 526041, Published: Feb. 2008.

(Continued)

*Primary Examiner* — Brian D Nash

(57) ABSTRACT

A surgical stapler comprising a first handle portion comprising a staple cartridge channel configured to receive a staple cartridge and a second handle portion comprising an anvil. The stapler further comprises a rotatable latch and a latch projection, wherein the latch is rotatably coupled to one of the first handle portion and the second handle portion and wherein the latch projection extends from the other of the first handle portion and the second handle portion. The latch is configured to engage the latch projection to move the first handle portion and the second handle portion toward one another. In various embodiments, the latch projection comprises a rotatable bearing wherein the latch is configured to contact the rotatable bearing when the latch engages the latch projection.

13 Claims, 49 Drawing Sheets

U.S. PATENT DOCUMENTS

| | | |
|---|---|---|
| 4,520,817 A | 6/1985 | Green |
| 4,522,327 A | 6/1985 | Korthoff et al. |
| 4,527,724 A | 7/1985 | Chow et al. |
| 4,530,453 A | 7/1985 | Green |
| 4,566,620 A | 1/1986 | Green et al. |
| 4,573,622 A | 3/1986 | Green et al. |
| 4,580,712 A | 4/1986 | Green |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,629,107 A | 12/1986 | Fedotov et al. |
| 4,632,290 A | 12/1986 | Green et al. |
| 4,633,874 A | 1/1987 | Chow et al. |
| 4,655,222 A | 4/1987 | Florez et al. |
| 4,664,305 A | 5/1987 | Blake, III et al. |
| 4,671,445 A | 6/1987 | Barker et al. |
| 4,715,520 A | 12/1987 | Roehr, Jr. et al. |
| 4,728,020 A | 3/1988 | Green et al. |
| 4,752,024 A | 6/1988 | Green et al. |
| 4,754,909 A | 7/1988 | Barker et al. |
| 4,767,044 A | 8/1988 | Green |
| 4,805,823 A | 2/1989 | Rothfuss |
| 4,809,695 A | 3/1989 | Gwathmey et al. |
| 4,817,847 A | 4/1989 | Redtenbacher et al. |
| 4,819,853 A | 4/1989 | Green |
| 4,821,939 A | 4/1989 | Green |
| 4,844,068 A | 7/1989 | Arata et al. |
| 4,869,414 A | 9/1989 | Green et al. |
| 4,869,415 A | 9/1989 | Fox |
| 4,892,244 A | 1/1990 | Fox et al. |
| 4,938,408 A | 7/1990 | Bedi et al. |
| 4,941,623 A | 7/1990 | Pruitt |
| 4,944,443 A | 7/1990 | Oddsen et al. |
| 4,978,049 A | 12/1990 | Green |
| 5,065,929 A | 11/1991 | Schulze et al. |
| 5,071,430 A | 12/1991 | de Salis et al. |
| 5,083,695 A | 1/1992 | Foslien et al. |
| 5,129,570 A | 7/1992 | Schulze et al. |
| 5,137,198 A | 8/1992 | Nobis et al. |
| 5,139,513 A | 8/1992 | Segato |
| 5,158,567 A | 10/1992 | Green |
| 5,173,133 A | 12/1992 | Morin et al. |
| 5,211,649 A | 5/1993 | Kohler et al. |
| 5,219,111 A | 6/1993 | Bilotti et al. |
| 5,221,036 A | 6/1993 | Takase |
| 5,222,975 A | 6/1993 | Crainich |
| 5,236,440 A | 8/1993 | Hlavacek |
| 5,258,009 A | 11/1993 | Conners |
| 5,263,629 A | 11/1993 | Trumbull et al. |
| 5,282,806 A | 2/1994 | Haber et al. |
| 5,282,829 A | 2/1994 | Hermes |
| 5,285,945 A | 2/1994 | Brinkerhoff et al. |
| 5,304,204 A | 4/1994 | Bregen |
| 5,342,395 A | 8/1994 | Jarrett et al. |
| 5,342,396 A | 8/1994 | Cook |
| 5,350,400 A | 9/1994 | Esposito et al. |
| 5,366,479 A | 11/1994 | McGarry et al. |
| 5,395,034 A | 3/1995 | Allen et al. |
| 5,397,324 A | 3/1995 | Carroll et al. |
| 5,405,072 A | 4/1995 | Zlock et al. |
| 5,413,272 A | 5/1995 | Green et al. |
| 5,417,361 A | 5/1995 | Williamson, IV |
| 5,425,745 A | 6/1995 | Green et al. |
| 5,445,304 A | 8/1995 | Plyley et al. |
| 5,447,265 A | 9/1995 | Vidal et al. |
| 5,465,895 A | 11/1995 | Knodel et al. |
| 5,474,566 A | 12/1995 | Alesi et al. |
| 5,478,354 A | 12/1995 | Tovey et al. |
| 5,480,089 A | 1/1996 | Blewett |
| 5,482,197 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,487,499 A | 1/1996 | Sorrentino et al. |
| 5,489,058 A | 2/1996 | Plyley et al. |
| 5,497,933 A | 3/1996 | DeFonzo et al. |
| 5,503,320 A | 4/1996 | Webster et al. |
| 5,505,363 A | 4/1996 | Green et al. |
| 5,509,596 A | 4/1996 | Green et al. |
| 5,520,700 A | 5/1996 | Beyar et al. |
| 5,529,235 A | 6/1996 | Boiarski et al. |
| 5,533,661 A | 7/1996 | Main et al. |
| 5,535,934 A | 7/1996 | Boiarski et al. |
| 5,535,935 A | 7/1996 | Vidal et al. |
| 5,540,375 A | 7/1996 | Bolanos et al. |
| 5,542,594 A | 8/1996 | McKean et al. |
| 5,547,117 A | 8/1996 | Hamblin et al. |
| 5,553,765 A | 9/1996 | Knodel et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,564,615 A | 10/1996 | Bishop et al. |
| 5,571,116 A | 11/1996 | Bolanos et al. |
| 5,575,799 A | 11/1996 | Bolanos et al. |
| 5,577,654 A | 11/1996 | Bishop |
| 5,580,067 A | 12/1996 | Hamblin et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,624,452 A | 4/1997 | Yates |
| 5,628,446 A | 5/1997 | Geiste et al. |
| 5,630,539 A | 5/1997 | Plyley et al. |
| 5,630,540 A | 5/1997 | Blewett |
| 5,632,432 A | 5/1997 | Schulze et al. |
| 5,634,584 A | 6/1997 | Okorocha et al. |
| 5,636,779 A | 6/1997 | Palmer |
| 5,636,780 A | 6/1997 | Green et al. |
| 5,639,008 A | 6/1997 | Gallagher et al. |
| 5,645,209 A | 7/1997 | Green et al. |
| 5,647,526 A | 7/1997 | Green et al. |
| 5,649,937 A | 7/1997 | Bito et al. |
| 5,651,491 A | 7/1997 | Heaton et al. |
| 5,653,373 A | 8/1997 | Green et al. |
| 5,653,374 A | 8/1997 | Young et al. |
| 5,655,698 A | 8/1997 | Yoon |
| 5,657,921 A | 8/1997 | Young et al. |
| 5,662,258 A | 9/1997 | Knodel et al. |
| 5,662,260 A | 9/1997 | Yoon |
| 5,667,527 A | 9/1997 | Cook |
| 5,669,544 A | 9/1997 | Schulze et al. |
| 5,669,918 A | 9/1997 | Balazs et al. |
| 5,673,840 A | 10/1997 | Schulze et al. |
| 5,673,841 A | 10/1997 | Schulze et al. |
| 5,673,842 A | 10/1997 | Bittner et al. |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,690,269 A | 11/1997 | Bolanos et al. |
| 5,692,668 A | 12/1997 | Schulze et al. |
| 5,697,543 A | 12/1997 | Burdorff |
| 5,702,408 A | 12/1997 | Wales et al. |
| 5,704,534 A | 1/1998 | Huitema et al. |
| 5,706,997 A | 1/1998 | Green et al. |
| 5,711,472 A | 1/1998 | Bryan |
| 5,715,987 A | 2/1998 | Kelley et al. |
| 5,715,988 A | 2/1998 | Palmer |
| 5,716,366 A | 2/1998 | Yates |
| 5,718,359 A | 2/1998 | Palmer et al. |
| 5,725,536 A | 3/1998 | Oberlin et al. |
| 5,725,554 A | 3/1998 | Simon et al. |
| 5,730,758 A | 3/1998 | Allgeyer |
| 5,732,871 A | 3/1998 | Clark et al. |
| 5,732,872 A | 3/1998 | Bolduc et al. |
| 5,735,445 A | 4/1998 | Vidal et al. |
| 5,743,456 A | 4/1998 | Jones et al. |

| | | |
|---|---|---|
| 5,752,644 A | 5/1998 | Bolanos et al. |
| 5,752,965 A | 5/1998 | Francis et al. |
| 5,758,814 A | 6/1998 | Gallagher et al. |
| 5,762,255 A | 6/1998 | Chrisman et al. |
| 5,762,256 A | 6/1998 | Mastri et al. |
| 5,779,130 A | 7/1998 | Alesi et al. |
| 5,779,131 A | 7/1998 | Knodel et al. |
| 5,779,132 A | 7/1998 | Knodel et al. |
| 5,782,397 A | 7/1998 | Koukline |
| 5,785,232 A | 7/1998 | Vidal et al. |
| 5,794,834 A | 8/1998 | Hamblin et al. |
| 5,797,536 A | 8/1998 | Smith et al. |
| 5,797,537 A | 8/1998 | Oberlin et al. |
| 5,797,538 A | 8/1998 | Heaton et al. |
| 5,820,009 A | 10/1998 | Melling et al. |
| 5,826,776 A | 10/1998 | Schulze et al. |
| 5,833,695 A | 11/1998 | Yoon |
| 5,836,503 A | 11/1998 | Ehrenfels et al. |
| 5,839,639 A | 11/1998 | Sauer et al. |
| 5,855,311 A | 1/1999 | Hamblin et al. |
| 5,855,583 A | 1/1999 | Wang et al. |
| 5,865,361 A | 2/1999 | Milliman et al. |
| 5,868,760 A | 2/1999 | McGuckin, Jr. |
| 5,871,135 A | 2/1999 | Williamson, IV et al. |
| 5,878,937 A | 3/1999 | Green et al. |
| 5,878,938 A | 3/1999 | Bittner et al. |
| 5,894,979 A | 4/1999 | Powell |
| 5,897,562 A | 4/1999 | Bolanos et al. |
| 5,901,895 A | 5/1999 | Heaton et al. |
| 5,908,427 A | 6/1999 | McKean et al. |
| 5,911,353 A | 6/1999 | Bolanos et al. |
| 5,919,198 A | 7/1999 | Graves, Jr. et al. |
| 5,941,442 A | 8/1999 | Geiste et al. |
| 5,954,259 A | 9/1999 | Viola et al. |
| 5,988,479 A | 11/1999 | Palmer |
| 6,010,054 A | 1/2000 | Johnson et al. |
| 6,032,849 A | 3/2000 | Mastri et al. |
| 6,045,560 A | 4/2000 | McKean et al. |
| 6,050,472 A | 4/2000 | Shibata |
| 6,079,606 A | 6/2000 | Milliman et al. |
| 6,083,242 A | 7/2000 | Cook |
| 6,086,600 A | 7/2000 | Kortenbach |
| 6,099,551 A | 8/2000 | Gabbay |
| 6,102,271 A | 8/2000 | Longo et al. |
| 6,109,500 A | 8/2000 | Alli et al. |
| 6,119,913 A | 9/2000 | Adams et al. |
| 6,126,058 A | 10/2000 | Adams et al. |
| 6,131,789 A | 10/2000 | Schulze et al. |
| 6,155,473 A | 12/2000 | Tompkins et al. |
| 6,171,330 B1 | 1/2001 | Benchetrit |
| 6,193,129 B1 | 2/2001 | Bittner et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,273,897 B1 | 8/2001 | Dalessandro et al. |
| 6,302,311 B1 | 10/2001 | Adams et al. |
| 6,315,184 B1 | 11/2001 | Whitman |
| 6,325,810 B1 | 12/2001 | Hamilton et al. |
| 6,330,965 B1 | 12/2001 | Milliman et al. |
| 6,387,113 B1 | 5/2002 | Hawkins et al. |
| RE37,814 E | 8/2002 | Allgeyer |
| 6,436,107 B1 | 8/2002 | Wang et al. |
| 6,443,973 B1 | 9/2002 | Whitman |
| 6,488,196 B1 | 12/2002 | Fenton, Jr. |
| 6,488,197 B1 | 12/2002 | Whitman |
| 6,491,201 B1 | 12/2002 | Whitman |
| 6,505,768 B2 | 1/2003 | Whitman |
| 6,517,565 B1 | 2/2003 | Whitman et al. |
| 6,517,566 B1 | 2/2003 | Hovland et al. |
| 6,578,751 B2 | 6/2003 | Hartwick |
| 6,588,643 B2 | 7/2003 | Bolduc et al. |
| 6,601,749 B2 | 8/2003 | Sullivan et al. |
| 6,616,686 B2 | 9/2003 | Coleman et al. |
| 6,619,529 B2 | 9/2003 | Green et al. |
| 6,629,630 B2 | 10/2003 | Adams |
| 6,629,988 B2 | 10/2003 | Weadock |
| 6,644,532 B2 | 11/2003 | Green et al. |
| 6,669,073 B2 | 12/2003 | Milliman et al. |
| 6,681,978 B2 | 1/2004 | Geiste et al. |
| 6,681,979 B2 | 1/2004 | Whitman |
| 6,695,199 B2 | 2/2004 | Whitman |
| 6,698,643 B2 | 3/2004 | Whitman |
| 6,716,233 B1 | 4/2004 | Whitman |
| 6,755,338 B2 | 6/2004 | Hahnen et al. |
| 6,769,594 B2 | 8/2004 | Orban, III |
| 6,773,438 B1 | 8/2004 | Knodel et al. |
| 6,786,382 B1 | 9/2004 | Hoffman |
| 6,805,273 B2 | 10/2004 | Bilotti et al. |
| 6,817,508 B1 | 11/2004 | Racenet et al. |
| 6,817,509 B2 | 11/2004 | Geiste et al. |
| 6,830,174 B2 | 12/2004 | Hillstead et al. |
| 6,843,403 B2 | 1/2005 | Whitman |
| RE38,708 E | 3/2005 | Bolanos et al. |
| 6,874,669 B2 | 4/2005 | Adams et al. |
| 6,877,647 B2 | 4/2005 | Green et al. |
| 6,905,057 B2 | 6/2005 | Swayze et al. |
| 6,939,358 B2 | 9/2005 | Palacios et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,964,363 B2 | 11/2005 | Wales et al. |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 6,997,931 B2 | 2/2006 | Sauer et al. |
| 7,000,818 B2 | 2/2006 | Shelton, IV et al. |
| 7,000,819 B2 | 2/2006 | Swayze et al. |
| 7,008,435 B2 | 3/2006 | Cummins |
| 7,032,798 B2 | 4/2006 | Whitman et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,730 B2 | 6/2006 | Ehrenfels et al. |
| 7,055,731 B2 | 6/2006 | Shelton, IV et al. |
| 7,056,330 B2 | 6/2006 | Gayton |
| 7,059,508 B2 | 6/2006 | Shelton, IV et al. |
| 7,070,083 B2 | 7/2006 | Jankowski |
| 7,077,856 B2 | 7/2006 | Whitman |
| 7,080,769 B2 | 7/2006 | Vresh et al. |
| 7,083,075 B2 | 8/2006 | Swayze et al. |
| 7,090,684 B2 | 8/2006 | McGuckin, Jr. et al. |
| 7,097,089 B2 | 8/2006 | Marczyk |
| 7,108,709 B2 | 9/2006 | Cummins |
| 7,111,769 B2 | 9/2006 | Wales et al. |
| 7,114,642 B2 | 10/2006 | Whitman |
| 7,118,582 B1 | 10/2006 | Wang et al. |
| 7,121,446 B2 | 10/2006 | Arad et al. |
| 7,128,253 B2 | 10/2006 | Mastri et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,147,138 B2 | 12/2006 | Shelton, IV |
| 7,156,863 B2 | 1/2007 | Sonnenschein et al. |
| 7,159,750 B2 | 1/2007 | Racenet et al. |
| 7,168,604 B2 | 1/2007 | Milliman et al. |
| 7,172,104 B2 | 2/2007 | Scirica et al. |
| 7,182,239 B1 | 2/2007 | Myers |
| 7,188,758 B2 | 3/2007 | Viola et al. |
| 7,210,609 B2 | 5/2007 | Leiboff et |
| 7,213,736 B2 | 5/2007 | Wales et al. |
| 7,220,272 B2 | 5/2007 | Weadock |
| 7,225,964 B2 | 6/2007 | Mastri et al. |
| 7,237,708 B1 | 7/2007 | Guy et al. |
| 7,238,195 B2 | 7/2007 | Viola |
| 7,246,734 B2 | 7/2007 | Shelton, IV |
| 7,258,262 B2 | 8/2007 | Mastri et al. |
| 7,278,562 B2 | 10/2007 | Mastri et al. |
| 7,278,563 B1 | 10/2007 | Green |
| 7,296,724 B2 | 11/2007 | Green et al. |
| 7,303,106 B2 | 12/2007 | Milliman et al. |
| 7,303,107 B2 | 12/2007 | Milliman et al. |

| Patent No. | Date | Inventor |
|---|---|---|
| 7,328,828 B2 | 2/2008 | Ortiz et al. |
| 7,328,829 B2 | 2/2008 | Arad et al. |
| 7,334,717 B2 | 2/2008 | Rethy et al. |
| 7,354,447 B2 | 4/2008 | Shelton, IV et al. |
| 7,364,060 B2 | 4/2008 | Milliman |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,398,907 B2 | 7/2008 | Racenet et al. |
| 7,398,908 B2 | 7/2008 | Holsten et al. |
| 7,404,508 B2 | 7/2008 | Smith et al. |
| 7,404,509 B2 | 7/2008 | Ortiz et al. |
| 7,407,075 B2 | 8/2008 | Holsten et al. |
| 7,407,078 B2 | 8/2008 | Shelton, IV et al. |
| 7,410,086 B2 | 8/2008 | Ortiz et al. |
| 7,416,101 B2 | 8/2008 | Shelton, IV et al. |
| 7,419,080 B2 | 9/2008 | Smith et al. |
| 7,422,136 B1 | 9/2008 | Marczyk |
| 7,422,139 B2 | 9/2008 | Shelton, IV et al. |
| 7,424,965 B2 | 9/2008 | Racenet et al. |
| 7,431,188 B1 | 10/2008 | Marczyk |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,455,208 B2 | 11/2008 | Wales et al. |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,481,347 B2 | 1/2009 | Roy |
| 7,481,349 B2 | 1/2009 | Holsten et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,546,940 B2 | 6/2009 | Milliman et al. |
| 7,549,564 B2 | 6/2009 | Boudreaux |
| 7,552,854 B2 | 6/2009 | Wixey et al. |
| 7,556,185 B2 | 7/2009 | Viola |
| 7,559,450 B2 | 7/2009 | Wales et al. |
| 7,559,452 B2 | 7/2009 | Wales et al. |
| 7,568,603 B2 | 8/2009 | Shelton, IV et al. |
| 7,568,604 B2 | 8/2009 | Ehrenfels et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,597,229 B2 | 10/2009 | Boudreaux et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,631,793 B2 | 12/2009 | Rethy et al. |
| 7,637,409 B2 | 12/2009 | Marczyk |
| 7,641,092 B2 | 1/2010 | Kruszynski et al. |
| 7,641,093 B2 | 1/2010 | Doll et al. |
| 7,644,848 B2 | 1/2010 | Swayze et al. |
| 7,658,311 B2 | 2/2010 | Boudreaux |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,699,204 B2 | 4/2010 | Viola |
| 7,721,930 B2 | 5/2010 | McKenna et al. |
| 7,721,931 B2 | 5/2010 | Shelton, IV et al. |
| 7,721,934 B2 | 5/2010 | Shelton, IV et al. |
| 7,721,936 B2 | 5/2010 | Shalton, IV et al. |
| 7,722,610 B2 | 5/2010 | Viola et al. |
| 7,726,537 B2 | 6/2010 | Olson et al. |
| 7,726,538 B2 | 6/2010 | Holsten et al. |
| 7,731,072 B2 | 6/2010 | Timm et al. |
| 7,735,703 B2 | 6/2010 | Morgan et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,780,054 B2 | 8/2010 | Wales |
| 7,784,662 B2 | 8/2010 | Wales et al. |
| 7,832,611 B2 | 11/2010 | Boyden et al. |
| 7,845,533 B2 | 12/2010 | Marczyk et al. |
| 7,845,534 B2 | 12/2010 | Viola et al. |
| 7,870,989 B2 | 1/2011 | Viola et al. |
| 7,909,221 B2 | 3/2011 | Viola et al. |
| 7,922,063 B2 | 4/2011 | Zemlok et al. |
| 7,938,307 B2 | 5/2011 | Bettuchi |
| 7,950,560 B2 | 5/2011 | Zemlok et al. |
| 7,959,050 B2 | 6/2011 | Smith et al. |
| 8,002,795 B2 | 8/2011 | Beetel |
| 8,123,103 B2 | 2/2012 | Milliman |
| 8,167,895 B2 | 5/2012 | D'Agostino et al. |
| 2002/0117534 A1 | 8/2002 | Green et al. |
| 2004/0006372 A1 | 1/2004 | Racenet et al. |
| 2004/0034369 A1 | 2/2004 | Sauer et al. |
| 2004/0093024 A1 | 5/2004 | Lousararian et al. |
| 2004/0094597 A1 | 5/2004 | Whitman et al. |
| 2004/0108357 A1 | 6/2004 | Milliman et al. |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0222268 A1 | 11/2004 | Bilotti et al. |
| 2004/0232201 A1 | 11/2004 | Wenchell et al. |
| 2004/0243151 A1 | 12/2004 | Demmy et al. |
| 2004/0254608 A1 | 12/2004 | Huitema et al. |
| 2004/0267310 A1 | 12/2004 | Racenet et al. |
| 2005/0059997 A1 | 3/2005 | Bauman et al. |
| 2005/0103819 A1 | 5/2005 | Racenet et al. |
| 2005/0119669 A1 | 6/2005 | Demmy |
| 2005/0125009 A1 | 6/2005 | Perry et al. |
| 2005/0143759 A1 | 6/2005 | Kelly |
| 2005/0184121 A1 | 8/2005 | Heinrich |
| 2005/0187576 A1 | 8/2005 | Whitman et al. |
| 2005/0189397 A1 | 9/2005 | Jankowski |
| 2005/0192628 A1 | 9/2005 | Viola |
| 2005/0216055 A1 | 9/2005 | Scirica et al. |
| 2005/0240222 A1 | 10/2005 | Shipp |
| 2005/0263563 A1 | 12/2005 | Racenet et al. |
| 2005/0274768 A1 | 12/2005 | Cummins et al. |
| 2006/0011699 A1 | 1/2006 | Olson et al. |
| 2006/0047307 A1 | 3/2006 | Ortiz et al. |
| 2006/0049229 A1 | 3/2006 | Milliman et al. |
| 2006/0052825 A1 | 3/2006 | Ransick et al. |
| 2006/0060630 A1 | 3/2006 | Shelton, IV et al. |
| 2006/0085033 A1 | 4/2006 | Criscuolo et al. |
| 2006/0100643 A1 | 5/2006 | Laufer et al. |
| 2006/0173470 A1 | 8/2006 | Oray et al. |
| 2006/0180634 A1 | 8/2006 | Shelton, IV et al. |
| 2006/0226196 A1 | 10/2006 | Hueil et al. |
| 2006/0235469 A1 | 10/2006 | Viola |
| 2006/0241692 A1 | 10/2006 | McGuckin, Jr. et al. |
| 2006/0273135 A1 | 12/2006 | Beetel |
| 2006/0278680 A1 | 12/2006 | Viola et al. |
| 2006/0278681 A1 | 12/2006 | Viola et al. |
| 2006/0289602 A1 | 12/2006 | Wales et al. |
| 2007/0023476 A1 | 2/2007 | Whitman et al. |
| 2007/0023477 A1 | 2/2007 | Whitman et al. |
| 2007/0073341 A1 | 3/2007 | Smith |
| 2007/0084897 A1 | 4/2007 | Shelton, IV et al. |
| 2007/0102472 A1 | 5/2007 | Shelton, IV |
| 2007/0102473 A1 | 5/2007 | Shelton, IV et al. |
| 2007/0106317 A1 | 5/2007 | Shelton, IV et al. |
| 2007/0114261 A1 | 5/2007 | Ortiz et al. |
| 2007/0170225 A1 | 7/2007 | Shelton, IV et al. |
| 2007/0175949 A1 | 8/2007 | Shelton, IV et al. |
| 2007/0175950 A1 | 8/2007 | Shelton, IV et al. |

| | | |
|---|---|---|
| 2007/0175951 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0175957 A1 | 8/2007 | Shelton, IV et al. |
| 2007/0175958 A1 | 8/2007 | Shelton, IV et al. |
| 2007/0175964 A1 | 8/2007 | Shelton, IV et al. |
| 2007/0179476 A1 | 8/2007 | Shelton, IV et al. |
| 2007/0194079 A1 | 8/2007 | Hueil et al. |
| 2007/0194081 A1 | 8/2007 | Hueil et al. |
| 2007/0194082 A1 | 8/2007 | Morgan et al. |
| 2007/0221700 A1 | 9/2007 | Ortiz et al. |
| 2007/0221701 A1 | 9/2007 | Ortiz et al. |
| 2007/0225562 A1 | 9/2007 | Spivey et al. |
| 2007/0246505 A1 | 10/2007 | Pace-Floridia et al. |
| 2007/0295780 A1 | 12/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0035701 A1 | 2/2008 | Racenet et al. |
| 2008/0041916 A1 | 2/2008 | Milliman et al. |
| 2008/0041917 A1 | 2/2008 | Racenet et al. |
| 2008/0078800 A1 | 4/2008 | Hess et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082115 A1 | 4/2008 | Morgan et al. |
| 2008/0082124 A1 | 4/2008 | Hess et al. |
| 2008/0082125 A1 | 4/2008 | Murray et al. |
| 2008/0082126 A1 | 4/2008 | Murray et al. |
| 2008/0140115 A1 | 6/2008 | Stopek |
| 2008/0167522 A1 | 7/2008 | Giordano et al. |
| 2008/0167644 A1 | 7/2008 | Shelton et al. |
| 2008/0167671 A1 | 7/2008 | Giordano et al. |
| 2008/0167672 A1 | 7/2008 | Giordano et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0197167 A1 | 8/2008 | Viola et al. |
| 2008/0210738 A1 | 9/2008 | Shelton et al. |
| 2008/0237296 A1 | 10/2008 | Boudreaux et al. |
| 2008/0251568 A1 | 10/2008 | Zemlok et al. |
| 2008/0283570 A1 | 11/2008 | Boyden et al. |
| 2008/0290134 A1 | 11/2008 | Bettuchi et al. |
| 2008/0296343 A1 | 12/2008 | Schall et al. |
| 2008/0296345 A1 | 12/2008 | Shelton, IV et al. |
| 2008/0296346 A1 | 12/2008 | Shelton, IV et al. |
| 2008/0296347 A1 | 12/2008 | Shelton, IV et al. |
| 2008/0300579 A1 | 12/2008 | Broehl et al. |
| 2008/0300580 A1 | 12/2008 | Shelton, IV et al. |
| 2008/0300613 A1 | 12/2008 | Shelton, IV et al. |
| 2008/0308602 A1 | 12/2008 | Timm et al. |
| 2008/0308603 A1 | 12/2008 | Shelton, IV et al. |
| 2008/0308608 A1 | 12/2008 | Prommersberger |
| 2008/0314955 A1 | 12/2008 | Boudreaux et al. |
| 2008/0314957 A1 | 12/2008 | Boudreaux |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001124 A1 | 1/2009 | Hess et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012556 A1 | 1/2009 | Boudreaux et al. |
| 2009/0057369 A1 | 3/2009 | Smith et al. |
| 2009/0076534 A1 | 3/2009 | Shelton, IV et al. |
| 2009/0090763 A1 | 4/2009 | Zemlok et al. |
| 2009/0108048 A1 | 4/2009 | Zemlok et al. |
| 2009/0114701 A1 | 5/2009 | Zemlok et al. |
| 2009/0149871 A9 | 6/2009 | Kagan et al. |
| 2009/0200355 A1 | 8/2009 | Baxter, III et al. |
| 2009/0206123 A1 | 8/2009 | Doll et al. |
| 2009/0206124 A1 | 8/2009 | Hall et al. |
| 2009/0206125 A1 | 8/2009 | Huitema et al. |
| 2009/0206126 A1 | 8/2009 | Huitema et al. |
| 2009/0206128 A1 | 8/2009 | Hueil et al. |
| 2009/0206129 A1 | 8/2009 | Doll et al. |
| 2009/0206130 A1 | 8/2009 | Hall et al. |
| 2009/0206131 A1 | 8/2009 | Weisenburgh, II et al. |
| 2009/0206132 A1 | 8/2009 | Hueil et al. |
| 2009/0206133 A1 | 8/2009 | Morgan et al. |
| 2009/0206134 A1 | 8/2009 | Swayze et al. |
| 2009/0206135 A1 | 8/2009 | Hall et al. |
| 2009/0206136 A1 | 8/2009 | Moore et al. |
| 2009/0206137 A1 | 8/2009 | Hall et al. |
| 2009/0206138 A1 | 8/2009 | Smith et al. |
| 2009/0206139 A1 | 8/2009 | Hall et al. |
| 2009/0206140 A1 | 8/2009 | Scheib et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0206144 A1 | 8/2009 | Doll et al. |
| 2009/0209946 A1 | 8/2009 | Swayze et al. |
| 2009/0209990 A1 | 8/2009 | Yates et al. |
| 2009/0218384 A1 | 9/2009 | Aranyi |
| 2009/0242610 A1 | 10/2009 | Shelton, IV et al. |
| 2009/0255974 A1 | 10/2009 | Viola |
| 2009/0255975 A1 | 10/2009 | Zemlok et al. |
| 2009/0255976 A1 | 10/2009 | Marczyk et al. |
| 2009/0255977 A1 | 10/2009 | Zemlok |
| 2009/0255978 A1 | 10/2009 | Viola et al. |
| 2009/0289096 A1 | 11/2009 | Shelton, IV et al. |
| 2009/0308907 A1 | 12/2009 | Nalagatla et al. |
| 2010/0001036 A1 | 1/2010 | Marczyk et al. |
| 2010/0023024 A1 | 1/2010 | Zeiner et al. |
| 2010/0032470 A1 | 2/2010 | Hess et al. |
| 2010/0065605 A1 | 3/2010 | Shelton, IV et al. |
| 2010/0065609 A1 | 3/2010 | Schwemberger |
| 2010/0069942 A1 | 3/2010 | Shelton, IV |
| 2010/0072251 A1 | 3/2010 | Baxter, III et al. |
| 2010/0072252 A1 | 3/2010 | Baxter, III et al. |
| 2010/0072253 A1 | 3/2010 | Baxter, III et al. |
| 2010/0072256 A1 | 3/2010 | Baxter, III et al. |
| 2010/0076474 A1 | 3/2010 | Yates et al. |
| 2010/0076475 A1 | 3/2010 | Yates et al. |
| 2010/0089970 A1 | 4/2010 | Smith et al. |
| 2010/0089972 A1 | 4/2010 | Marczyk |
| 2010/0089974 A1 | 4/2010 | Shelton, IV |
| 2010/0096435 A1 | 4/2010 | Fuchs et al. |
| 2010/0127042 A1 | 5/2010 | Shelton, IV |
| 2010/0133317 A1 | 6/2010 | Shelton, IV et al. |
| 2010/0133318 A1 | 6/2010 | Boudreaux |
| 2010/0179382 A1 | 7/2010 | Shelton, IV et al. |
| 2010/0181364 A1 | 7/2010 | Shelton, IV et al. |
| 2010/0193566 A1 | 8/2010 | Scheib et al. |
| 2010/0193567 A1 | 8/2010 | Scheib et al. |
| 2010/0193568 A1 | 8/2010 | Scheib et al. |
| 2010/0193569 A1 | 8/2010 | Yates et al. |
| 2010/0198220 A1 | 8/2010 | Boudreaux et al. |
| 2010/0200637 A1 | 8/2010 | Beetel |
| 2010/0213241 A1 | 8/2010 | Bedi |
| 2010/0222901 A1 | 9/2010 | Swayze et al. |
| 2010/0224669 A1 | 9/2010 | Shelton, IV et al. |
| 2010/0237132 A1 | 9/2010 | Measamer et al. |
| 2010/0243709 A1 | 9/2010 | Hess et al. |
| 2010/0264193 A1 | 10/2010 | Huang et al. |
| 2010/0264194 A1 | 10/2010 | Huang et al. |
| 2010/0276471 A1 | 11/2010 | Whitman |
| 2010/0294827 A1 | 11/2010 | Boyden et al. |
| 2010/0294829 A1 | 11/2010 | Giordano et al. |
| 2010/0301095 A1 | 12/2010 | Shelton, IV et al. |
| 2010/0301096 A1 | 12/2010 | Moore et al. |
| 2010/0305552 A1 | 12/2010 | Shelton, IV et al. |
| 2010/0308100 A1 | 12/2010 | Boudreaux |
| 2011/0006099 A1 | 1/2011 | Hall et al. |
| 2011/0006101 A1 | 1/2011 | Hall et al. |
| 2011/0006103 A1 | 1/2011 | Laurent et al. |
| 2011/0011914 A1 | 1/2011 | Baxter, III et al. |
| 2011/0011915 A1 | 1/2011 | Shelton, IV |
| 2011/0017801 A1 | 1/2011 | Zemlok et al. |
| 2011/0024477 A1 | 2/2011 | Hall et al. |

| | | | | | | |
|---|---|---|---|---|---|---|
| 2011/0024478 A1 | 2/2011 | Shelton, IV | | EP | 0523174 B1 | 6/1994 |
| 2011/0024479 A1 | 2/2011 | Swensgard et al. | | EP | 0600182 A2 | 6/1994 |
| 2011/0036887 A1 | 2/2011 | Zemlok et al. | | EP | 0310431 B1 | 11/1994 |
| 2011/0042441 A1 | 2/2011 | Shelton, IV et al. | | EP | 0375302 B1 | 11/1994 |
| 2011/0060363 A1 | 3/2011 | Hess et al. | | EP | 0376562 B1 | 11/1994 |
| 2011/0062212 A1 | 3/2011 | Shelton, IV et al. | | EP | 0630612 A1 | 12/1994 |
| 2011/0068145 A1 | 3/2011 | Bedi et al. | | EP | 0634144 A1 | 1/1995 |
| 2011/0068148 A1 | 3/2011 | Hall et al. | | EP | 0646356 A2 | 4/1995 |
| 2011/0084112 A1 | 4/2011 | Kostrzewski | | EP | 0646357 A1 | 4/1995 |
| 2011/0084113 A1 | 4/2011 | Bedi et al. | | EP | 0653189 A2 | 5/1995 |
| 2011/0087276 A1 | 4/2011 | Bedi et al. | | EP | 0669104 A1 | 8/1995 |
| 2011/0101065 A1 | 5/2011 | Milliman | | EP | 0511470 B1 | 10/1995 |
| 2011/0114697 A1 | 5/2011 | Baxter, III et al. | | EP | 0679367 A2 | 11/1995 |
| 2011/0114698 A1 | 5/2011 | Baxter, III et al. | | EP | 0392547 B1 | 12/1995 |
| 2011/0114699 A1 | 5/2011 | Baxter, III et al. | | EP | 0685204 A1 | 12/1995 |
| 2011/0114700 A1 | 5/2011 | Baxter, III et al. | | EP | 0364216 B1 | 1/1996 |
| 2011/0118761 A1 | 5/2011 | Baxter, III et al. | | EP | 0699418 A1 | 3/1996 |
| 2011/0121051 A1 | 5/2011 | Shelton, IV et al. | | EP | 0702937 A1 | 3/1996 |
| 2011/0121052 A1 | 5/2011 | Shelton, IV et al. | | EP | 0705571 A1 | 4/1996 |
| 2011/0125176 A1 | 5/2011 | Yates et al. | | EP | 0711611 A2 | 5/1996 |
| 2011/0125177 A1 | 5/2011 | Yates et al. | | EP | 0484677 B2 | 6/1996 |
| 2011/0132962 A1 | 6/2011 | Hall et al. | | EP | 0541987 B1 | 7/1996 |
| 2011/0132963 A1 | 6/2011 | Giordano et al. | | EP | 0667119 B1 | 7/1996 |
| 2011/0132964 A1 | 6/2011 | Weisenburgh, II et al. | | EP | 0708618 B1 | 3/1997 |
| 2011/0132965 A1 | 6/2011 | Moore et al. | | EP | 0770355 A1 | 5/1997 |
| 2011/0139852 A1 | 6/2011 | Zingman | | EP | 0503662 B1 | 6/1997 |
| 2011/0144430 A1 | 6/2011 | Spivey et al. | | EP | 0447121 B1 | 7/1997 |
| 2011/0147433 A1 | 6/2011 | Shelton, IV et al. | | EP | 0625077 B1 | 7/1997 |
| 2011/0147434 A1 | 6/2011 | Hueil et al. | | EP | 0633749 B1 | 8/1997 |
| 2011/0155780 A1 | 6/2011 | Boudreaux | | EP | 0710090 B1 | 8/1997 |
| 2011/0155781 A1 | 6/2011 | Swensgard et al. | | EP | 0578425 B1 | 9/1997 |
| 2011/0155785 A1 | 6/2011 | Laurent et al. | | EP | 0625335 B1 | 11/1997 |
| 2011/0155787 A1 | 6/2011 | Baxter, III et al. | | EP | 0552423 B1 | 1/1998 |
| 2011/0163147 A1 | 7/2011 | Laurent et al. | | EP | 0592244 B1 | 1/1998 |
| 2011/0174860 A1 | 7/2011 | Shelton, IV et al. | | EP | 0648476 B1 | 1/1998 |
| 2011/0174863 A1 | 7/2011 | Shelton, IV et al. | | EP | 0649290 B1 | 3/1998 |
| 2011/0192882 A1 | 8/2011 | Hess et al. | | EP | 0598618 B1 | 9/1998 |
| 2011/0226837 A1 | 9/2011 | Baxter, III et al. | | EP | 0676173 B1 | 9/1998 |
| 2011/0233258 A1 | 9/2011 | Boudreaux | | EP | 0678007 B1 | 9/1998 |
| 2012/0132450 A1 | 5/2012 | Timm et al. | | EP | 0603472 B1 | 11/1998 |
| 2012/0138660 A1 | 6/2012 | Shelton, IV | | EP | 0605351 B1 | 11/1998 |
| 2012/0160721 A1 | 6/2012 | Shelton, IV et al. | | EP | 0878169 A1 | 11/1998 |
| 2012/0175399 A1 | 7/2012 | Shelton et al. | | EP | 0879742 A1 | 11/1998 |
| 2012/0199630 A1 | 8/2012 | Shelton, IV et al. | | EP | 0695144 B1 | 12/1998 |
| 2012/0199631 A1 | 8/2012 | Shelton, IV et al. | | EP | 0722296 B1 | 12/1998 |
| 2012/0199632 A1 | 8/2012 | Spivey et al. | | EP | 0760230 B1 | 2/1999 |
| 2012/0199633 A1 | 8/2012 | Shelton, IV et al. | | EP | 0623316 B1 | 3/1999 |
| 2012/0203247 A1 | 8/2012 | Shelton, IV et al. | | EP | 0650701 B1 | 3/1999 |
| | | | | EP | 0537572 B1 | 6/1999 |
| FOREIGN PATENT DOCUMENTS | | | | EP | 0923907 A1 | 6/1999 |
| CA | 2512960 A1 | 1/2006 | | EP | 0843906 B1 | 3/2000 |
| CA | 2514274 A1 | 1/2006 | | EP | 0552050 B1 | 5/2000 |
| CN | 1915180 A | 2/2007 | | EP | 0833592 B1 | 5/2000 |
| CN | 101095621 A | 1/2008 | | EP | 0830094 B1 | 9/2000 |
| DE | 273689 C | 5/1914 | | EP | 1034747 A1 | 9/2000 |
| DE | 1775926 A | 1/1972 | | EP | 1034748 A1 | 9/2000 |
| DE | 3210466 A1 | 9/1983 | | EP | 0694290 B1 | 11/2000 |
| DE | 9412228 U | 9/1994 | | EP | 1050278 A1 | 11/2000 |
| DE | 19509116 A1 | 9/1996 | | EP | 1053719 A1 | 11/2000 |
| DE | 19924311 A1 | 11/2000 | | EP | 1053720 A1 | 11/2000 |
| DE | 69328576 T2 | 1/2001 | | EP | 1055399 A1 | 11/2000 |
| DE | 10052679 A1 | 5/2001 | | EP | 1055400 A1 | 11/2000 |
| DE | 20112837 U1 | 10/2001 | | EP | 1080694 A1 | 3/2001 |
| DE | 20121753 U1 | 4/2003 | | EP | 1090592 A1 | 4/2001 |
| DE | 10314072 A1 | 10/2004 | | EP | 1095627 A1 | 5/2001 |
| DE | 202007003114 U1 | 6/2007 | | EP | 1256318 B1 | 5/2001 |
| EP | 0122046 A1 | 10/1984 | | EP | 0806914 B1 | 9/2001 |
| EP | 0070230 B1 | 10/1985 | | EP | 0768840 B1 | 12/2001 |
| EP | 0387980 B1 | 10/1985 | | EP | 0908152 B1 | 1/2002 |
| EP | 0033548 B1 | 5/1986 | | EP | 0872213 B1 | 5/2002 |
| EP | 0276104 A2 | 7/1988 | | EP | 0862386 B1 | 6/2002 |
| EP | 0248844 B1 | 1/1993 | | EP | 0949886 B1 | 9/2002 |
| EP | 0545029 A1 | 6/1993 | | EP | 1238634 A2 | 9/2002 |
| EP | 0277959 B1 | 10/1993 | | EP | 0858295 B1 | 12/2002 |
| EP | 0233940 B1 | 11/1993 | | EP | 0656188 B1 | 1/2003 |
| EP | 0261230 B1 | 11/1993 | | EP | 1284120 A1 | 2/2003 |
| EP | 0639349 A2 | 2/1994 | | EP | 1287788 A1 | 3/2003 |
| EP | 0324636 B1 | 3/1994 | | EP | 0717966 B1 | 4/2003 |
| EP | 0593920 A1 | 4/1994 | | EP | 0869742 B1 | 5/2003 |

| | | | | | | |
|---|---|---|---|---|---|---|
| EP | 0829235 | 61 | 6/2003 | EP | 1790293 A2 | 5/2007 |
| EP | 0887046 | B1 | 7/2003 | EP | 1800610 A1 | 6/2007 |
| EP | 0852480 | B1 | 8/2003 | EP | 1300117 B1 | 8/2007 |
| EP | 0891154 | B1 | 9/2003 | EP | 1813199 A1 | 8/2007 |
| EP | 0813843 | B1 | 10/2003 | EP | 1813201 A1 | 8/2007 |
| EP | 0873089 | B1 | 10/2003 | EP | 1813203 A2 | 8/2007 |
| EP | 0856326 | B1 | 11/2003 | EP | 1813207 A1 | 8/2007 |
| EP | 1374788 | A1 | 1/2004 | EP | 1813209 A1 | 8/2007 |
| EP | 0741996 | B1 | 2/2004 | EP | 1487359 B1 | 10/2007 |
| EP | 0814712 | B1 | 2/2004 | EP | 1599146 B1 | 10/2007 |
| EP | 1402837 | A1 | 3/2004 | EP | 1839596 A1 | 10/2007 |
| EP | 0705570 | B1 | 4/2004 | EP | 1402821 B1 | 12/2007 |
| EP | 0959784 | B1 | 4/2004 | EP | 1872727 A1 | 1/2008 |
| EP | 1407719 | A2 | 4/2004 | EP | 1897502 A1 | 3/2008 |
| EP | 1086713 | B1 | 5/2004 | EP | 1330201 B1 | 6/2008 |
| EP | 0996378 | B1 | 6/2004 | EP | 1702568 B1 | 7/2008 |
| EP | 1426012 | A1 | 6/2004 | EP | 1943976 A2 | 7/2008 |
| EP | 0833593 | B2 | 7/2004 | EP | 1593337 B1 | 8/2008 |
| EP | 1442694 | A1 | 8/2004 | EP | 1970014 A1 | 9/2008 |
| EP | 0888749 | B1 | 9/2004 | EP | 1980213 A2 | 10/2008 |
| EP | 0959786 | B1 | 9/2004 | EP | 1759645 B1 | 11/2008 |
| EP | 1459695 | A1 | 9/2004 | EP | 1693008 B1 | 12/2008 |
| EP | 1473819 | A1 | 11/2004 | EP | 1759640 B1 | 12/2008 |
| EP | 1477119 | A1 | 11/2004 | EP | 2000102 A2 | 12/2008 |
| EP | 1479345 | A1 | 11/2004 | EP | 1749486 B1 | 3/2009 |
| EP | 1479347 | A1 | 11/2004 | EP | 1721576 B1 | 4/2009 |
| EP | 1479348 | A1 | 11/2004 | EP | 1550413 B1 | 6/2009 |
| EP | 0754437 | B2 | 12/2004 | EP | 1745748 B1 | 8/2009 |
| EP | 1025807 | B1 | 12/2004 | EP | 2090256 A2 | 8/2009 |
| EP | 1001710 | B1 | 1/2005 | EP | 1607050 B1 | 12/2009 |
| EP | 1520521 | A1 | 4/2005 | EP | 1566150 B1 | 4/2010 |
| EP | 1520523 | A1 | 4/2005 | EP | 1813206 B1 | 4/2010 |
| EP | 1520525 | A1 | 4/2005 | EP | 1769754 B1 | 6/2010 |
| EP | 1522264 | A1 | 4/2005 | EP | 1535565 B1 | 10/2010 |
| EP | 1523942 | A2 | 4/2005 | EP | 1702570 B1 | 10/2010 |
| EP | 1550408 | A1 | 7/2005 | FR | 999646 A | 2/1952 |
| EP | 1557129 | A1 | 7/2005 | FR | 1112936 A | 3/1956 |
| EP | 1064883 | B1 | 8/2005 | FR | 2765794 A | 1/1999 |
| EP | 1067876 | B1 | 8/2005 | GB | 939929 A | 10/1963 |
| EP | 0870473 | B1 | 9/2005 | GB | 1210522 A | 10/1970 |
| EP | 1157666 | B1 | 9/2005 | GB | 1217159 A | 12/1970 |
| EP | 0880338 | B1 | 10/2005 | GB | 1339394 A | 12/1973 |
| EP | 1158917 | B1 | 11/2005 | GB | 2109241 A | 6/1983 |
| EP | 1344498 | B1 | 11/2005 | GB | 2272159 A | 5/1994 |
| EP | 1330989 | B1 | 12/2005 | GB | 2284242 A | 5/1995 |
| EP | 0771176 | B2 | 1/2006 | GB | 2336214 A | 10/1999 |
| EP | 1621138 | A2 | 2/2006 | GB | 2425903 A | 11/2006 |
| EP | 1621139 | A2 | 2/2006 | JP | 58500053 | 1/1983 |
| EP | 1621141 | A2 | 2/2006 | JP | 61-98249 | 5/1986 |
| EP | 1621145 | A2 | 2/2006 | JP | 3-12126 A | 1/1991 |
| EP | 1621151 | A2 | 2/2006 | JP | 5-212039 A | 8/1993 |
| EP | 1034746 | B1 | 3/2006 | JP | 6007357 A | 1/1994 |
| EP | 1632191 | A2 | 3/2006 | JP | 7051273 A | 2/1995 |
| EP | 1065981 | B1 | 5/2006 | JP | 8033641 A | 2/1996 |
| EP | 1082944 | B1 | 5/2006 | JP | 8229050 A | 9/1996 |
| EP | 1652481 | A2 | 5/2006 | JP | 2000033071 A | 2/2000 |
| EP | 1382303 | B1 | 6/2006 | JP | 2000171730 A | 6/2000 |
| EP | 1253866 | B1 | 7/2006 | JP | 2000287987 A | 10/2000 |
| EP | 1032318 | B1 | 8/2006 | JP | 2000325303 A | 11/2000 |
| EP | 1045672 | B1 | 8/2006 | JP | 2001-514541 A | 9/2001 |
| EP | 1617768 | B1 | 8/2006 | JP | 2001286477 A | 10/2001 |
| EP | 1693015 | A2 | 8/2006 | JP | 2002143078 A | 5/2002 |
| EP | 1400214 | B1 | 9/2006 | JP | 2002369820 A | 12/2002 |
| EP | 1702567 | A2 | 9/2006 | JP | 2004-344663 | 12/2004 |
| EP | 1129665 | B1 | 11/2006 | JP | 2005505322 T | 2/2005 |
| EP | 1400206 | B1 | 11/2006 | JP | 2005103293 A | 4/2005 |
| EP | 1256317 | B1 | 12/2006 | JP | 2005131163 A | 5/2005 |
| EP | 1285633 | B1 | 12/2006 | JP | 2005131164 A | 5/2005 |
| EP | 1728473 | A1 | 12/2006 | JP | 2005131173 A | 5/2005 |
| EP | 1728475 | A2 | 12/2006 | JP | 2005131211 A | 5/2005 |
| EP | 1479346 | B1 | 1/2007 | JP | 2005131212 A | 5/2005 |
| EP | 1484024 | B1 | 1/2007 | JP | 2005137423 A | 6/2005 |
| EP | 1754445 | A2 | 2/2007 | JP | 2005152416 A | 6/2005 |
| EP | 1759812 | A1 | 3/2007 | JP | 2005-523105 A | 8/2005 |
| EP | 1767163 | A1 | 3/2007 | JP | 2006-281405 A | 10/2006 |
| EP | 1769756 | A1 | 4/2007 | RU | 2187249 C2 | 8/2002 |
| EP | 1769758 | A1 | 4/2007 | RU | 2225170 C2 | 3/2004 |
| EP | 1581128 | B1 | 5/2007 | SU | 189517 A | 1/1967 |
| EP | 1785097 | A2 | 5/2007 | SU | 328636 A | 9/1972 |

| | | | | | | |
|---|---|---|---|---|---|---|
| SU | 886900 | A1 | 12/1981 | WO | WO 99/29244 A1 | 6/1999 |
| SU | 1333319 | A2 | 8/1987 | WO | WO 99/34744 A1 | 7/1999 |
| SU | 1377053 | A1 | 2/1988 | WO | WO 99/45849 A1 | 9/1999 |
| SU | 1561964 | A1 | 5/1990 | WO | WO 99/48430 A1 | 9/1999 |
| SU | 1722476 | A1 | 3/1992 | WO | WO 99/51158 A1 | 10/1999 |
| WO | WO 82/02824 | A1 | 9/1982 | WO | WO 00/24322 A1 | 5/2000 |
| WO | WO 91/15157 | A1 | 10/1991 | WO | WO 00/24330 A1 | 5/2000 |
| WO | WO 92/21300 | A1 | 12/1992 | WO | WO 00/41638 A1 | 7/2000 |
| WO | WO 93/08755 | A1 | 5/1993 | WO | WO 00/48506 A1 | 8/2000 |
| WO | WO 93/13718 | A1 | 7/1993 | WO | WO 00/53112 A2 | 9/2000 |
| WO | WO 93/14690 | A1 | 8/1993 | WO | WO 00/54653 A1 | 9/2000 |
| WO | WO 93/15850 | A1 | 8/1993 | WO | WO 00/57796 A1 | 10/2000 |
| WO | WO 93/19681 | A1 | 10/1993 | WO | WO 00/64365 A1 | 11/2000 |
| WO | WO 94/00060 | A1 | 1/1994 | WO | WO 00/72762 A1 | 12/2000 |
| WO | WO 94/11057 | A1 | 5/1994 | WO | WO 00/72765 A1 | 12/2000 |
| WO | WO 94/12108 | A1 | 6/1994 | WO | WO 01/03587 A1 | 1/2001 |
| WO | WO 94/18893 | A1 | 9/1994 | WO | WO 01/05702 A1 | 1/2001 |
| WO | WO 94/22378 | A1 | 10/1994 | WO | WO 01/10482 A1 | 2/2001 |
| WO | WO 94/23659 | A1 | 10/1994 | WO | WO 01/35845 A1 | 5/2001 |
| WO | WO 95/02369 | A1 | 1/1995 | WO | WO 01/54594 A1 | 8/2001 |
| WO | WO 95/03743 | A1 | 2/1995 | WO | WO 01/58371 A1 | 8/2001 |
| WO | WO 95/06817 | A1 | 3/1995 | WO | WO 01/62158 A2 | 8/2001 |
| WO | WO 95/09576 | A1 | 4/1995 | WO | WO 01/62161 A1 | 8/2001 |
| WO | WO 95/09577 | A1 | 4/1995 | WO | WO 01/62162 A1 | 8/2001 |
| WO | WO 95/14436 | A1 | 6/1995 | WO | WO 01/62164 A1 | 8/2001 |
| WO | WO 95/17855 | A1 | 7/1995 | WO | WO 01/62169 A2 | 8/2001 |
| WO | WO 95/18383 | A1 | 7/1995 | WO | WO 01/78605 A2 | 10/2001 |
| WO | WO 95/18572 | A1 | 7/1995 | WO | WO 01/91646 A1 | 12/2001 |
| WO | WO 95/19739 | A1 | 7/1995 | WO | WO 02/07608 A2 | 1/2002 |
| WO | WO 95/20360 | A1 | 8/1995 | WO | WO 02/07618 A1 | 1/2002 |
| WO | WO 95/23557 | A1 | 9/1995 | WO | WO 02/17799 A1 | 3/2002 |
| WO | WO 95/24865 | A1 | 9/1995 | WO | WO 02/19920 A1 | 3/2002 |
| WO | WO 95/25471 | A3 | 9/1995 | WO | WO 02/19932 A1 | 3/2002 |
| WO | WO 95/26562 | A2 | 10/1995 | WO | WO 02/30297 A2 | 4/2002 |
| WO | WO 95/29639 | A1 | 11/1995 | WO | WO 02/32322 A2 | 4/2002 |
| WO | WO 96/04858 | A1 | 2/1996 | WO | WO 02/36028 A1 | 5/2002 |
| WO | WO 96/19151 | A1 | 6/1996 | WO | WO 02/43571 A2 | 6/2002 |
| WO | WO 96/19152 | A1 | 6/1996 | WO | WO 02/058568 A1 | 8/2002 |
| WO | WO 96/20652 | A1 | 7/1996 | WO | WO 02/060328 A1 | 8/2002 |
| WO | WO 96/21119 | A1 | 7/1996 | WO | WO 02/067785 A2 | 9/2002 |
| WO | WO 96/22055 | A1 | 7/1996 | WO | WO 02/098302 A1 | 12/2002 |
| WO | WO 96/23448 | A1 | 8/1996 | WO | WO 03/000138 A2 | 1/2003 |
| WO | WO 96/24301 | A1 | 8/1996 | WO | WO 03/001329 A2 | 1/2003 |
| WO | WO 96/27337 | A1 | 9/1996 | WO | WO 03/013363 A1 | 2/2003 |
| WO | WO 96/35464 | A1 | 11/1996 | WO | WO 03/015604 A2 | 2/2003 |
| WO | WO 96/39085 | A1 | 12/1996 | WO | WO 03/020106 A2 | 3/2003 |
| WO | WO 96/39086 | A1 | 12/1996 | WO | WO 03/020139 A2 | 3/2003 |
| WO | WO 96/39087 | A1 | 12/1996 | WO | WO 03/024339 A1 | 3/2003 |
| WO | WO 96/39088 | A1 | 12/1996 | WO | WO 03/079909 A3 | 3/2003 |
| WO | WO 96/39089 | A1 | 12/1996 | WO | WO 03/030743 A2 | 4/2003 |
| WO | WO 97/00646 | A1 | 1/1997 | WO | WO 03/037193 A1 | 5/2003 |
| WO | WO 97/00647 | A1 | 1/1997 | WO | WO 03/047436 A3 | 6/2003 |
| WO | WO 97/06582 | A1 | 2/1997 | WO | WO 03/055402 A1 | 7/2003 |
| WO | WO 97/10763 | A1 | 3/1997 | WO | WO 03/057048 A1 | 7/2003 |
| WO | WO 97/10764 | A1 | 3/1997 | WO | WO 03/057058 A1 | 7/2003 |
| WO | WO 97/11648 | A2 | 4/1997 | WO | WO 03/063694 A1 | 8/2003 |
| WO | WO 97/11649 | A1 | 4/1997 | WO | WO 03/077769 A1 | 9/2003 |
| WO | WO 97/15237 | A1 | 5/1997 | WO | WO 03/079911 A1 | 10/2003 |
| WO | WO 97/24073 | A1 | 7/1997 | WO | WO 03/082126 A1 | 10/2003 |
| WO | WO 97/24993 | A1 | 7/1997 | WO | WO 03/088845 A2 | 10/2003 |
| WO | WO 97/30644 | A1 | 8/1997 | WO | WO 03/090630 A2 | 11/2003 |
| WO | WO 97/34533 | A1 | 9/1997 | WO | WO 03/094743 A1 | 11/2003 |
| WO | WO 97/37598 | A1 | 10/1997 | WO | WO 03/094745 A1 | 11/2003 |
| WO | WO 97/39688 | A2 | 10/1997 | WO | WO 03/094746 A1 | 11/2003 |
| WO | WO 98/17180 | A1 | 4/1998 | WO | WO 03/094747 A1 | 11/2003 |
| WO | WO 98/27880 | A1 | 7/1998 | WO | WO 03/101313 A1 | 12/2003 |
| WO | WO 98/30153 | A1 | 7/1998 | WO | WO 03/105698 A1 | 12/2003 |
| WO | WO 98/47436 | A1 | 10/1998 | WO | WO 03/105702 A2 | 12/2003 |
| WO | WO 99/03407 | A1 | 1/1999 | WO | WO 2004/006980 A2 | 1/2004 |
| WO | WO 99/03408 | A1 | 1/1999 | WO | WO 2004/011037 A2 | 2/2004 |
| WO | WO 99/03409 | A1 | 1/1999 | WO | WO 2004/019769 A1 | 3/2004 |
| WO | WO 99/12483 | A1 | 3/1999 | WO | WO 2004/021868 A2 | 3/2004 |
| WO | WO 99/12487 | A1 | 3/1999 | WO | WO 2004/028585 A2 | 4/2004 |
| WO | WO 99/12488 | A1 | 3/1999 | WO | WO 2004/032754 A2 | 4/2004 |
| WO | WO 99/15086 | A1 | 4/1999 | WO | WO 2004/032760 A2 | 4/2004 |
| WO | WO 99/15091 | A1 | 4/1999 | WO | WO 2004/032762 A1 | 4/2004 |
| WO | WO 99/23933 | A2 | 5/1999 | WO | WO 2004/032763 A2 | 4/2004 |
| WO | WO 99/23959 | A1 | 5/1999 | WO | WO 2004/034875 A2 | 4/2004 |
| WO | WO 99/25261 | A1 | 5/1999 | WO | WO 2004/047626 A1 | 6/2004 |

| | | |
|---|---|---|
| WO | WO 2004/047653 A2 | 6/2004 |
| WO | WO 2004/049956 A2 | 6/2004 |
| WO | WO 2004/052426 A2 | 6/2004 |
| WO | WO 2004/056276 A1 | 7/2004 |
| WO | WO 2004/056277 A1 | 7/2004 |
| WO | WO 2004/062516 A1 | 7/2004 |
| WO | WO 2004/078050 A2 | 9/2004 |
| WO | WO 2004/078051 A2 | 9/2004 |
| WO | WO 2004/086987 A1 | 10/2004 |
| WO | WO 2004/096015 A2 | 11/2004 |
| WO | WO 2004/096057 A2 | 11/2004 |
| WO | WO 2004/103157 A2 | 12/2004 |
| WO | WO 2004/105593 A1 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/044078 A2 | 5/2005 |
| WO | WO 2005/055846 A1 | 6/2005 |
| WO | WO 2005/072634 A2 | 8/2005 |
| WO | WO 2005/078892 A1 | 8/2005 |
| WO | WO 2005/079675 A2 | 9/2005 |
| WO | WO 2005/096954 A2 | 10/2005 |
| WO | WO 2005/112806 A2 | 12/2005 |
| WO | WO 2005/112808 A1 | 12/2005 |
| WO | WO 2005/115251 A2 | 12/2005 |
| WO | WO 2005/117735 A1 | 12/2005 |
| WO | WO 2005/122936 A1 | 12/2005 |
| WO | WO 2006/044490 A2 | 4/2006 |
| WO | WO 2006/044581 A2 | 4/2006 |
| WO | WO 2006/044810 A2 | 4/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/092563 A1 | 9/2006 |
| WO | WO 2006/092565 A1 | 9/2006 |
| WO | WO 2006/115958 A1 | 11/2006 |
| WO | WO 2006/125940 A1 | 11/2006 |
| WO | WO 2006/132992 A1 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/098220 A2 | 8/2007 |
| WO | WO 2007/121579 A1 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2007/147439 A1 | 12/2007 |
| WO | WO 2008/021969 A2 | 2/2008 |
| WO | WO 2008/039270 A1 | 4/2008 |
| WO | WO 2008/045383 A2 | 4/2008 |
| WO | WO 2008/109125 A1 | 9/2008 |
| WO | WO 2010/063795 A1 | 6/2010 |

OTHER PUBLICATIONS

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

The Sodem Aseptic Battery Transfer Kit, Sodem Systems, 2000, 3 pages.

"Biomedical Coatings," Fort Wayne Metals, Research Products Corporation, obtained online at www.fwmetals.com on Jun. 21, 2010 (1 page).

U.S. Appl. No. 12/030,424, filed Feb. 13, 2008.

U.S. Appl. No. 12/622,113, filed Nov. 19, 2009.

U.S. Appl. No. 12/622,130, filed Nov. 19, 2009.

International Search Report for PCT/US2010/051279, dated Jan. 19, 2011 (4 pages).

International Search Report for PCT/US2010/051288, dated Apr. 5, 2011 (6 pages).

Van Meer et al., "A Disposble Plastic Compact Wrist for Smart Minimally Invasive Surgical Tools," LAAS/CNRS (Aug. 2005).

Breedveld et al., "A New, Easily Miniaturized Sterrable Endoscope," IEEE Engineering in Medicine and Biology Magazine (Nov./Dec. 2005).

D. Tuite, Ed., "Get The Lowdown On Ultracapacitors," Nov. 15, 2007; [online] URL: http://electronicdesign.com/Articles/Print.cfm?ArticleID=17465, accessed Jan. 15, 2008 (5 pagese).

Datasheet for Panasonic TK Relays Ultra Low Profile 2 A Polarized Relay, Copyright Matsushita Electric Works, Ltd. (Known of at least as early as Aug. 17, 2010), 5 pages.

U.S. Appl. No. 13/040,604, filed Mar. 4, 2011.

International Search Report for PCT/US2010/051301, dated Apr. 6, 2011 (7 pages).

ASTM procedure D2240-00, "Standard Test Method for Rubber Property-Durometer Hardness," (Published Aug. 2000).

ASTM procedure D2240-05, "Standard Test Method for Rubber Property-Durometer Hardness," (Published Apr. 2010).

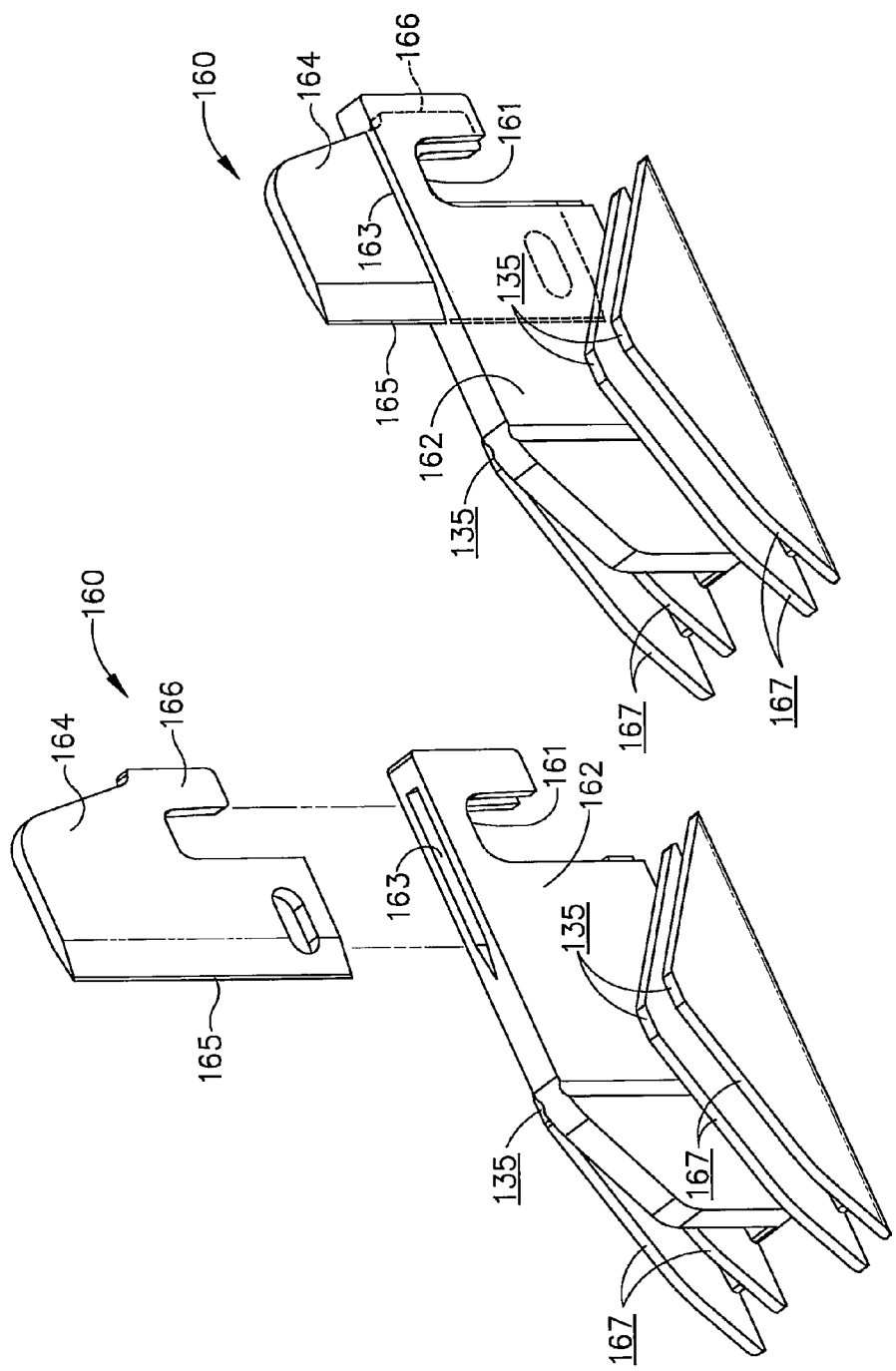

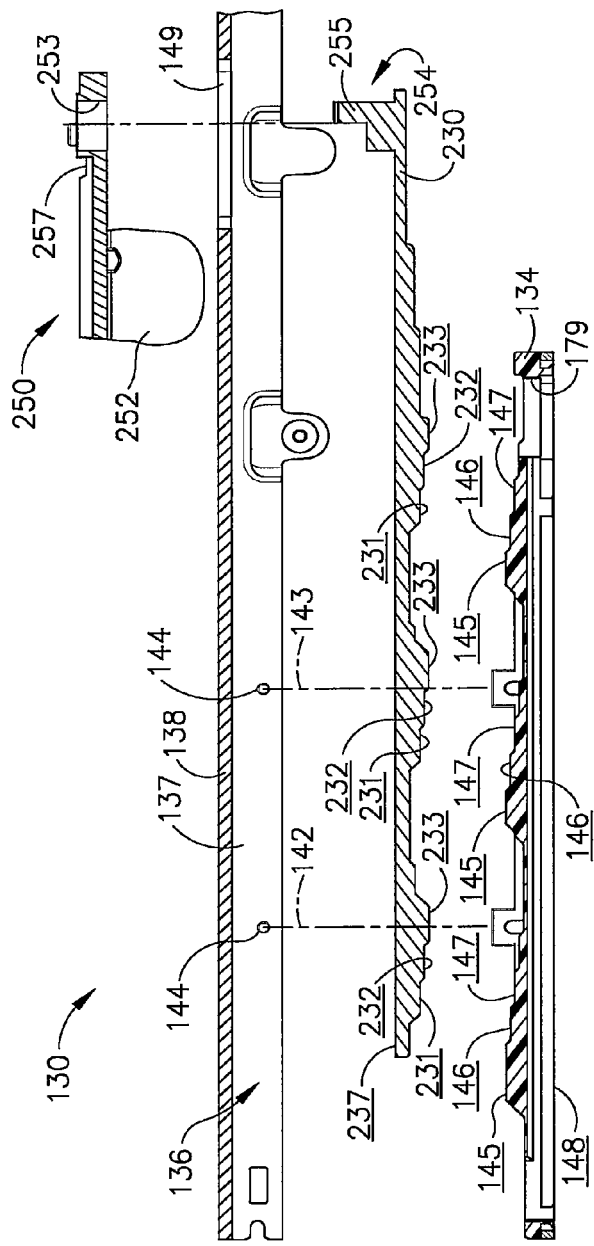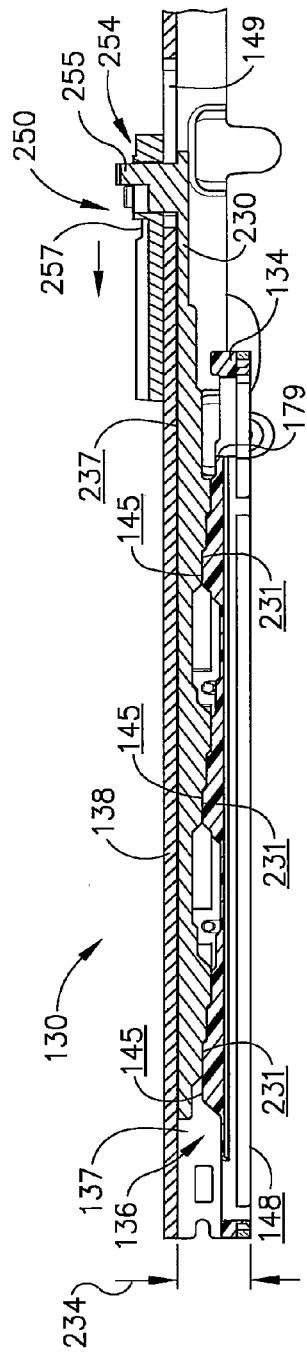

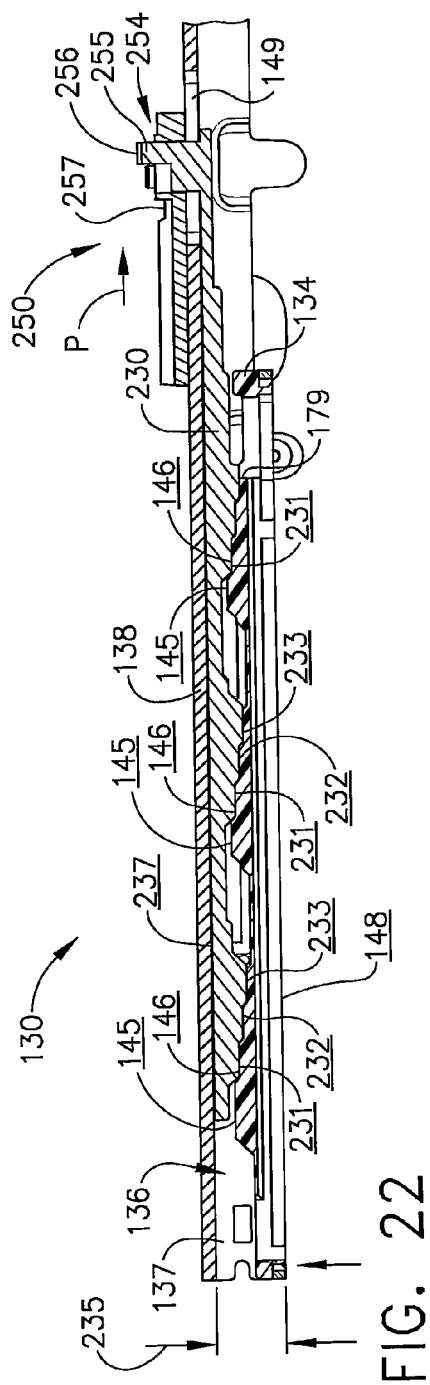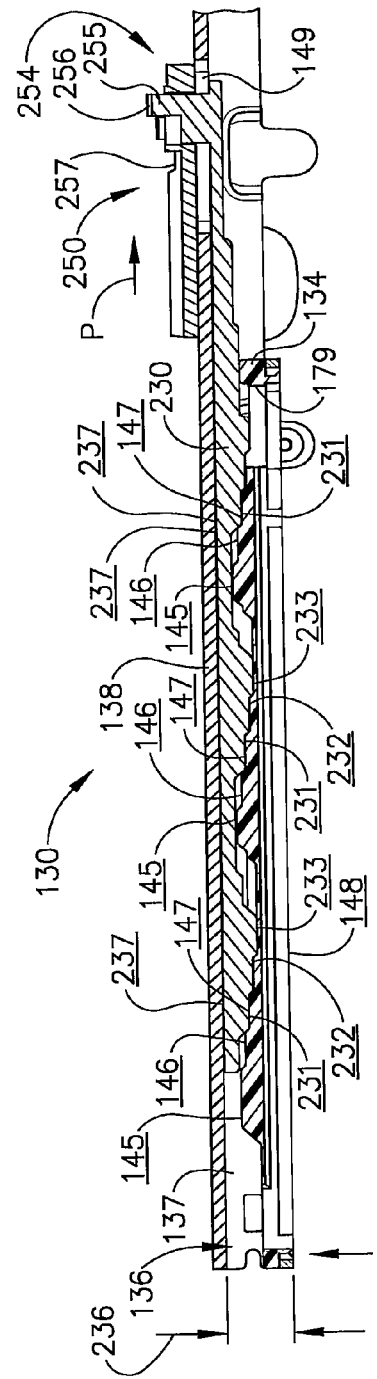

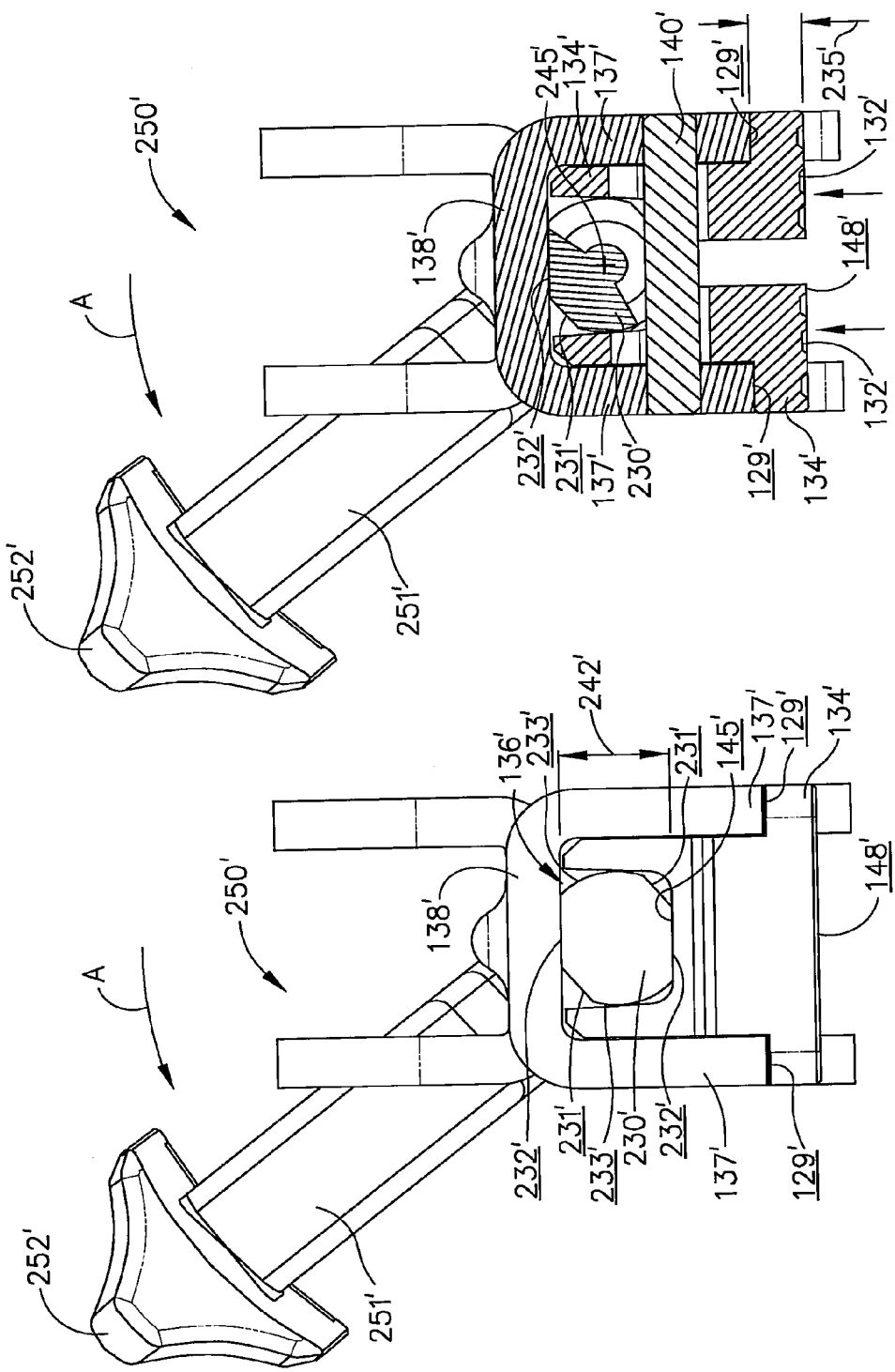

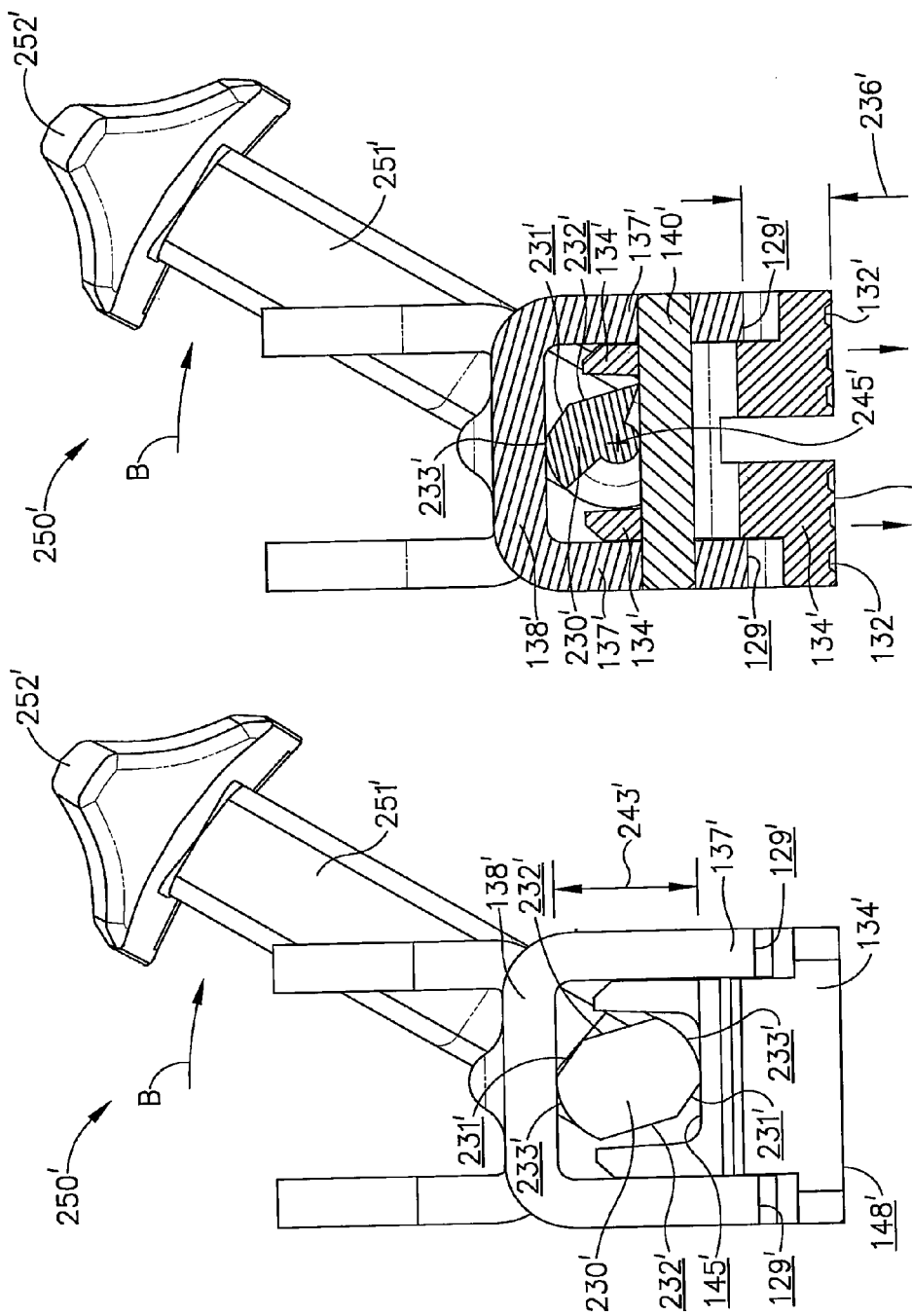

SURGICAL STAPLER HAVING A CLOSURE MECHANISM

CROSS-REFERENCE TO RELATED APPLICATION

This non-provisional patent application claims the benefit under 35 U.S.C. §119(e) of U.S. Provisional Patent Application No. 61/250,377, entitled SURGICAL STAPLER, which was filed on Oct. 9, 2009, the entire disclosure of which is incorporated by reference herein.

BACKGROUND i. Technical Field

The present invention relates to stapling instruments and, in various embodiments, to a surgical stapling instrument for producing one or more rows of staples.

ii. Background of the Related Art

In recent years, there has been an increasing tendency for surgeons to use stapling instruments to suture body tissues such as a lung, an esophagus, a stomach, a duodenum and/or other organs in the intestinal tract. The use of an appropriate stapling instrument in many instances may perform a better job in less time and simplify previously difficult surgical procedures such as gastrointestinal anastomoses. Previous linear two and four row cutting staplers comprised cartridge-less instruments into which staples were individually hand-loaded. Other previous devices have included a presterilized disposable staple loading unit and a cutting member which could be utilized for dividing the tissue and forming the rows of staples simultaneously. An example of such a surgical stapler is disclosed in U.S. Pat. No. 3,499,591, entitled INSTRUMENT FOR PLACING LATERAL GASTROINTESTINAL ANASTOMOSES, which issued on Mar. 10, 1970, the entire disclosure of which is hereby incorporated by reference herein.

A stapling instrument can include a pair of cooperating elongate jaw members, wherein each jaw member can be adapted to be inserted into an internal, tubular body organ to be anastomosed. In various embodiments, one of the jaw members can support a staple cartridge with at least two laterally spaced rows of staples, and the other jaw member can support an anvil with staple-forming pockets aligned with the rows of staples in the staple cartridge. Generally, the stapling instrument can further include a pusher bar and knife blade which are slidable relative to the jaw members to sequentially eject staples from the staple cartridge via camming surfaces on the pusher bar. In at least one embodiment, the camming surfaces can be configured to activate a plurality of staple drivers carried by the cartridge and associated with the individual staples to push the staples against the anvil and form laterally spaced rows of deformed staples in the tissue gripped between the jaw members. In typical stapling instruments, however, the anvil is unmovable relative to the staple cartridge once the jaw members have been assembled together and the formed height of the staples cannot be adjusted. In at least one embodiment, the knife blade can trail the pusher bar and cut the tissue along a line between the staple rows. Examples of such stapling instruments are disclosed in U.S. Pat. No. 4,429,695, entitled SURGICAL INSTRUMENTS, which issued on Feb. 7, 1984, the entire disclosure of which is hereby incorporated by reference herein.

SUMMARY

In at least one form of the present invention, a surgical stapler can comprise a first handle portion comprising a staple cartridge channel configured to receive a staple, cartridge and a second handle portion comprising an anvil. The stapler further comprises a rotatable latch and a latch projection, wherein the latch is rotatably coupled to one of the first handle portion and the second handle portion and wherein the latch projection extends from the other of the first handle portion and the second handle portion. The latch is configured to engage the latch projection to move the first handle portion and the second handle portion toward one another. In various embodiments, the latch projection comprises a rotatable bearing wherein the latch is configured to contact the rotatable bearing when the latch engages the latch projection.

In at least one form of the present invention, a surgical stapler can comprise an anvil having a plurality of staple pockets formed in a tissue contacting surface. Each staple pocket can comprise a longitudinal axis, a first forming cup, and a second forming cup. The first forming cup can comprise a first interior sidewall comprising a first vertical portion which is substantially perpendicular to the tissue contacting surface. The second forming cup can comprise a second interior sidewall comprising a second vertical portion which is substantially perpendicular to the tissue contacting surface. In various embodiments, the first vertical portion and the second vertical portion can extend through the longitudinal axis, wherein the first interior sidewall and the second interior sidewall can comprise a trap for deforming a first staple leg of a staple to a first side of the longitudinal axis and for deforming a second staple leg of the staple to a second side of the longitudinal axis.

In at least one form of the present invention, a method for deforming a staple comprising a base, a first staple leg, and a second staple leg, wherein the base, the first staple leg, and the second staple leg are positioned within a common plane prior to being deformed, the method comprising positioning the first staple leg within a first cup of a staple pocket, the first cup comprising a first inner surface, applying a first compressive force to an end of the first staple leg to bend the first staple leg toward the base and the second staple leg, contacting the first inner surface with the end of the first staple leg to bend the end of the first staple leg toward a first side of the base, and deforming the first staple leg such that the end of the first staple leg crosses a mid-line of the staple defined between the first staple leg and the second staple leg.

BRIEF DESCRIPTION OF DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 11 is an exploded view of a staple sled and cutting member assembly of the staple cartridge assembly of FIG. 8;

FIG. 12 is a perspective view of the staple sled and cutting member assembly of FIG. 11;

FIG. 20 is an exploded cross-sectional elevational view of the anvil assembly of FIG. 17;

FIG. 21 is a cross-sectional assembly view of the anvil assembly of FIG. 17 illustrating an anvil adjustment member in a first position;

FIG. 22 is a cross-sectional assembly view of the anvil assembly of FIG. 17 illustrating the anvil adjustment member of FIG. 21 in a second position;

FIG. 23 is a cross-sectional assembly view of the anvil assembly of FIG. 17 illustrating the anvil adjustment member of FIG. 21 in a third position;

FIG. 32 is an end view of the surgical stapling instrument of FIG. 24 illustrating the rotatable anvil adjustment member of FIG. 28 rotated in a first direction into a second orientation;

FIG. 33 is a cross-sectional end view of the surgical stapling instrument of FIG. 24 illustrating the anvil adjustment member in the second orientation of FIG. 32;

FIG. 34 is an end view of the surgical stapling instrument of FIG. 24 illustrating the rotatable anvil adjustment member of FIG. 28 rotated in a second direction into a third orientation;

FIG. 35 is a cross-sectional end view of the surgical stapling instrument of FIG. 24 illustrating the anvil adjustment member in the third orientation of FIG. 34;

Corresponding reference characters indicate corresponding parts throughout the several views. The exemplifications set out herein illustrate preferred embodiments of the invention, in one form, and such exemplifications are not to be construed as limiting the scope of the invention in any manner.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

The entire disclosures of the following commonly-owned, non-provisional U.S. patent applications are hereby incorporated by reference herein:

SURGICAL STAPLING INSTRUMENT WITH CUTTING MEMBER ARRANGEMENT, U.S. patent application Ser. No. 12/234,149, now U.S. Pat. No. 7,905,381;

SURGICAL STAPLER WITH APPARATUS FOR ADJUSTING STAPLE HEIGHT, U.S. patent application Ser. No. 12/234,133, now U.S. Pat. No. 7,954,686;

LOCKOUT ARRANGEMENT FOR A SURGICAL STAPLER, U.S. patent application Ser. No. 12/234,113, now U.S. Pat. No. 7,832,612;

SURGICAL STAPLER HAVING AN INTERMEDIATE CLOSING POSITION, U.S. patent application Ser. No. 12/234,143, now U.S. Pat. No. 7,857,186;

A METHOD FOR FORMING A STAPLE, filed on even date herewith, U.S. patent application Ser. No. 12/622,130, now U.S. Publication No. 2011/0087276; and SURGICAL STAPLER COMPRISING A STAPLE POCKET, filed on even date herewith, U.S. patent application Ser. No. 12/622,113, now U.S. Pat. No. 8,141,762.

Figure 1:
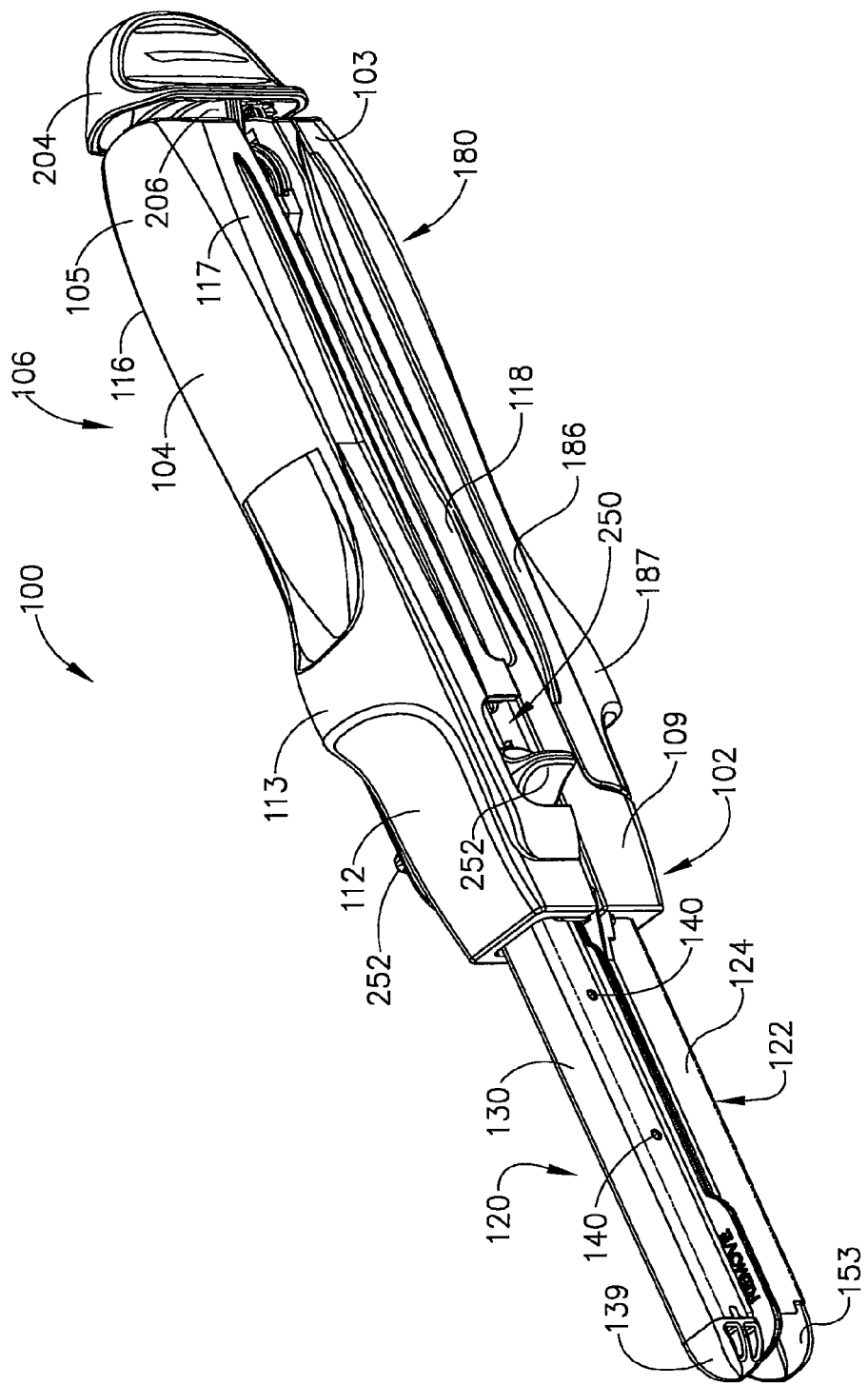
FIG. 1 is a perspective view of a surgical stapling instrument in accordance with at least one embodiment of the present invention.

Referring to FIG. 1, a surgical stapling instrument, generally 100, can comprise a first handle portion 102 and a second handle portion 104. In various embodiments, first handle portion 102 and second handle portion 104 can be configured to be grasped by a surgeon, for example, and can comprise hand grip portion 106. In at least one embodiment, first handle portion 102, referring to FIGS. 2 and 3, can include a first cover 108 attached to a first frame 110 and, similarly, second handle portion 104 can include a second cover 112 attached to a second frame 114. Covers 108 and 112 can be ergonomically contoured, or otherwise suitably contoured, to assist a surgeon in manipulating stapling instrument 100 within a surgical site. In various embodiments, handle covers 108 and 112, for example, can include enlarged protrusions 109 and 113, respectively, which can facilitate the insertion of stapling instrument 100 into a surgical site. In various embodiments, handle covers 108 and 112 can be made of plastic, lightweight materials, and/or any other suitable material, for example, while handle frames 110 and 114 can be made of stainless steel, titanium, and/or any other suitable material, for example.

Figure 2:
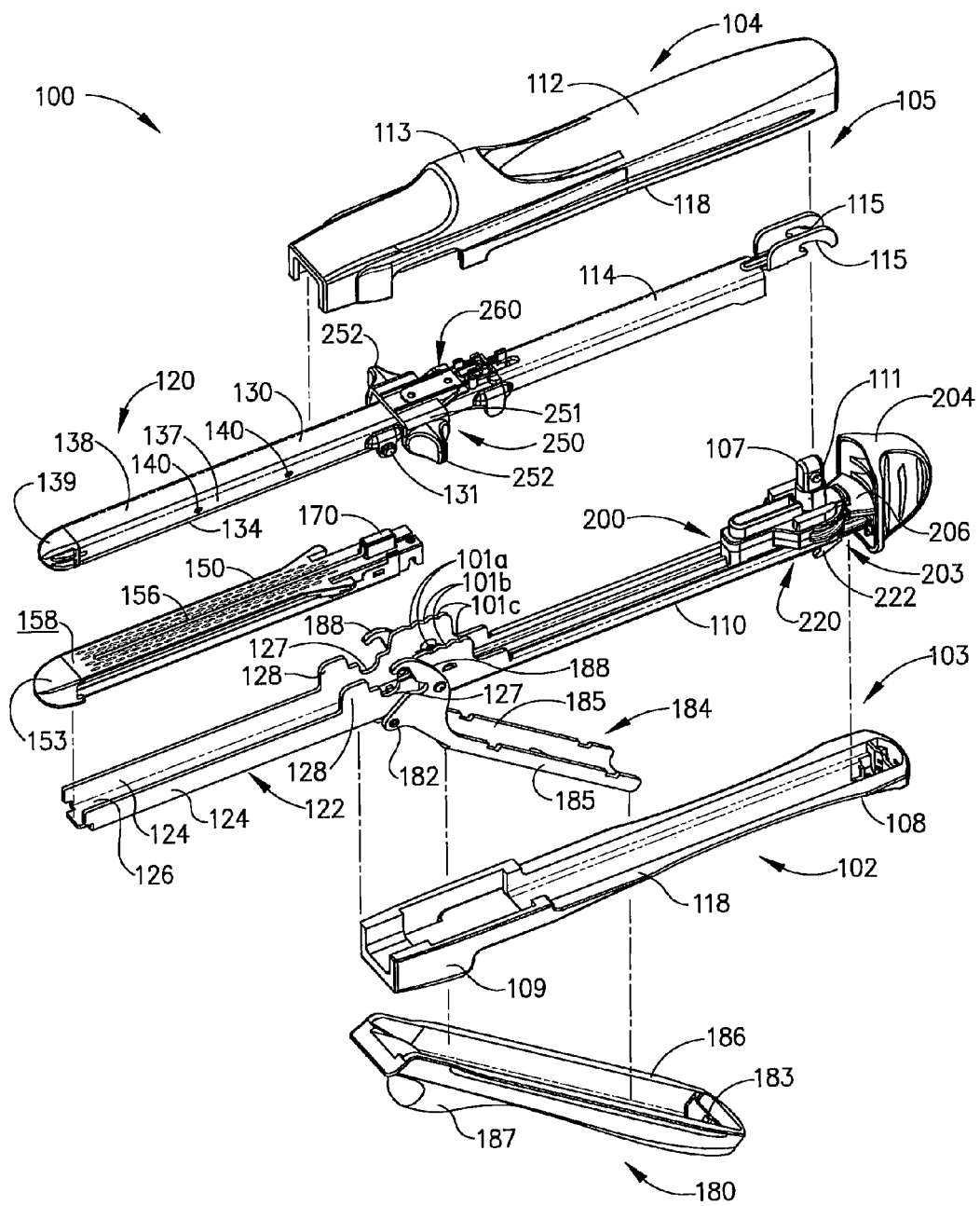
FIG. 2 is an exploded perspective view of the surgical stapling instrument of FIG. 1.

In various embodiments, referring again to FIGS. 1-3, the distal ends of handle portions 102 and 104 can comprise an end-effector 120 which can be configured to treat tissue within a surgical site, for example. In at least one such embodiment, end-effector 120 can include a staple cartridge channel 122 configured to receive and/or retain a staple cartridge as described in greater detail further below. In certain embodiments, staple cartridge channel 122 can comprise a one-piece elongated channel-shaped frame extending from first handle portion frame 110. In at least one embodiment, staple cartridge channel 122 can include a pair of opposed, elongated side walls 124 connected by a bottom wall 126. Along the rearward, or proximal, portion of staple cartridge channel 122, a pair of spaced, upstanding side flanges 128 can extend upwardly from opposed side walls 124. In various embodiments, the width of staple cartridge channel 122 between side flanges 128 can be greater than the width of the upper jaw member, or anvil, 130 extending from second handle portion 104. In at least one embodiment, the distance between flanges 128 can be configured to permit at least a portion of anvil 130 to be received between side flanges 128 when the stapling instrument is assembled for operation. As shown in FIG. 2, each side flange 128 of can include a notch, or recess, 127, for example, which can be configured to receive one or more latch projections 131, for example, extending from anvil 130, and/or any other suitable portion of second handle portion 104, as described in greater detail further below.

Figure 9:
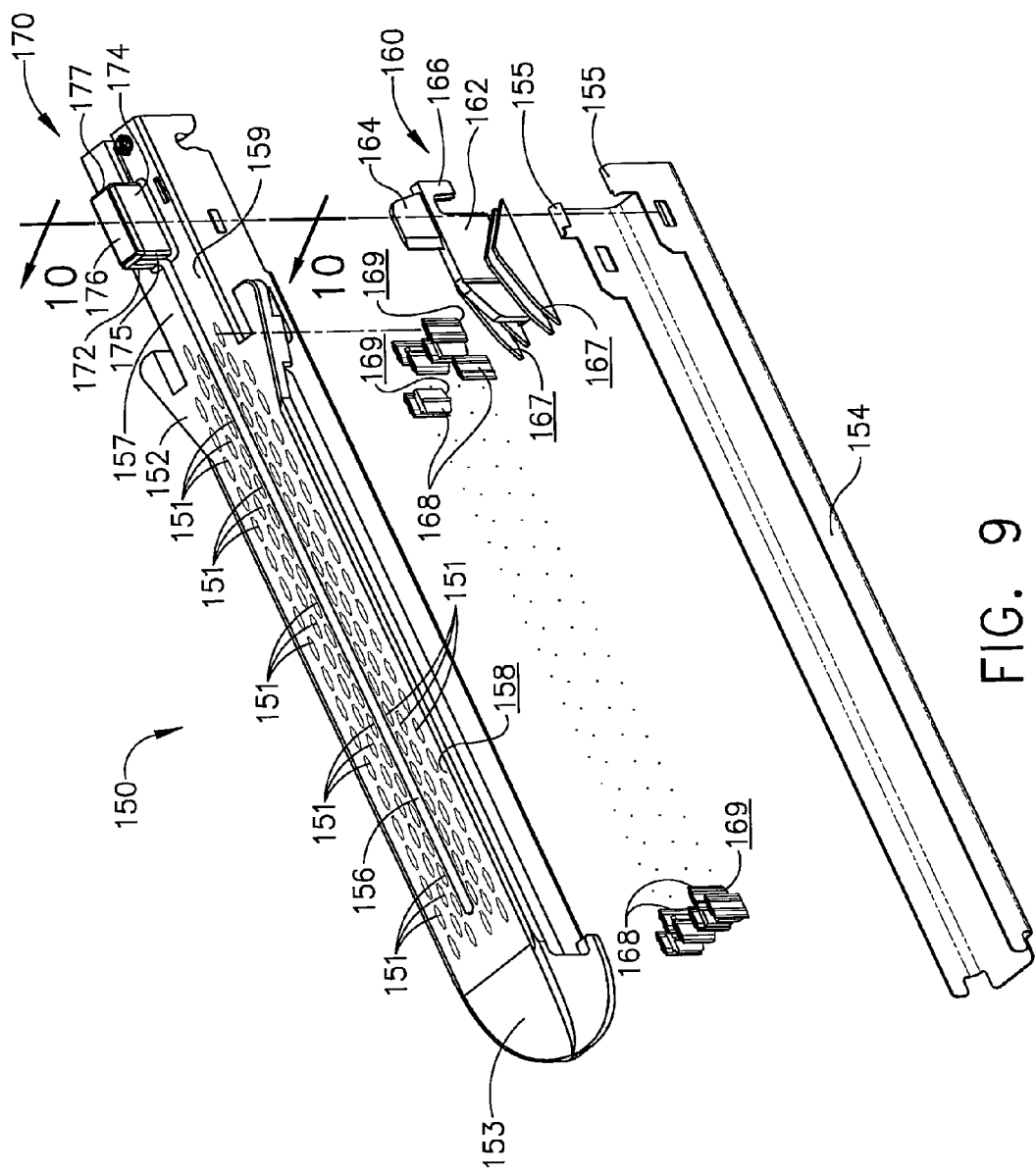
FIG. 9 is an exploded view of the staple cartridge assembly of FIG. 8.
Figure 10:
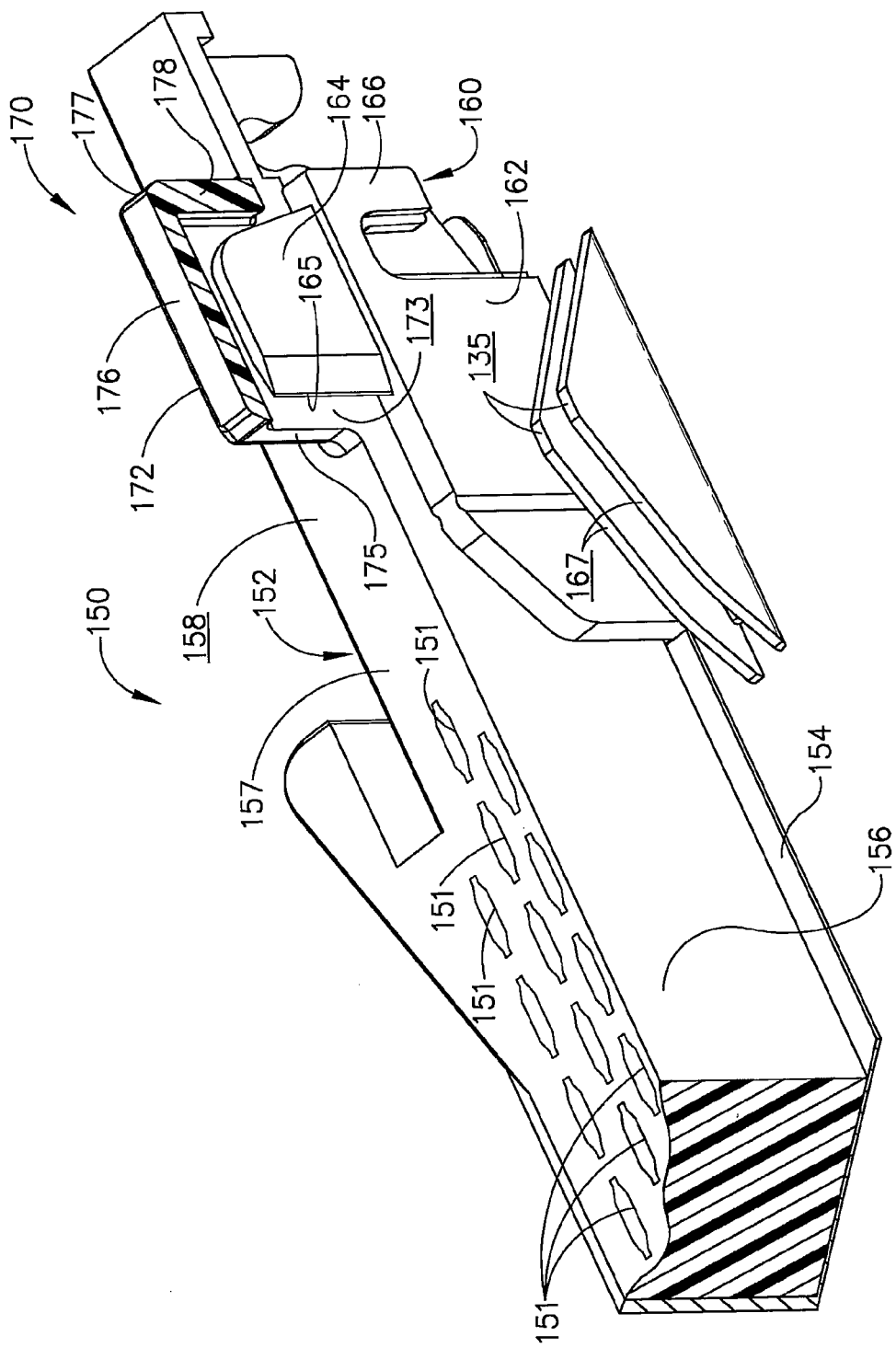
FIG. 10 is a cross-sectional view of the staple cartridge assembly of FIG. 8 taken along line 10-10 in FIG. 9.

As indicated above, referring once again to FIGS. 1-3, staple cartridge channel 122 can be configured to support and/or retain a staple cartridge, such as staple cartridge 150, for example, within end-effector 120, wherein the staple cartridge can include one or more staples (not illustrated) removably stored therein. In various embodiments, referring to FIGS. 8-10, staple cartridge 150 can include one or more staple cavities 151 which can be configured to store staples in any suitable arrangement, such as in at least two laterally-spaced longitudinal rows, for example. In at least one embodiment, referring to FIGS. 9 and 10, staple cartridge 150 can include staple cartridge body 152 and pan 154, wherein staple cartridge body 152 and/or pan 154 can be configured to define a channel, or path, for slidably receiving a staple sled and/or cutting member therein. In at least one embodiment, pan 154 can include flexible arms 155, for example, which can be configured to engage staple cartridge body 152 in a snap-fit and/or press-fit arrangement. Referring to FIGS. 10-12, staple cartridge 150 can further include staple sled assembly 160 which can include staple sled portion 162 and, in addition, cutting member 164. In various embodiments, cutting member 164 can include cutting edge 165 and lock arm 166, for example, wherein lock arm 166 can be configured to be press-fit and/or snap-fit into aperture 163 in staple sled 162 when cutting member 164 is assembled to staple sled portion 162. In other various embodiments, staple sled portion 162 can be integrally molded to cutting member 164.

Figure 8:
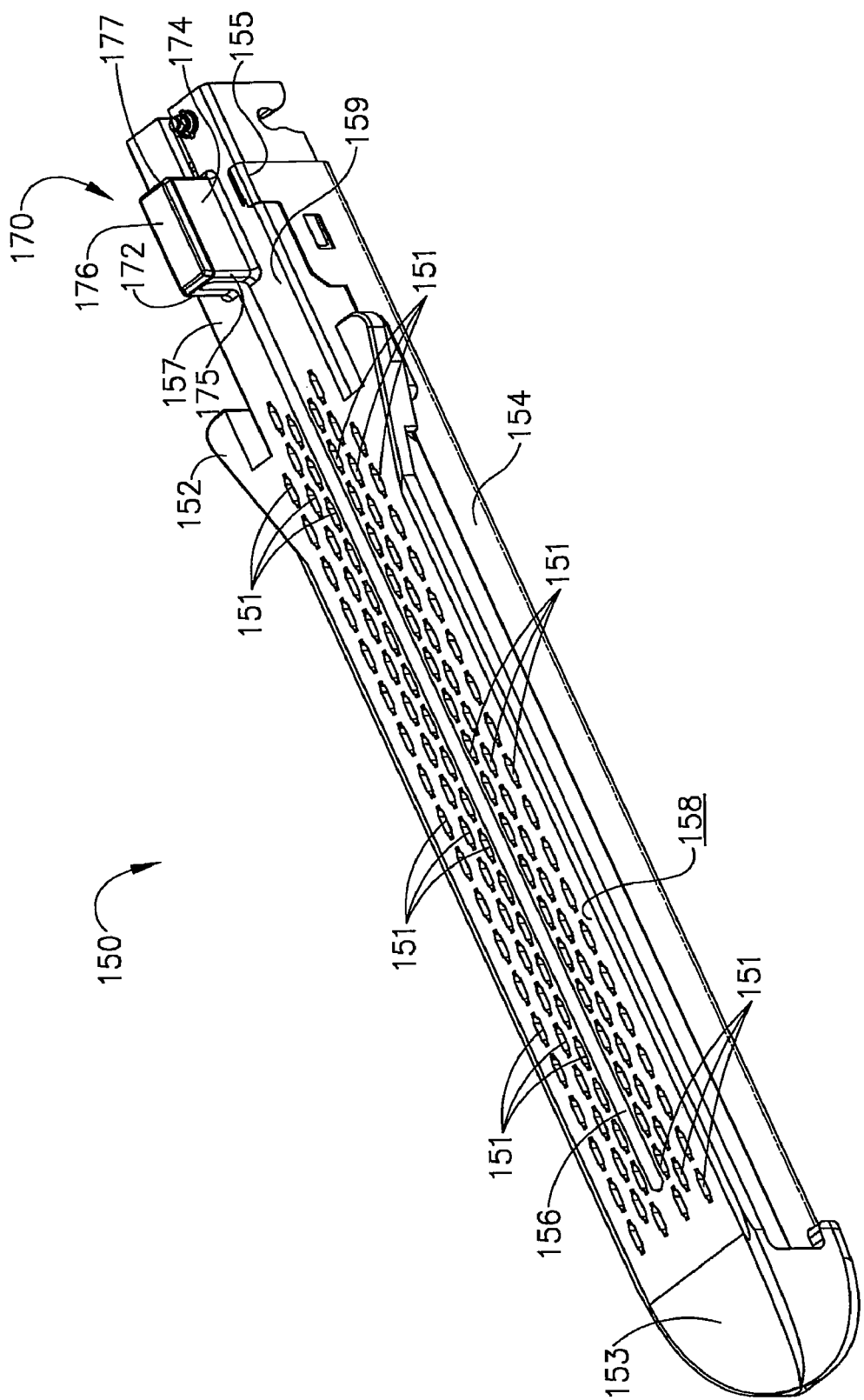
FIG. 8 is a perspective view of a staple cartridge assembly of the surgical stapling instrument of FIG. 1.

Further to the above, referring to FIGS. 8-10, staple cartridge body 152 can include a slot, such as slot 156, for example, which can be configured to receive at least a portion of cutting member 164 therein, and/or any other portion of staple sled assembly 160 and pusher bar assembly 200 (discussed below), wherein slot 156 can be configured to permit cutting member 164 to be moved between first and second positions within staple cartridge 150. In various embodiments, slot 156 can be configured to permit cutting member 164 to be moved between a proximal position (FIG. 10) and a distal position in order to incise tissue positioned intermediate staple cartridge 150 and anvil 130, for example. Referring again to FIGS. 10-12, staple sled portion 162 can include cam, ramp, or actuator, surfaces 167 which can be configured to engage staple drivers positioned within staple cartridge 150. In various embodiments, referring to FIG. 9, staple cartridge 150 can include staple drivers 168 which can be lifted, or slid, upwardly within staple cavities 151 by sled portion 162 such that the upward movement of staple drivers 168 can eject, or deploy, staples at least partially positioned within staple cavities 151. While staple drives 168 can be, in fact, lifted vertically upwardly, the term upward, and the like, can mean that staple drivers 168, for example, are moved toward the top surface, or deck, 158 of the staple cartridge and/or toward anvil 130, for example. In certain embodiments, as illustrated in FIG. 9, each staple driver 168 can include one or more sloped surfaces 169 oriented at the same angle as a cam surface 167, and/or any other suitable angle, which can provide a relatively flat, or at least substantially flat, sliding contact surface between staple sled 162 and staple drivers 168. In various embodiments, a staple driver can be configured to deploy only one staple, while, in certain embodiments, a staple driver can be configured to simultaneously deploy two or more staples located in adjacent rows, for example. Other devices are disclosed in U.S. patent application Ser. No. 12/030,424, entitled SURGICAL STAPLING INSTRUMENT WITH IMPROVED FIRING TRIGGER ARRANGEMENT, which was filed on Feb. 13, 2008, the entire disclosure of which is incorporated by reference herein.

In various embodiments, as described above, a surgical stapling instrument can include a cutting member/staple sled assembly configured to incise tissue and deploy staples from a staple cartridge. In certain embodiments, though, a surgical stapling instrument may not require, or include, a cutting member. In at least one such embodiment, a staple cartridge can include a staple sled positioned therein and/or a surgical instrument can be configured to move a staple sled into a staple cartridge in order to staple tissue, for example, without otherwise dissecting it. In certain other embodiments, a staple cartridge can include a staple sled positioned therein where a surgical instrument can include a cutting member movable into, or relative to, the staple cartridge. In at least one such embodiment, the cutting member can be advanced into contact with the staple sled such that the cutting member and staple sled can be advanced together. Thereafter, the cutting member can be sufficiently retracted to allow the staple cartridge to be detached from the surgical instrument and replaced with a new staple cartridge having a new staple sled. Such embodiments may be useful when a staple sled may become worn or deformed during use. Other embodiments are envisioned where a staple cartridge can include a cutting member positioned therein where a surgical instrument can include a staple sled movable into, or relative to, the staple cartridge. In at least one such embodiment, similar to the above, the staple sled can be advanced into contact with the cutting member such that the cutting member and staple sled can be advanced together. Thereafter, the staple sled can be sufficiently retracted to allow the staple cartridge to be detached from the surgical instrument and replaced with a new staple cartridge having a new cutting member. Such embodiments may be useful when a cutting member may become worn or deformed during use. In various embodiments, as described in greater detail below, the staple cartridge can include a protective housing or cover configured to prevent, or at least reduce the possibility of, a surgeon or other clinician from touching the cutting member positioned within the staple cartridge while handling the staple cartridge, for example.

Figure 3:
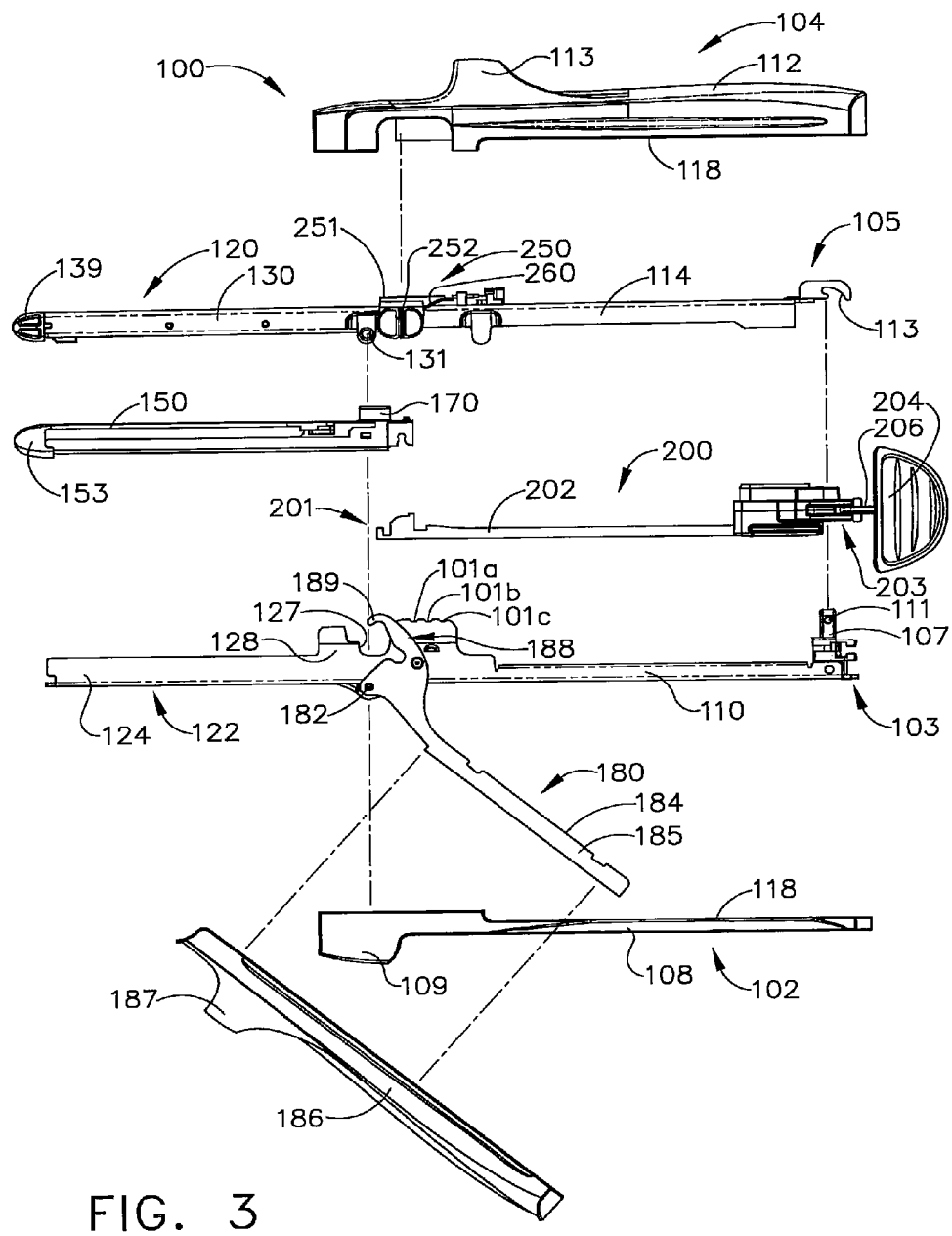
FIG. 3 is an exploded elevational view of the surgical stapling instrument of FIG. 1.

In various embodiments, further to the above, staple cartridge channel 122 and/or staple cartridge 150, for example, can include one or more co-operating projections and/or recesses, for example, which can be configured to removably retain staple cartridge 150 within staple cartridge channel 122. Once staple cartridge 150 has been inserted into staple cartridge channel 122, in various embodiments, the first handle portion 102 can be assembled to the second handle portion 104. In other various embodiments, the staple cartridge may be inserted into the staple cartridge channel after the first and second handle portions have been assembled together. In either event, referring to FIGS. 1-7, first handle portion 102 and second handle portion 104 can include proximal ends 103 and 105, respectively, which can be assembled together such that the first and second handle portions can be rotatably or pivotably coupled to one another. In various embodiments, referring to FIGS. 2 and 3, first handle portion 102 can include one or more pins, or projections, 111 extending therefrom which can be configured to be slidably received within one or more grooves, channels, or slots 115 in second handle portion 104. In certain embodiments, slots 115 can be defined in second handle frame 114 and projections 111 can extend from a proximal end post 107 extending from first handle frame 110, for example. In order to assemble first handle portion 102 and second handle portion 104, referring to FIG. 4, the open ends of slots 115 can be aligned with projections 111 such that second handle portion 104, for example, can be translated relative to first handle portion 102 and projections 111 can be slid within slots 115. In at least one embodiment, as illustrated in FIGS. 2 and 3, the open ends of slots 115 can be located proximally with respect to their closed ends. In at least one such embodiment, proximal end 105 of second handle portion 104 can be positioned distally with respect to proximal end 103 of first handle portion 102 such that second handle portion 104 can be moved proximally in order to position projections 111 within slots 115. In various other circumstances, first handle portion 102 can be positioned proximally with respect to second handle portion 104 and slid distally in order to position projections 111 within slots 115.

Figure 5:
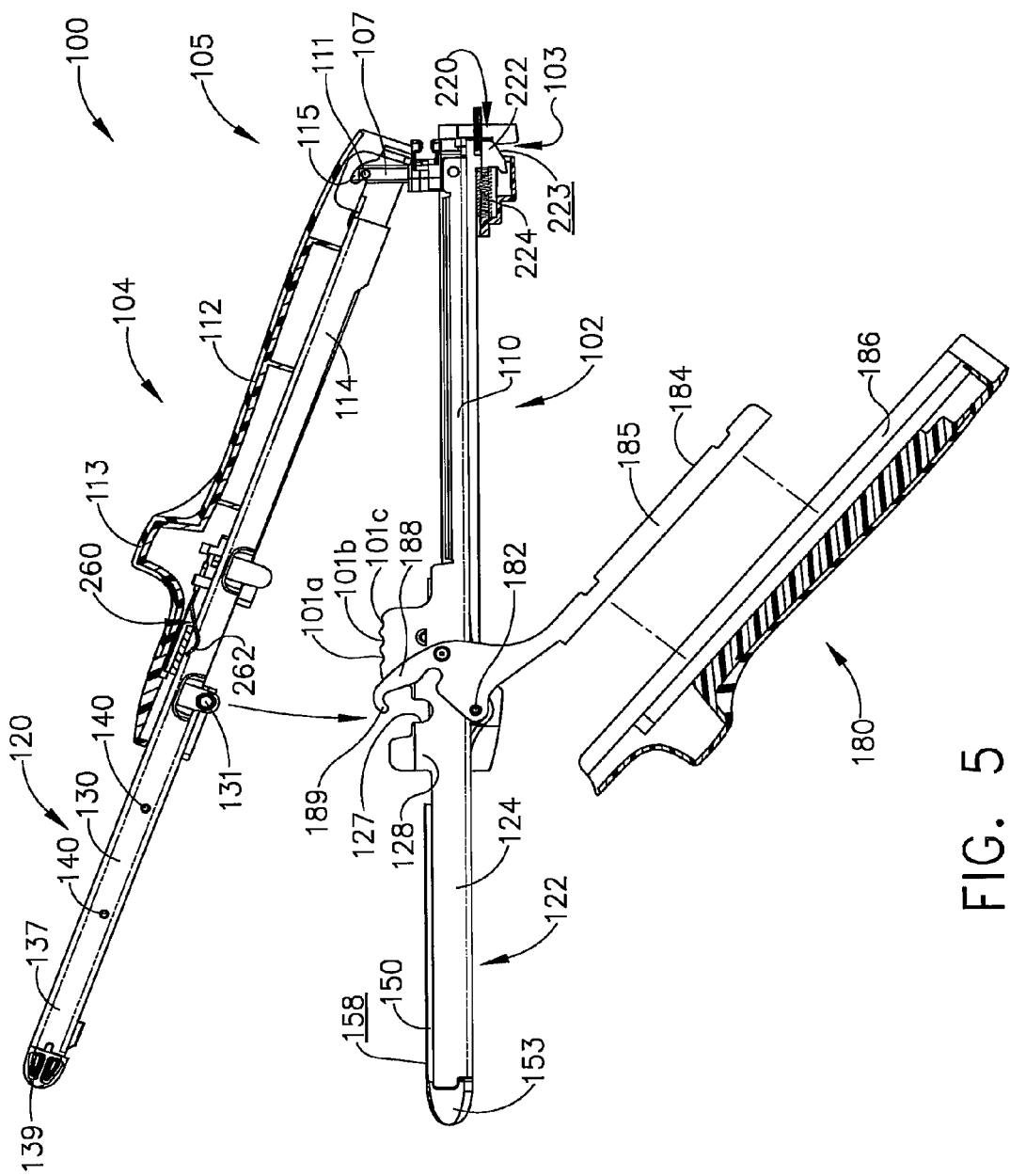
FIG. 5 is a partial cross-sectional view of the surgical stapling instrument of FIG. 1 illustrating the proximal end of the first portion of FIG. 4 being locked to the proximal end of the second portion of FIG. 4 and illustrating the second portion being rotated toward the first portion.

In various embodiments, referring to FIG. 5, second handle portion 104 can be rotated toward first handle portion 102 such that anvil 130 can be moved into position relative to staple cartridge 150 and/or staple cartridge channel 122. In certain embodiments, first handle portion 102 can be rotated toward second handle portion 104 and/or the first and second handle portions can be rotated toward each other. In any event, projections 111 and slots 115, when engaged with one another, can comprise a pivot about which one or both of the first and second handle portions can be moved relative to each other. In various embodiments, second handle portion 104 can be moved relative to first handle portion 102 such that anvil 130 is moved into close opposition to staple cartridge 150. In certain embodiments, referring to FIG. 6, second handle portion 104 can be moved relative to first handle portion 102 such that latch projections 131 extending from second handle portion 104 can be aligned with and/or inserted into recesses 127 within first handle portion 102. In various embodiments, referring primarily to FIGS. 2 and 3, first handle portion 102 can further include latching mechanism 180 rotatably mounted thereto which can be utilized to engage latch projections 131 extending from second handle portion 104 and secure the first and second handle portions together. Although not illustrated, other embodiments are envisioned in which a latching mechanism is rotatably mounted to the second handle portion and latch projections can extend from the first handle portion. In any event, in at least one embodiment, latching mechanism 180 can be mounted to first frame 110 by one or more pivot pins 182 which can be configured to define an axis about which latch 180 can be rotated.

Figure 4:
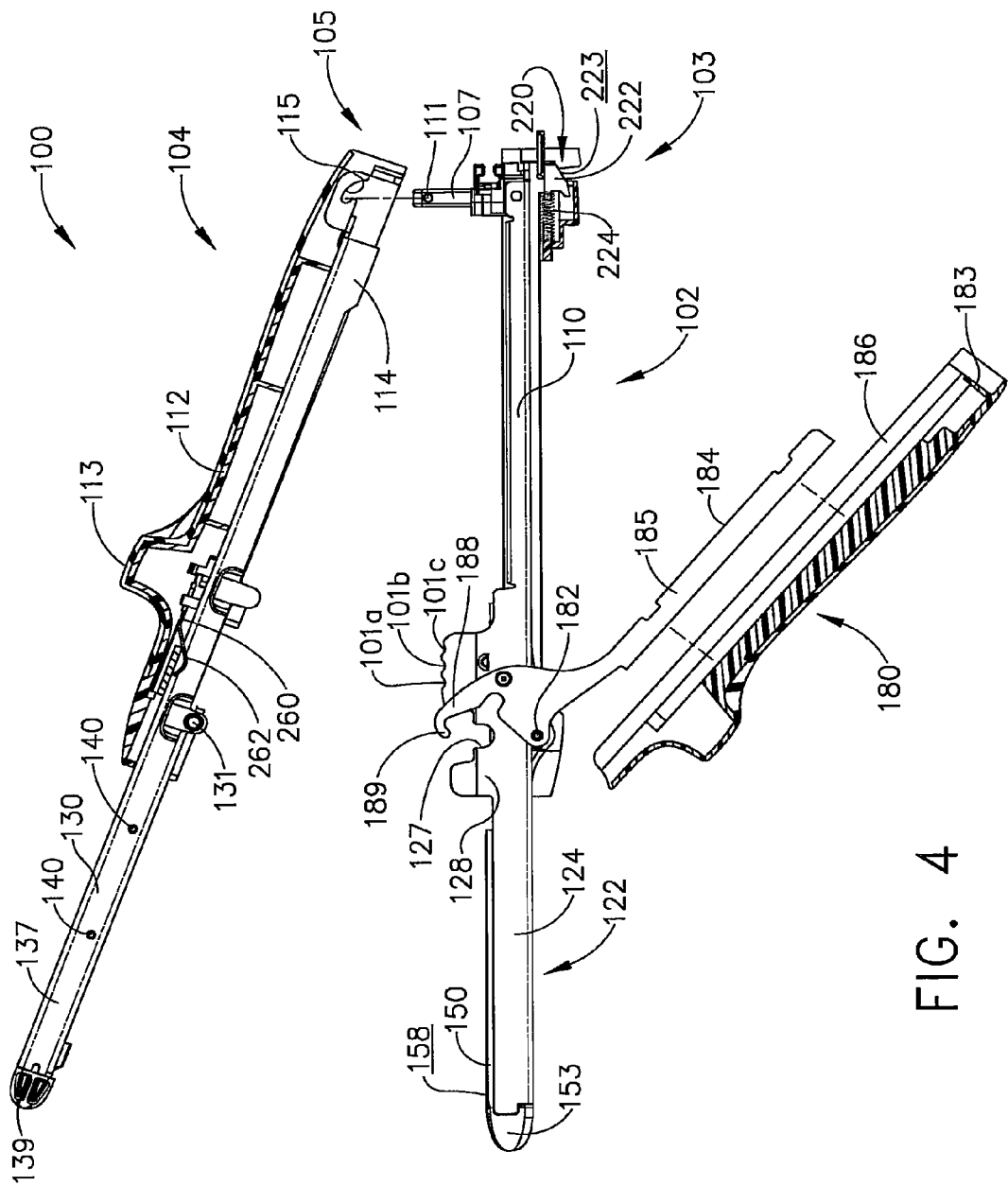
FIG. 4 is a partial cross-sectional view of the surgical stapling instrument of FIG. 1 illustrating first and second portions being assembled together.
Figure 6:
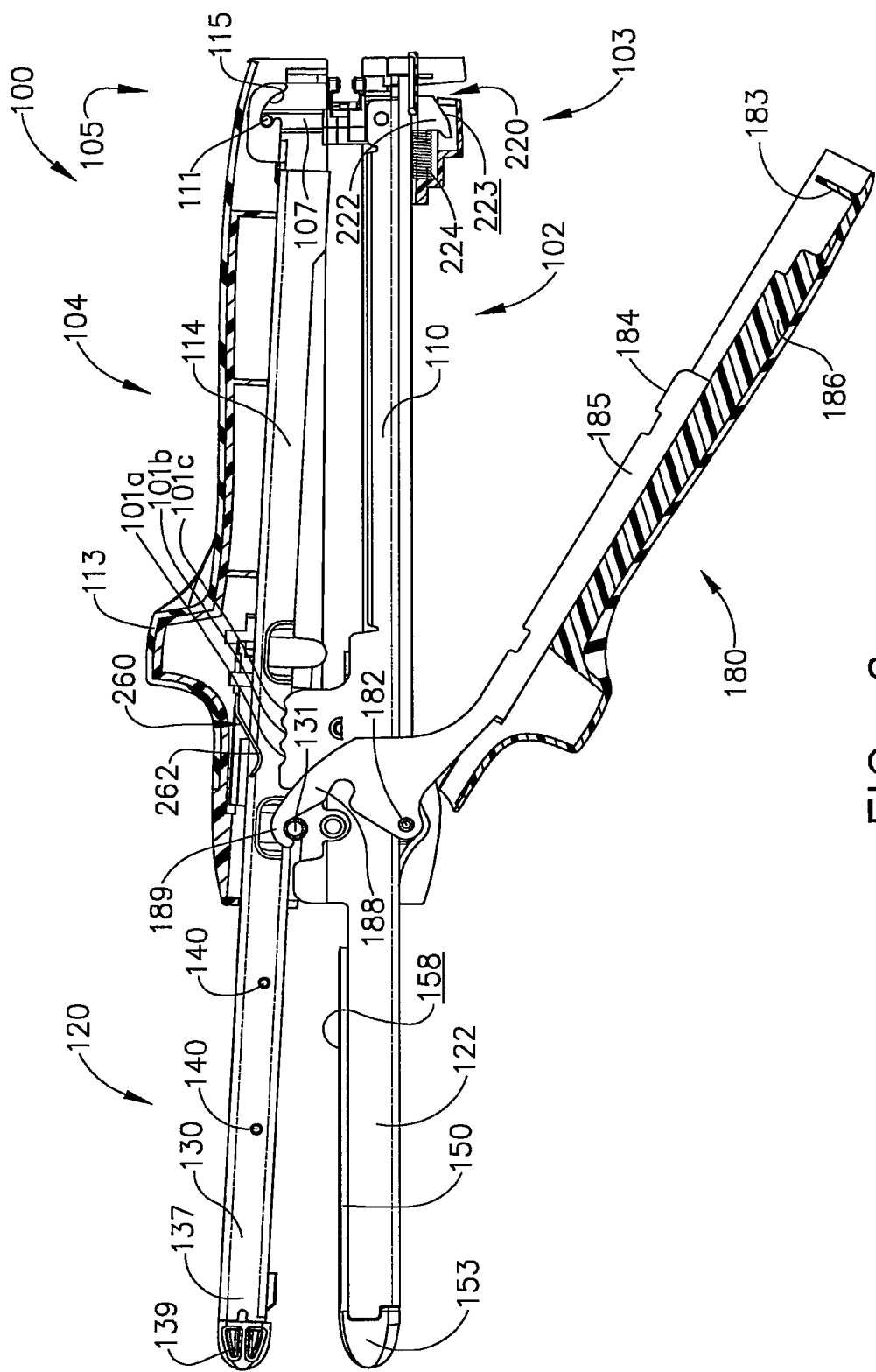
FIG. 6 is a partial cross-sectional view of the surgical stapling instrument of FIG. 1 illustrating a latch rotatably mounted to the first portion, wherein the latch is engaged with the second portion and wherein the latch has been rotated into a partially-closed position.
Figure 7:
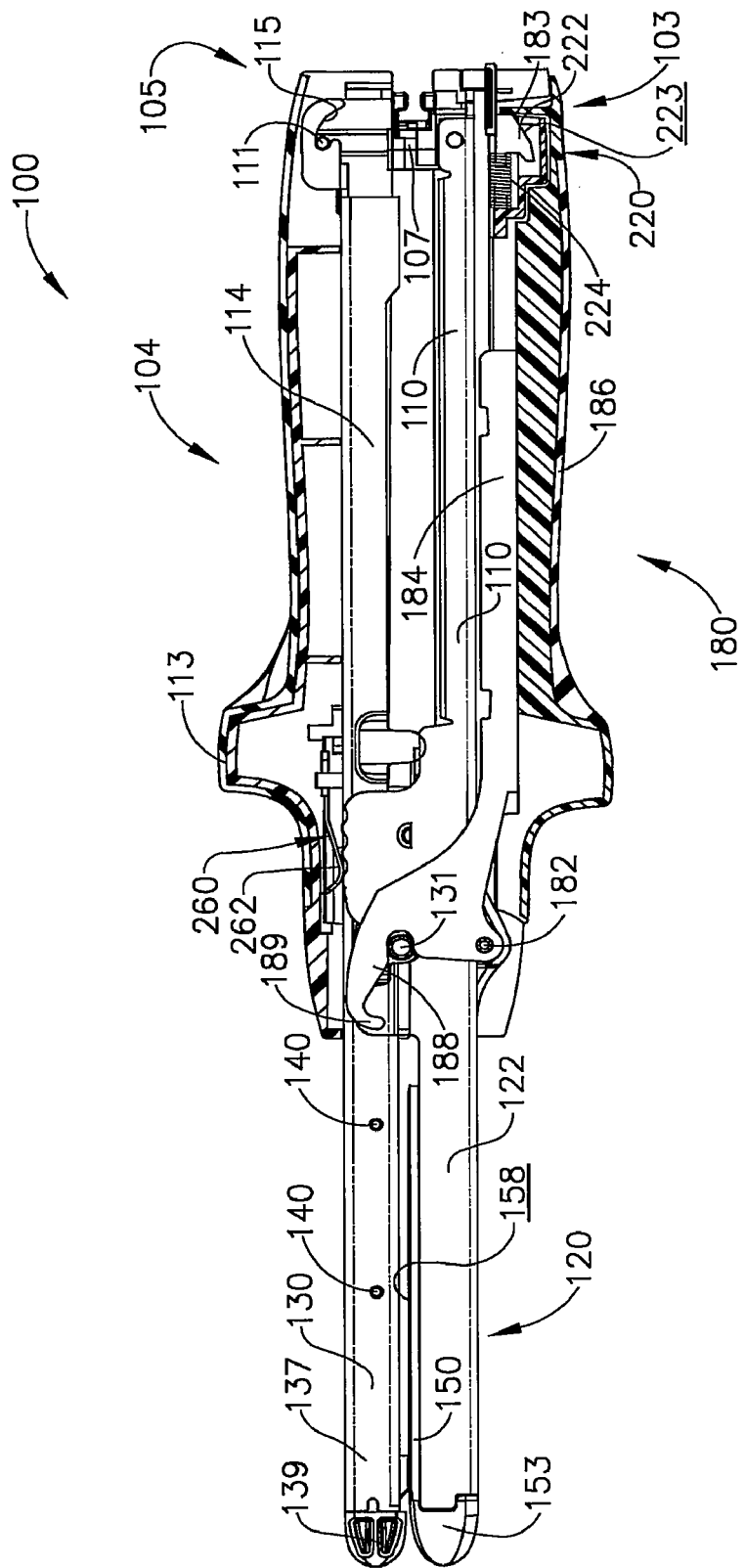
FIG. 7 is a partial cross-sectional view of the surgical stapling instrument of FIG. 1 illustrating the latch of FIG. 6 in a closed position.

In certain embodiments, referring now to FIGS. 4 and 5, latching mechanism 180 can include latch frame 184 and, in addition, latch cover 186 assembled to latch frame 184. In other various embodiments, the latch cover and the latch frame can comprise an integral unit or, in certain embodiments, the latching mechanism may not even include a cover. In certain embodiments, latch frame 184 can be channel-shaped and can include a pair of opposed, elongated side walls 185 which are spaced apart by a distance sufficient to span first frame portion 110. In at least one embodiment, latch cover 186 can be made of plastic, lightweight materials, and/or any other suitable materials, for example, while latch frame 184 can be made of stainless steel and/or any other suitable material, for example. In certain embodiments, when latching mechanism 180 is closed, as illustrated in FIG. 7, latch cover 186 can be aligned with first handle cover 108. Latch cover 186 can include contoured portion 187 which can be configured to assist a surgeon in manipulating surgical instrument 100 wherein, in at least one embodiment, contoured portion 187 can be aligned with, or at least substantially aligned with, protrusion 109 extending from first handle cover 108. Latching mechanism 180 can further include one or more latch arms 188 extending therefrom which can be configured to engage one or more latch projections 131 extending from second handle portion 104 and pull and/or secure projections 131 within recesses 127 as illustrated in FIG. 7. In at least one embodiment, at least one of latch arms 188 can be integrally-formed with latch frame 184. In certain embodiments, referring to FIG. 6, at least one of latch arms 188 can include a distal hook 189 which can be configured to wrap around at least a portion of projections 131 so as to encompass or surround, or at least partially encompass or surround, projections 131. In at least one embodiment, latch arms 188 can act as an over-center latch to maintain latching mechanism 180 in its latched, or closed, position.

In use, in various circumstances, one of the first handle portion 102 and the second handle portion 104 can be positioned on a first side of tissue within a surgical site and the other handle portion can be rotated into position on the opposite side of the tissue. In such embodiments, staple cartridge 150 can be positioned on one side of the tissue and anvil 130 can be positioned on the other side of the tissue. Thereafter, as also outlined above, latching mechanism 180 can be actuated such that it can be moved between an open position and a closed position in order to latch second handle portion 104 to first handle portion 102 and apply a clamping force to the tissue positioned between staple cartridge 150 and anvil 130. In certain circumstances, latching mechanism 180 can be moved between an open position (FIG. 5), a partially-closed, or intermediate, position (FIG. 6), and a closed position (FIG. 7). In at least one such embodiment, referring to FIGS. 5 and 6, latching mechanism 180 can be moved between an open position in which latch arms 188 are not engaged with projections 131 and a partially-closed position in which latch arms 188 are engaged with projections 131 such that, although anvil 130 has been at least partially brought into opposition to staple cartridge 150, a sufficient gap can remain between anvil 130 and staple cartridge 150 which can allow end-effector 120 to be repositioned relative to the tissue, for example. Once the anvil 130 and staple cartridge 150 have been sufficiently positioned relative to the tissue, latching mechanism 180 can be moved between its partially-closed position and a closed position, as illustrated in FIG. 7.

In various embodiments, further to the above, a surgical stapling instrument can further include a biasing member which can be configured to bias the first handle portion of a stapling instrument away from a second handle portion. In at least one embodiment, as described in greater detail further below, a spring, and/or any suitably resilient material, can be positioned intermediate the first and second handle portions such that the anvil and staple cartridge of the stapling instrument can be biased away from each other. In certain embodiments, the spring can be configured to at least partially separate the first and second handle portions such that a gap exists between the anvil and the staple cartridge, wherein the gap can be sufficient to allow tissue to be positioned therebetween. In use, a surgeon can position such a surgical stapling instrument without having to separate and hold the first and second handle portions apart from each other. Such an instrument may be especially useful when the stapling instrument is in a partially-closed configuration and the surgeon is manipulating the instrument within a surgical site. After the surgeon is satisfied with the positioning of the stapling instrument, the surgeon can compress and/or disengage the spring and place the stapling instrument in a closed configuration.

In various circumstances, as outlined above, the distal end of first handle portion 102 can be moved relative to the distal end of second handle portion 104, especially when latching mechanism 180 is not engaged with, or only partially engaged with, projections 131 of second handle portion 104. In such circumstances, projections 111 and slots 115 at the proximal ends of the first and second handle portions can be configured to retain at least the proximal ends of the first and second handle portions together when the distal ends of the first and second handle portions are being moved relative to each other, for example. Stated another way, projections 111 and slots 115 can cooperate to prevent, or at least inhibit, first handle portion 102 from becoming completely detached from second handle portion 104. In certain embodiments, a first handle portion can include a first lock portion and a second handle portion can include a second lock portion, wherein the first and second lock portions can be configured to be engaged with one another and prevent the first handle portion from becoming completely detached from the second handle portion. In at least one embodiment, projections 111 can comprise the first lock portion and slots 115 can comprise the second lock portion. Previous stapling instruments lacked such lock portions and instead relied on a sole latching mechanism to keep the first and second handle portions together. In circumstances where the latching mechanisms of these previous stapling instruments were not fully engaged with both of the first and second handle portions, the first and second handle portions could become completely detached from one another, thereby requiring a surgeon, for example, to reposition and reassemble the handle portions. In certain circumstances, a complete detachment of the first and second handle portions of these previous staples could expose at least a portion of a cutting member.

In various embodiments, as outlined above, latching mechanism 180 can be configured to be moved between an open position, a partially-closed position, and a closed position. When latching mechanism 180 is in its open position, as also outlined above, projections 111 can be inserted into and/or removed from slots 115. When latching mechanism 180 is in its partially-closed position, referring to FIG. 6, latch arms 188 can be configured to engage latch projections 131 such that projections 111 cannot be removed from slots 115. In at least one such embodiment, latch arms 188 and latch projections 131 can be configured to prevent, or at least inhibit, second handle portion 104 from being moved distally with respect to first handle portion 102 and, as a result, prevent, or at least inhibit, projections 111 from being disengaged from slots 115. Correspondingly, latch arms 188 and latch projections 131 can be configured to prevent first handle portion 102 from being moved proximally with respect to second handle portion 104. Similar to the above, in various embodiments, latch arms 188 and latch projections 131 can also be configured to prevent, or at least inhibit, projections 111 from being removed from slots 115 when latching mechanism 180 is in its closed position (FIG. 7). In certain embodiments, further to the above, latch projections 131 can extend from second handle portion 104 at a location which is intermediate its proximal and distal ends. In at least one such embodiment, projections 111 and slots 115 can be configured to hold the first and second handle portions together at their proximal ends while latching mechanism 180 can be utilized to hold the first and second handle portions together at an intermediate location. In any event, in certain embodiments, the first and second handle portions cannot be disengaged from one another unless latching mechanism 180 is moved into its fully open position. In at least one such embodiment, projections 111 and slots 115 cannot be disengaged from one another when latching mechanism 180 is in a closed and/or partially-closed position.

Once anvil 130 and staple cartridge 150 have been sufficiently positioned, the tissue positioned intermediate anvil 130 and staple cartridge 150 can be stapled and/or incised. In various embodiments, referring to FIG. 3, surgical stapling instrument 100 can further include pusher bar assembly 200 which can be configured to advance and/or retract staple sled assembly 160 within staple cartridge 150, for example. In at least one embodiment, pusher bar assembly 200 can include pusher bar 202 and firing actuator 204, wherein firing actuator 204 can be configured to move pusher bar 202 and staple sled assembly 160 distally to deploy staples from staple cartridge 150 and deform the staples against anvil 130 as described above. In at least one embodiment, referring to FIGS. 11 and 12, staple sled 162 can include a groove, channel, or slot 161 which can be configured to receive, and can be operably connected to, a distal end 201 (FIG. 3) of pusher bar 202. In certain embodiments, staple sled assembly 160 can be operably engaged with pusher bar 202 when staple cartridge 150 is inserted into staple cartridge channel 122. In at least one embodiment, distal end 201 and slot 161 can include cooperating features which can allow distal end 201 and slot 161 to be assembled in a transverse direction but prevent, or at least inhibit, distal end 201 and slot 161 from being disassembled from one another in a proximal direction and/or distal direction. In other embodiments, pusher bar 202 can be advanced distally before contacting and engaging staple sled assembly 160. In at least one such embodiment, the staple sled assembly 160 can remain stationary until contacted by pusher bar 202. In any event, as outlined above, actuator 204 can be operably connected to pusher bar 202 such that a pushing and/or pulling force can be applied to actuator 204 and transmitted to pusher bar 202. In certain embodiments, as described in greater detail below, actuator 204 can be pivotably connected to a proximal end 203 of pusher bar 202 such that actuator 204 can be selectively rotated between at least first and second positions.

Figure 13:
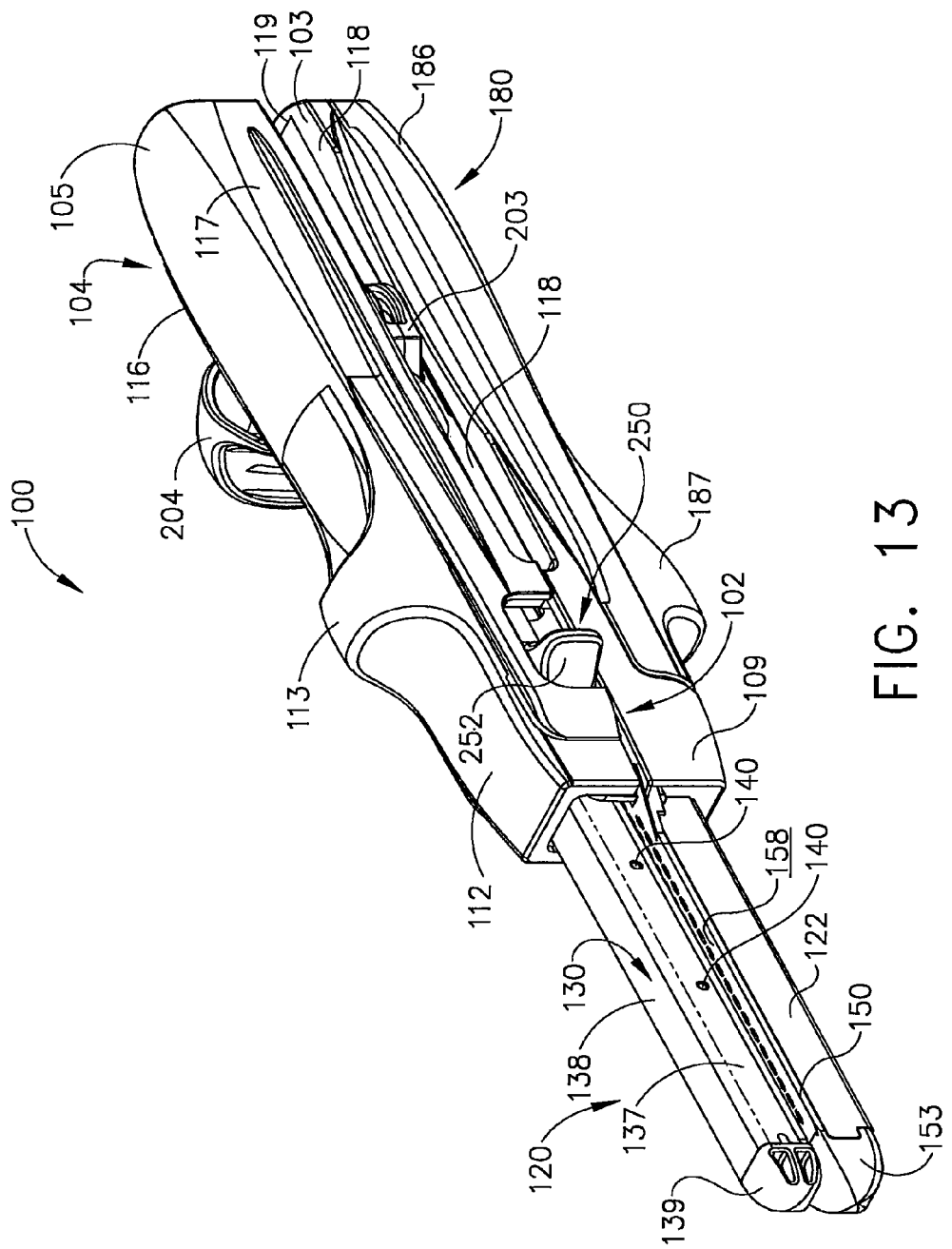
FIG. 13 is a perspective view of the surgical stapling instrument of FIG. 1 illustrating a firing actuator moved distally along a first side of the surgical stapling instrument.
Figure 14:
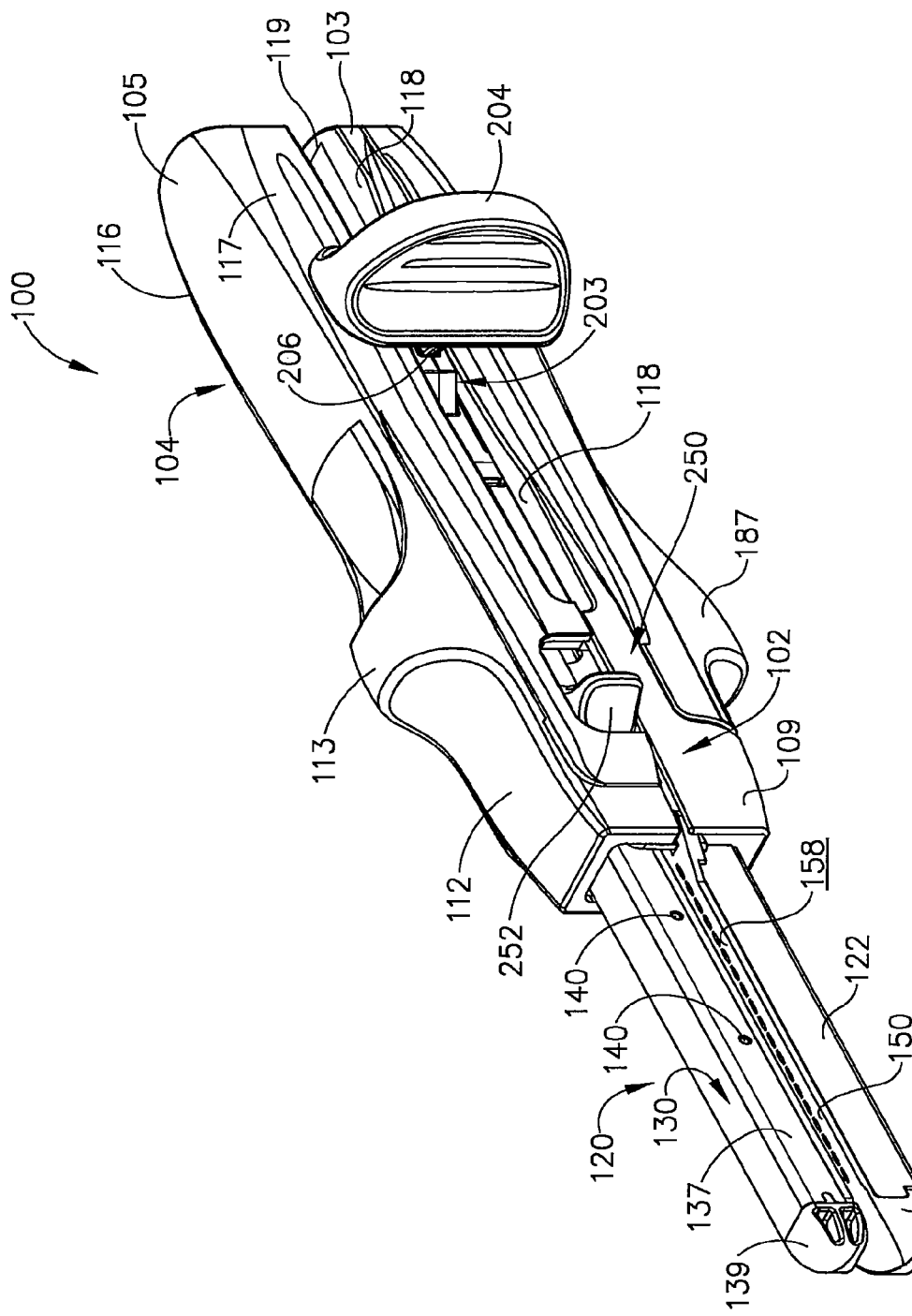
FIG. 14 is a perspective view of the surgical stapling instrument of FIG. 1 illustrating the firing actuator of FIG. 13 moved distally along a second side of the surgical stapling instrument.

Further to the above, referring to FIGS. 1, 13, and 14, actuator 204 can be movable between a first position on a first side 116 of surgical stapling instrument 100 (FIG. 13), a second position on a second side 117 (FIG. 14), and an intermediate position (FIG. 1) located at the proximal ends 103 and 105 of the first and second handle portions 102 and 104. Once actuator 204 has been rotated into position on one of the first and second sides 116, 117, actuator 204 can be advanced distally. In various circumstances, as a result, a surgeon may select whether to move actuator 204 distally along first side 116 or second side 117. Such circumstances may arise when it is more likely that actuator 204 may impinge on tissue surrounding the surgical site, for example, when actuator 204 is moved distally along one side of the surgical instrument as compared to the other. In various embodiments, referring to FIGS. 2 and 3, actuator 204 can include arm 206 extending therefrom where arm 206 can be pivotably mounted to proximal end 203 of pusher bar 202. In certain embodiments, referring once again to FIGS. 1, 13, and 14, surgical instrument 100 can include a first slot (not illustrated) extending along first side 116 and a second slot 118 extending along second side 117, wherein the first and second slots can be configured to slidably receive at least a portion of actuator 204. In at least one embodiment, the sidewalls of the first and second slots can confine, or at least assist in confining, the movement of actuator 204 such that it can be moved along a predetermined path. Referring to FIG. 14, second slot 118, for example, can be defined between first handle portion 102 and second handle portion 104 such that, when actuator 204 is moved distally along second side 117, arm 206 of actuator 204 can be slid intermediate the first and second handle portions. Similar to the above, the first slot can also be defined intermediate the first and second handle portions. In various embodiments, referring again to FIGS. 13 and 14, surgical instrument 100 can further include intermediate slot 119 which can also be configured to allow arm 206, and/or any other suitable portion of actuator 204, to slide therein. In at least one such embodiment, intermediate slot 119 can connect the first and second slots such that, when actuator 204 is positioned in its intermediate position, actuator 204 can be moved into either one of its first and second positions. In certain embodiments, the first slot, second slot 117, and intermediate slot 119 can be parallel, or at least substantially parallel, to one another and/or lie in the same plane, although other embodiments are envisioned in which one or more of the slots is not parallel to the others and/or lies in a different plane. Furthermore, although the first and second sides of the illustrated embodiment are located on opposite sides of surgical instrument 100, other embodiments are envisioned where the first and second slots, for example, are located on adjacent sides and/or sides which are not directly opposite to each other. Furthermore, other embodiments are envisioned in which the sides of a stapling instrument are not readily discernable, such as instruments having round and/or arcuate portions.

In various embodiments, further to the above, surgical stapling instrument 100 can further include a locking mechanism which can prevent, or at least inhibit, actuator 204 and, correspondingly, staple sled assembly 160, from being advanced prematurely. In at least one embodiment, the locking mechanism can be configured to prevent, or at least inhibit, actuator 204 from being advanced distally prior to latching mechanism 180 being moved into a closed, or an at least partially-closed, position. In certain embodiments, generally referring to FIG. 5, surgical stapling instrument 100 can further including locking mechanism 220 which can be engaged with actuator 204 and can remain engaged with actuator 204 while latching mechanism 180 is in a fully open position (FIG. 5) and/or an at least substantially-open position. In various embodiments, locking mechanism 220 can include lock 222 which can be biased into engagement with actuator 204 by a biasing force applied thereto by lock spring 224, for example. In at least one such embodiment, actuator 204 can include one or more grooves, channels, or slots (not illustrated) which can be configured to receive at least a portion of lock 222. In use, locking mechanism 220 can hold actuator 204 in position until latching mechanism 180 is moved into its fully closed position (FIG. 7) and/or an at least substantially closed position. In such circumstances, in at least one embodiment, latching mechanism 180 can be configured to engage locking mechanism 220 and disengage lock 222 from actuator 204. In at least one such embodiment, referring to FIGS. 5-7, latching mechanism 180 can further include cam 183 which can be configured to engage cam surface 223 on lock 222 when latching mechanism 180 is moved into its closed position and, as a result, slide, and/or otherwise move, lock 222 away from actuator 204. In various embodiments, cam 183 can comprise a wall, rib, and/or ridge extending from latch cover 186 and/or latch frame 184. In any event, once lock 222 has been sufficiently disengaged from actuator 204, in at least one embodiment, actuator 204 can be moved from its intermediate position, illustrated in FIG. 1, into one of its first and second positions, as illustrated in FIGS. 13 and 14.

Figure 15:
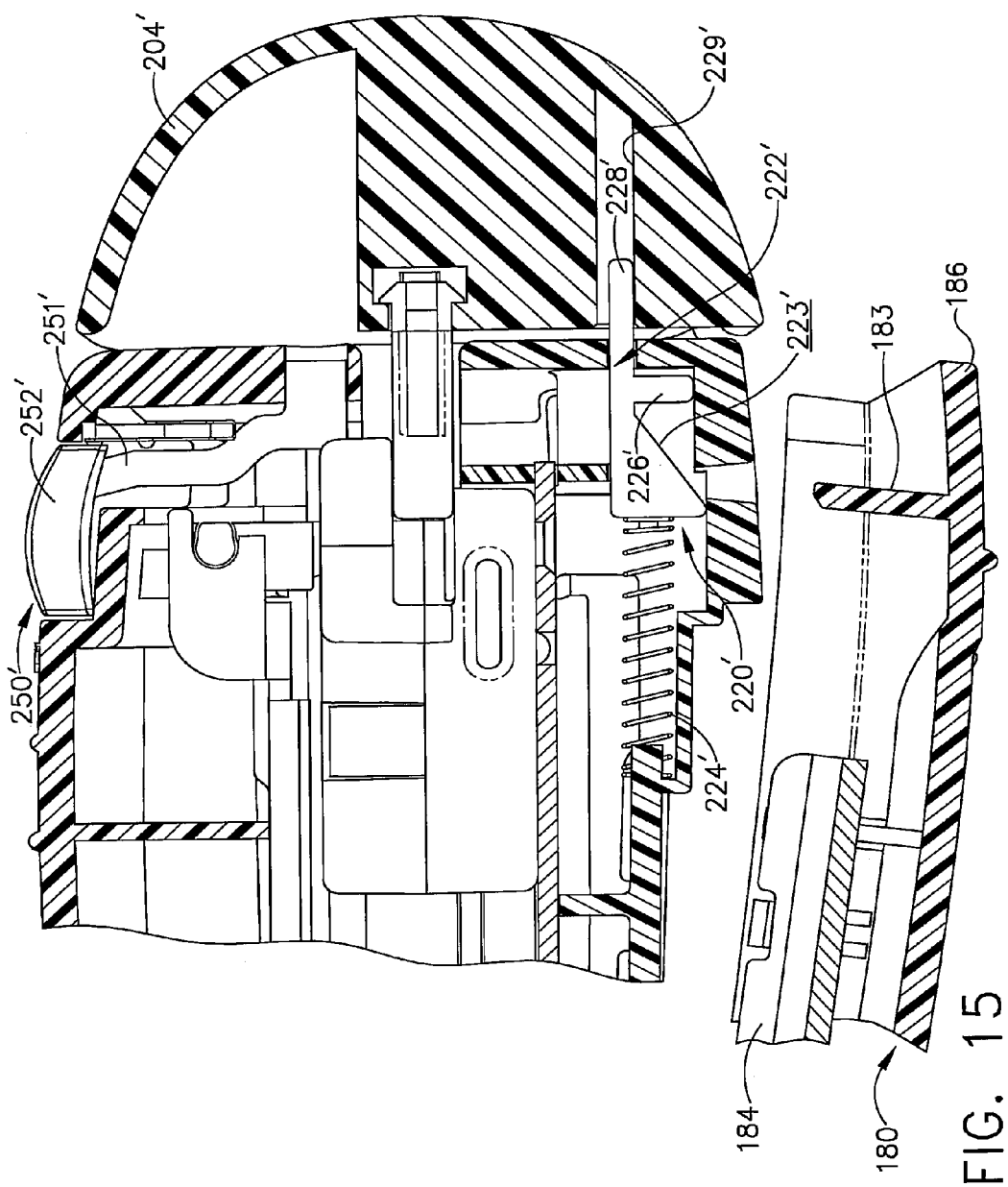
FIG. 15 is a cross-sectional view of a surgical stapling instrument in accordance with at least one alternative embodiment of the present invention illustrating a latch in a partially-closed position and a locking mechanism engaged with a firing actuator.
Figure 16:
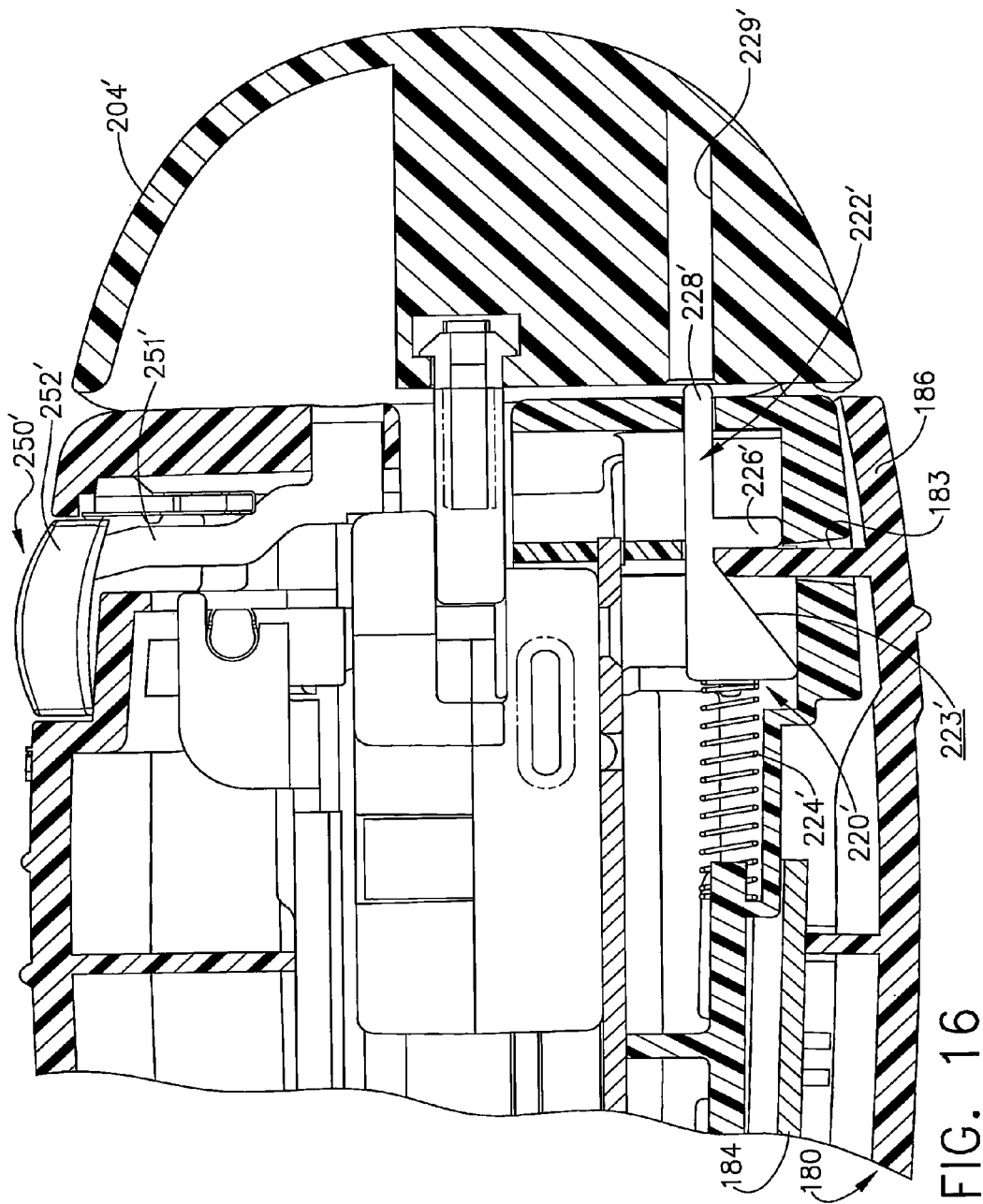
FIG. 16 is a cross-sectional view of the surgical stapling instrument of FIG. 15 wherein the latch has been moved into a closed position and has disengaged the locking mechanism from the firing actuator.

As described above, locking mechanism 220 can be configured to prevent, or at least inhibit, drive bar 202 from being advanced distally prior to latching mechanism 180 being moved into a predetermined position, such as, for example, a closed position and/or partially-closed position. Advantageously, locking mechanism 220 may also prevent, or at least inhibit, staple sled assembly 160 from being advanced prior to the first handle portion 102 and the second handle portion 104 being assembled together. In effect, locking mechanism 220 can prevent tissue positioned intermediate anvil 130 and staple cartridge 150 from being cut and/or stapled prior to anvil 130 and staple cartridge 150 being properly positioned relative to the tissue. Also, in effect, locking mechanism 220 can prevent staples from being deployed into the tissue prior to an appropriate clamping force being applied to the tissue. In any event, when latching mechanism 180 is returned to its fully open position, and/or a partially-open position, cam 183 can be moved away from lock 222 such that lock spring 124 can bias lock 222 into engagement with actuator 204 once again. In various other embodiments, referring to FIGS. 15 and 16, locking mechanism 220' can include a lock 222' comprising a cam surface 223' and, in addition, a stop 226' which can limit the relative movement of lock 222'. In at least one embodiment, cam 183, for example, can be configured to contact cam surface 223' and, owing to the contoured, beveled, and/or angled surface of cam surface 223', cam 183 can be configured to drive lock 222' distally as illustrated in FIG. 16. Lock 222' can be driven distally such that pin 228', which extends from lock 222', can be moved between a first position (FIG. 15) in which it is positioned within aperture 229' in actuator 204' and a second position (FIG. 16) in which pin 228' has been sufficiently removed from aperture 229'. In various embodiments, stop 226' can be configured such that, as lock 222' is driven distally, stop 226' can come into contact with cam 183 once lock 222' has been sufficiently displaced. In such embodiments, stop 226' can be configured to control the second, or displaced, position of lock 222'. Similar to the above, as actuator 180 is moved out of its closed position and cam 183 is disengaged from locking mechanism 220', lock spring 224' can move lock 222' into engagement with actuator 204' once again.

In various embodiments, as described above, a firing actuator can be utilized to move a pusher bar, staple sled, and/or cutting member between first and second positions. As also described above, pusher bar assembly 200, for example, can be utilized to move a staple sled assembly, such as staple sled assembly 160, for example, between a proximal position (FIG. 10) and a distal position. In certain embodiments, a staple cartridge, such as staple cartridge 150, for example, can include a staple sled assembly 160 contained therein, wherein staple sled assembly 160 can be positioned in a distal position, as illustrated in FIG. 10, when the staple cartridge is assembled to or inserted into staple cartridge channel 122. In at least one such embodiment, referring to FIGS. 8-10, staple cartridge 150 can include further housing 170 which can be configured to cover at least a portion of cutting member 164 when staple sled assembly 160 is in its distal position, for example. In various embodiments, housing 170 can be configured to protect a surgeon, for example, when handling the staple cartridge, when inserting the staple cartridge into the surgical stapler, and/or assembling two or more portions of the surgical stapler together, for example. In at least one such embodiment, at least an upper portion of cutting edge 165 can extend above deck, or top surface, 158 of staple cartridge 150 and, absent a protective housing, such as housing 170, for example, the upper portion of cutting edge 165 may be exposed.

In various embodiments, as described above, cutting member 165 can be at least partially positioned within slot; or channel, 156 and, as illustrated in FIG. 10, at least the upper, or top, portion of cutting member 164 can extend above deck 158. In at least one embodiment, referring to FIGS. 8-10, housing 170 can include a first wall, or portion, 172 extending from a first portion 157 of staple cartridge body 152, a second wall, or portion, 174 extending from a second portion 159 of staple cartridge body 152, and a top wall, or portion, 176 extending between first wall 172 and second wall 174. In certain embodiments, a housing may comprise only one support wall, or support portion, extending from a staple cartridge body and, in addition, a top wall, or top portion, extending therefrom. In other embodiments, a housing may comprise one or more side walls, or portions, and no top wall. In at least one such embodiment, the side walls of the housing can be configured such that they extend above the top of the cutting member, or at least extend above a cutting edge of the cutting member, for example. In any event, as illustrated in FIG. 10, at least a portion of cutting member 164 can be positioned underneath top wall 176 and/or between side walls 172 and 174 when staple sled assembly 160 is in its proximal position. In certain embodiments, cutting member 164 can be entirely positioned underneath top wall 176, and/or entirely positioned within housing 170. In at least one embodiment, cutting member 164 can be positioned underneath top wall 176 such that cutting surface 165 does not extend beyond the distal edge 175 and/or the proximal edge 177 of top wall 176. In at least one embodiment, housing 170 can include a rear wall 178 which can be configured to limit the proximal movement of cutting member 164 and/or any other portion of staple sled assembly 160. In various embodiments, at least a portion of housing 170, for example, can be integrally-formed with staple cartridge body 152. In at least one such embodiment, first wall 172, second wall 174, top wall 176, and/or rear wall 178 can be formed when staple cartridge body 152 is injection molded, for example. In certain embodiments, at least a portion of housing 170 can be assembled to staple cartridge body 152 via a snap-fit arrangement, press-fit arrangement, and/or any other suitable manner.

In various embodiments, further to the above, cutting member 164 can be defined by a planar, or an at least substantially planar, body having a knife edge extending along at least one side of the cutting member body. In at least one such embodiment, first wall 172 and/or second wall 174 can be configured and arranged such that they can include planar, or at least substantially planar, interior surfaces 173 which are parallel, or at least substantially parallel, to the side surfaces of cutting member 164. In certain embodiments, cutting member 164 can be closely received between the interior surfaces 173 of walls 172 and 174. In at least one such embodiment, the distance between walls 172 and 174 may be the same as, or at least substantially the same as, the width of slot 156. In any event, a housing can be configured such that at least a portion of the housing extends over at least a portion of slot 156, for example. In certain embodiments, housing 170 can completely enclose or surround a cutting member 164 and/or cutting surface 165. In at least one embodiment, although not illustrated, a housing can include a break-away and/or incisable portion which can be at least partially detached, separated, and/or otherwise deformed in order to permit a cutting member to exit the housing. In at least one such embodiment, the tissue cutting surface can be configured to contact the housing to break and/or incise a housing wall, for example. In various embodiments, the housing wall can include a thin portion, a reduced-thickness portion, score mark, and/or any other configuration to facilitate the deformation and/or incision of the housing wall. In certain embodiments, a cutting member can include one or more additional cutting surfaces and/or anvils, for example, which can be configured to deform and/or incise the housing. In at least one embodiment, the housing can include a movable and/or flexible portion, such as a hinged member and/or flexible flap, for example, which can be configured to sufficiently move and/or flex to allow the cutting member to pass thereby. In any event, embodiments are envisioned in which the cutting member can have any suitable configuration for incising tissue and the protective housing can have any suitable configuration for at least partially enclosing or surrounding the cutting member. Furthermore, although a cutting member can comprise a sharpened edge as described above, other suitable cutting members are envisioned, such as those supplied with an electrical current sufficient to dissect tissue, for example.

As described above, housing 170 can be configured to at least partially cover, enclose, and/or surround a cutting member when it is in its proximal position. In various embodiments, the cutting member can be advanced distally to incise tissue, for example, and then retracted proximally in order to position the cutting member within housing 170 once again. In such embodiments, the cutting member can be at least partially covered by housing 170 when the staple cartridge is assembled to and removed from a surgical stapling instrument. In certain embodiments, a new, or unspent, staple cartridge can be inserted into the staple cartridge channel to replace the at least partially spent staple cartridge. In at least one such embodiment, the new staple cartridge can include a new cutting member and/or staple sled assembly positioned therein, although embodiments are envisioned in which the previously-used cutting member and/or staple sled assembly can be sufficiently withdrawn from the spent staple cartridge and advanced into the new staple cartridge in order to be reused once again. In embodiments where a new cutting member and/or staple sled assembly is provided with each new staple cartridge, a sharp cutting edge, for example, can be utilized with each staple cartridge.

In various embodiments, although not illustrated, a staple cartridge can include two or more housings configured to at least partially cover a cutting member when it is in two or more positions. In at least one embodiment, a staple cartridge can include a proximal housing configured to at least partially cover the cutting member when it is in a proximal position, for example, and, in addition, a distal housing configured to at least partially cover the cutting member when it is in a distal position, for example. In at least one such embodiment, the cutting member can be positioned within the proximal housing when the staple cartridge is assembled to a surgical stapling instrument and, in certain embodiments, the cutting member can be advanced into the distal housing after it has transected tissue positioned within the end-effector, for example. In such embodiments, as a result, the cutting member can be at least partially positioned within the distal housing when the staple cartridge is removed from the surgical stapler. Such embodiments may be particularly useful when a vessel, for example, is positioned intermediate the proximal housing and the distal housing of the staple cartridge. In various embodiments, although not illustrated, a cutting member can be moved proximally from a distal position to a proximal position, and/or any other suitable position.

Figure 17:
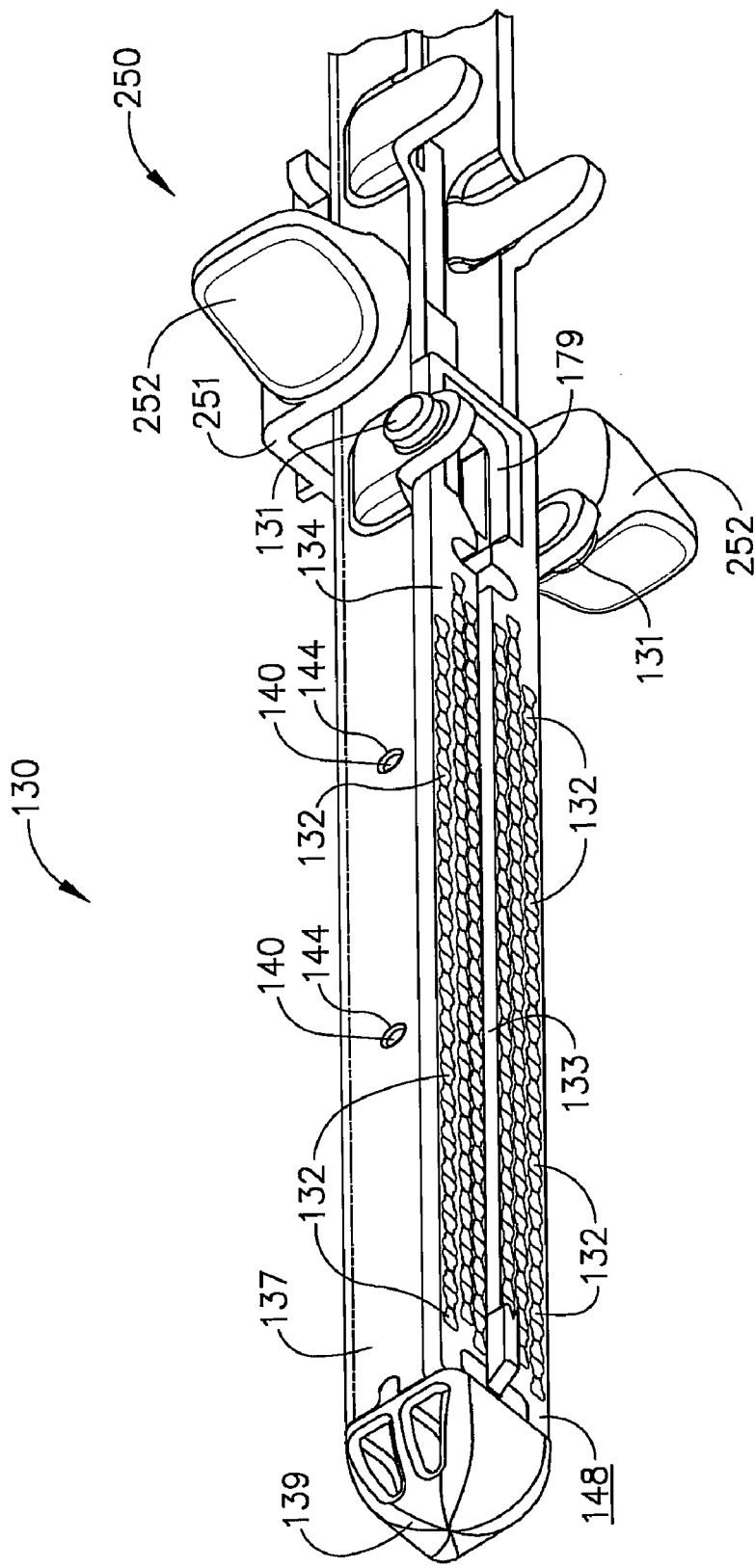
FIG. 17 is a perspective view of an anvil assembly of the surgical stapling instrument of FIG. 1.

In various embodiments, further to the above, anvil 130 can include one or more apertures, slots, or recesses 179 (FIG. 17) which can be configured to receive at least a portion of housing 170 when anvil 130 is brought into close opposition to staple cartridge 150, for example. In at least one embodiment, sufficient clearance can be present between housing 170 and recess 179 such that anvil 130 and staple cartridge 150 can be moved relative to each other without interference, or at least substantial interference, therebetween. In embodiments having more than one cutting member housing as outlined above, an opposing anvil can have more than one corresponding aperture for receiving the housings. In various embodiments, an anvil can include a movable cutting member and at least one housing for at least partially covering, enclosing, and/or surrounding the cutting member. In certain embodiments, although not illustrated, both an anvil and a staple cartridge can comprise at least one movable cutting member and/or at least one housing configured to at least partially cover, surround, or enclose the cutting members when they are in a proximal position, for example.

Figure 18:
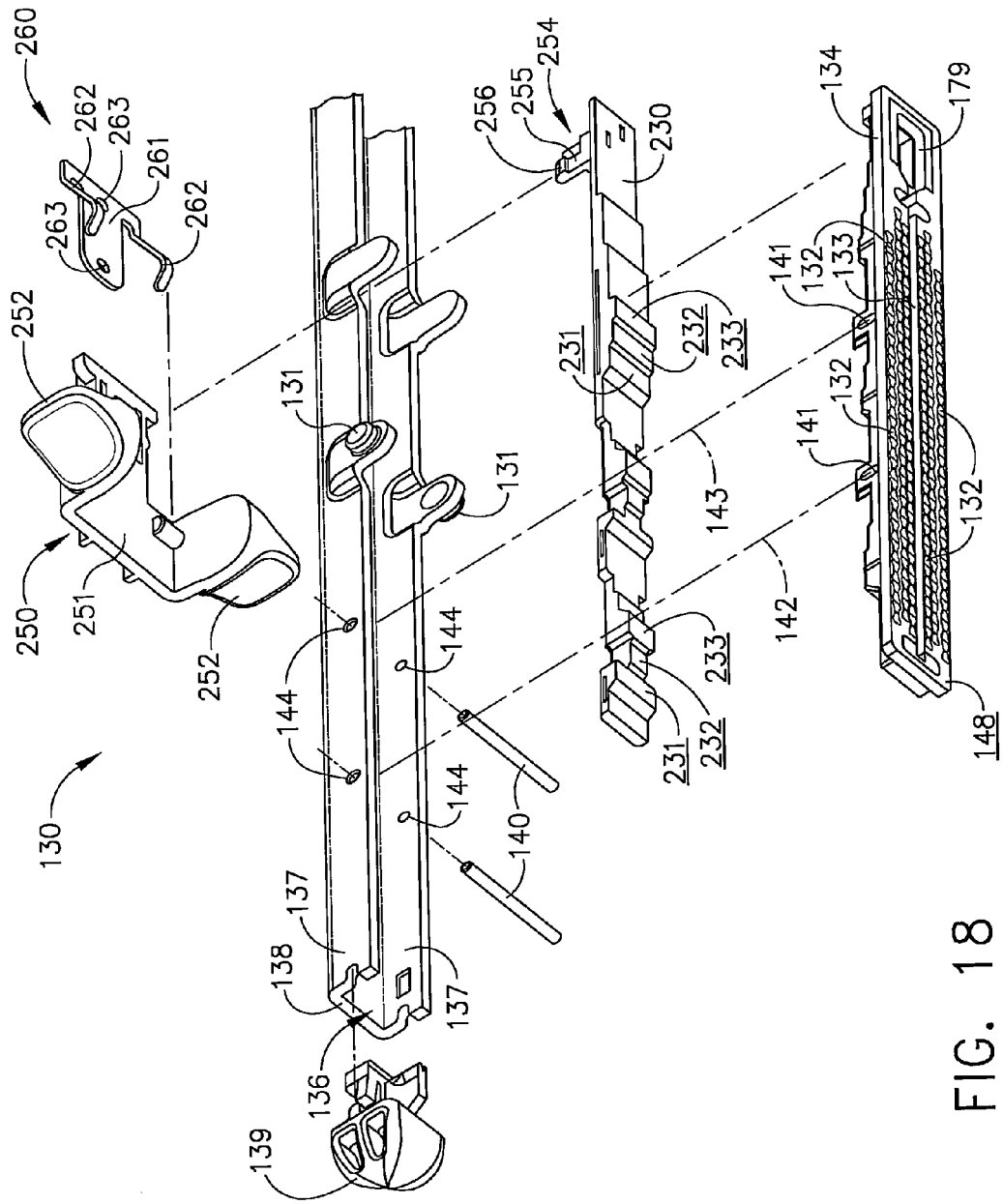
FIG. 18 is an exploded perspective view of the anvil assembly of FIG. 17.
Figure 19:
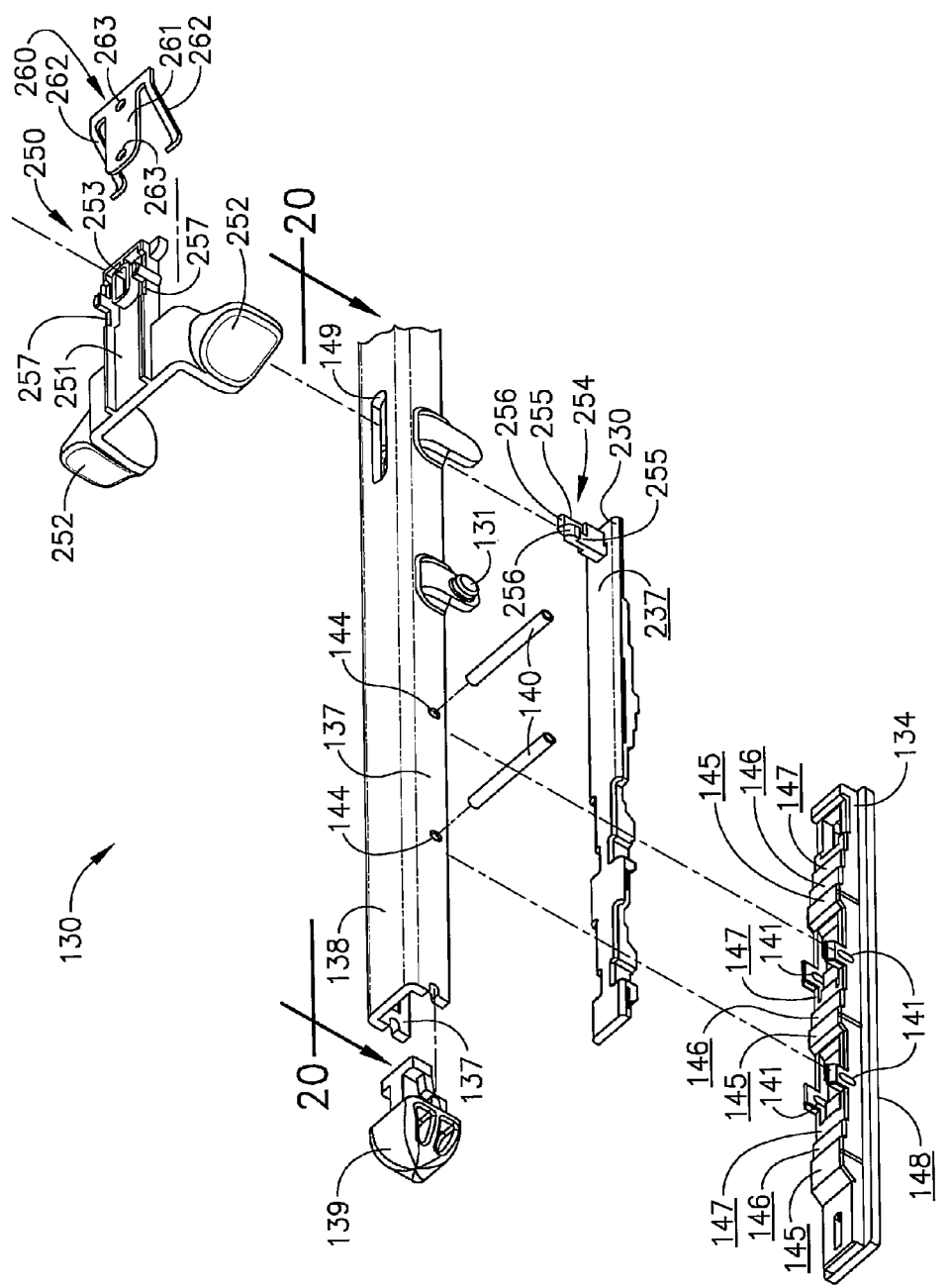
FIG. 19 is another exploded perspective view of the anvil assembly of FIG. 17.
Figure 24:
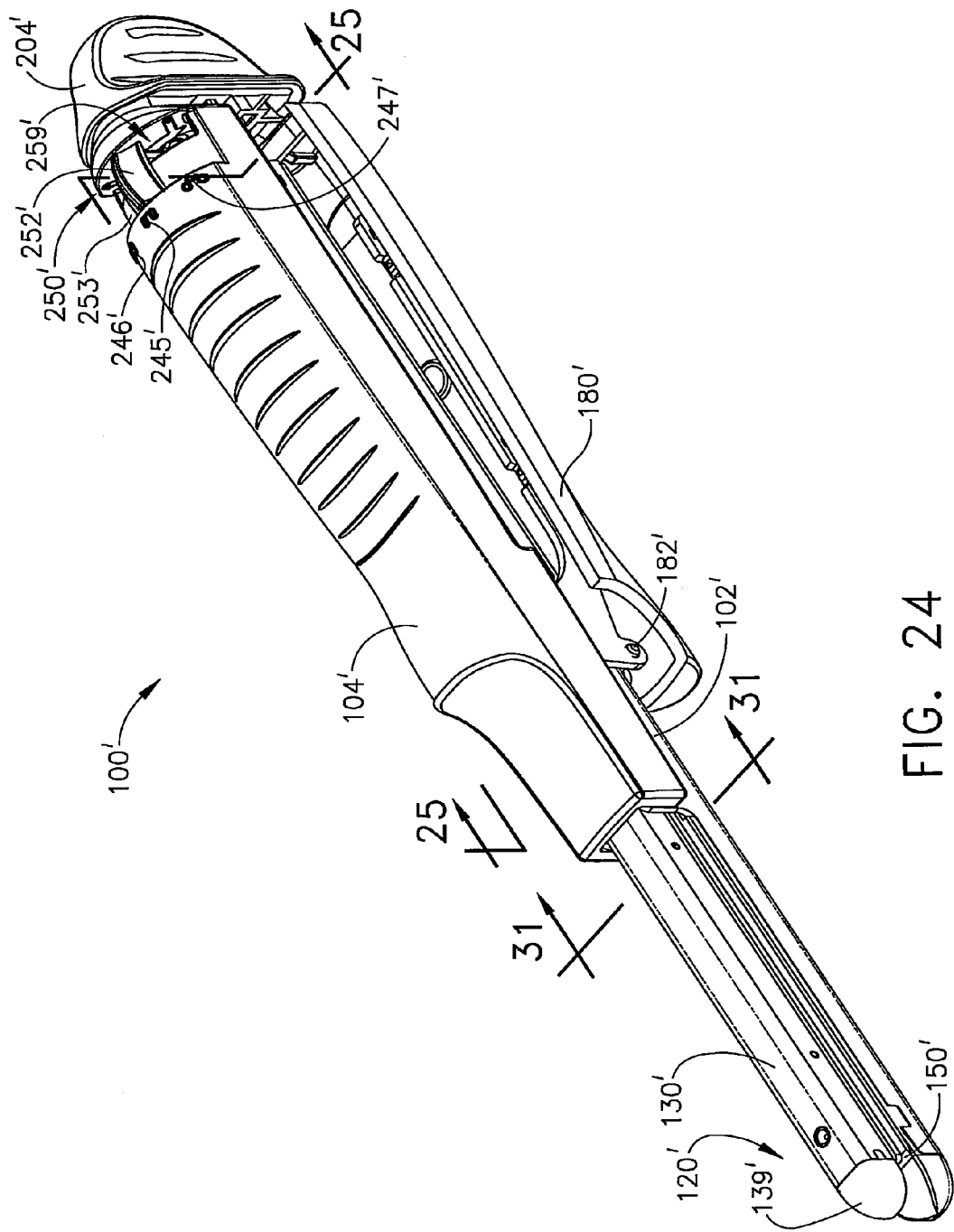
FIG. 24 is a perspective view of a surgical stapling instrument in accordance with at least one alternative embodiment of the present invention.
Figure 28:
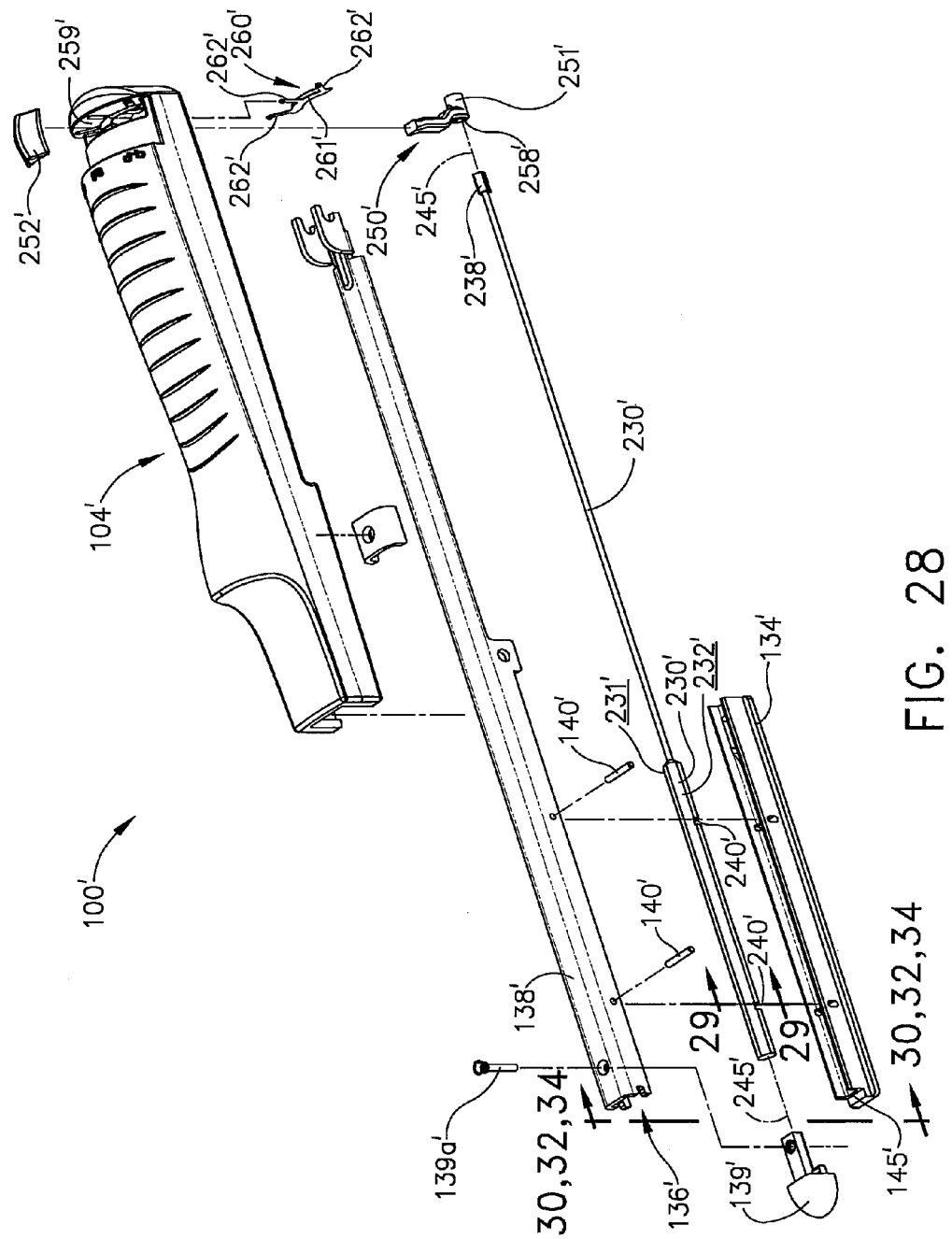
FIG. 28 is an exploded view of portions of the surgical stapling instrument of FIG. 24 illustrating a rotatable anvil adjustment member in a first orientation.
Figure 29:
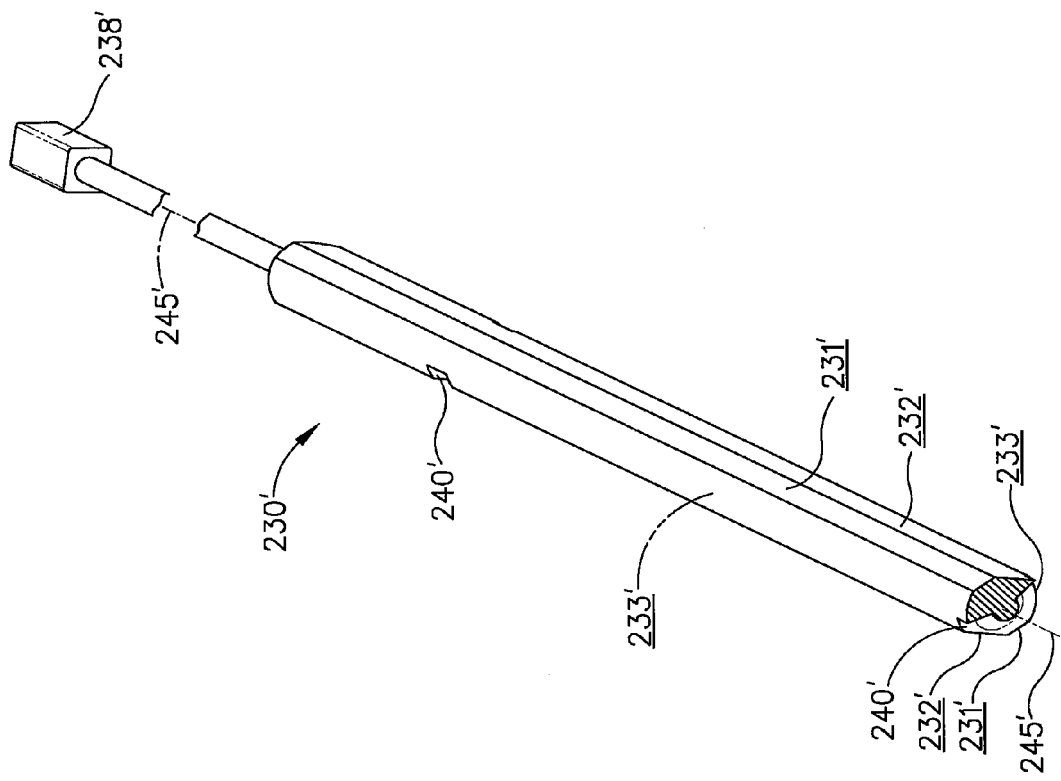
FIG. 29 is a perspective view of the rotatable anvil adjustment member of FIG. 28.

As outlined above, pusher bar assembly 200 can be advanced distally in order to move staple sled assembly 160 within staple cartridge assembly 150. In various embodiments, as also outlined above, the wedge-like cam surfaces 167 of staple sled 162 can be moved into engagement with the sloped surfaces 169 on staple drivers 168 to sequentially, and/or simultaneously, drive staples from staple cartridge 150 against anvil 130 and form the staples into any suitable configuration, such as B-shaped configurations, for example. In at least one such embodiment, referring to FIG. 17, anvil 130 can include one or more staple forming surfaces, such as staple pockets 132, for example, which can be configured to deform the staples. In certain embodiments, anvil 130 can further include a slot, channel, or groove 133 which can be configured to slidably receive at least a portion of staple sled 162, cutting member 164, and/or pusher bar 202, for example. In at least one embodiment, although not illustrated, an anvil can include an anvil plate which can be securely and/or immovably positioned within an anvil channel defined within the anvil. In various other embodiments, as illustrated in FIGS. 18 and 19 and described in greater detail below, anvil 130 can include an anvil plate 134 movably positioned within anvil channel 136. In certain embodiments, anvil channel 136 can include opposite side walls 137 and, in addition, a base 138 extending between side walls 137. In at least one embodiment, anvil 130 can further include a distal nose portion 139, for example, assembled thereto wherein nose portion 139 can be configured to be press-fit and/or snap-fit into anvil channel 136, for example, such that nose portion 139 can be securely retained therein. In certain embodiments, nose portion 139 can be comprised of a soft and/or pliable material, such as rubber, for example, and can comprise any suitable shape which can facilitate the insertion of anvil 130 into a surgical site, for example. In some embodiments, referring to FIG. 28, a nose portion, such as nose portion 139' can be retained to an anvil by one or more fasteners 139a'. Similarly, referring to FIG. 1, a staple cartridge channel and/or staple cartridge, such as staple cartridge 150, for example, can include a nose portion, such as nose portion 153, for example, which can facilitate the insertion of staple cartridge 150 into a surgical site, for example As indicated above, staples can be deployed from a staple cartridge and deformed against an anvil. In various circumstances, the distance between the staple forming surfaces on anvil 130 and staple sled 162 can determine the amount in which the staples are deformed. For example, if the distance between anvil pockets 132 on anvil 130 and top surfaces 135 on staple sled 162 (FIGS. 10-12) is relatively large, the staples will be deformed a lesser amount as compared to when the distance between anvil pockets 132 and sled surfaces 135 is relatively small. Correspondingly, if the distance between anvil pockets 132 and sled surfaces 135 is relatively small, the staples will be deformed a greater amount as compared to when the distance between anvil pockets 132 and sled surfaces 135 is relatively large. Often, the distance between anvil pockets 132 and sled surfaces 135 is referred to as the forming height of the staples. Sometimes the forming height of the staples can be measured between the top surface, or deck, of the staple cartridge and the staple forming surfaces on the anvil. For the purpose of this application, however, any reference to a staple forming height, or the like, can include one or both manners of measurement, where appropriate, and/or any other suitable manner of measurement. In any event, as described in greater detail below, a surgical stapling instrument, such as stapling instrument 100, for example, can include means for adjusting the staple forming height.

In various embodiments, further to the above, an anvil can include one or more forming surfaces which can be moved toward and/or away from a staple cartridge in order to set the forming height of the staples. In at least one embodiment, referring to FIGS. 17-23, anvil 130 can include anvil plate 134 which can be movably and/or slidably positioned within anvil channel 136. In certain embodiments, anvil 130 can further include one or more retention, or guide, pins 140, wherein anvil plate 134 can include one or more retention, or guide, slots 141 configured to slidably receive at least a portion of pins 140. In at least one such embodiment, pins 140 and/or slots 141 can be configured to define a predetermined path along which anvil plate 134 can be moved. Referring to FIG. 18, pins 140 and slots 141 can be structured and arranged such that anvil plate 134 can be moved along a linear, or at least substantially linear, path, wherein the linear path can be at least partially defined by axes 142 and 143, for example. Other embodiments are envisioned in which an anvil plate can be moved along a non-linear path, such as a curved and/or curvi-linear path, for example. In certain embodiments, at least a portion of pins 140 can be retained within apertures 144 in side walls 137 wherein, in at least one embodiment, pins 140 can be press-fit within apertures 144. In any event, as described herein, pins 140 can guide anvil plate 134 as it is moved toward and/or away from staple cartridge 150, for example.

In various embodiments, further to the above, a surgical stapling instrument, such as stapling instrument 100, for example, can include one or more adjustment members configured to position a portion of an anvil, such as anvil plate 134, for example, relative to other portions of an anvil assembly and/or an opposing staple cartridge. In certain embodiments, referring to FIGS. 18 and 19, stapling instrument 100 can include anvil plate adjustment member 230 which can be configured to limit the range of motion of anvil plate 134. In at least one such embodiment, referring to FIGS. 20 and 21, adjusting member 230 can be positioned intermediate anvil plate 134 in a first position in which first surface, or step, 231 of adjusting member 230 is positioned intermediate base 138 of anvil channel 136 and first positioning surface 145 on anvil plate 134. In such a first position, first step 231 can define the amount of relative movement possible, or permitted, between anvil plate 134 and anvil channel 136. For example, when anvil 130 is clamped against tissue as described above, anvil plate 134 can contact the tissue and slide upwardly toward base 138 until first positioning surface 145 contacts first step 231. Once surface 145 and step 231 are in contact, adjusting member 230 can prevent, or at least inhibit, anvil plate 134 from moving further toward base 138. In at least one such embodiment, as a result, adjusting member 230 can act as a stop such that the distance between base 138 and tissue-contacting surface 148 on anvil plate 134 can be defined by a first distance 234. While base 138 is used as a reference datum in the present example, other portions of anvil 130 and/or an opposing staple cartridge, for example, could be used as reference datums. When adjusting member 230 is in its first position, as described above, second surface, or step, 232 of adjusting member 230 can be positioned intermediate base 138 and second positioning surface 146 on anvil plate 134, and, in addition, third surface, or step, 233 can be positioned intermediate base 138 and third positioning surface 147. Referring to FIG. 20, adjustment member 230 can include two or more sets of steps, 231, 232, and/or 233 and anvil plate 134 can include two or more sets of positioning surfaces 145, 146, and/or 147. While first step 231 and first positioning surface 145 are described above as being configured to control the position of anvil plate 134, the second and third steps (232, 233) of adjustment member 230 and the second and third positioning surfaces (146, 147) of anvil plate 134, respectively, can also be configured to control the position of anvil plate 134. For the sake of brevity, though, the present example will be described in reference to the first surface, or step 231, as being the surface which controls the position of anvil plate 134, although the reader will understand that the steps 232 and 233 can control the position of anvil plate 134 as well.

In certain embodiments, the first position of adjustment member 230 can provide for a relatively small, or short, staple forming height. In other embodiments, although not illustrated, the first position of an adjustment member can provide for an intermediate, a relatively large, and/or any other suitable staple forming height. In the event that the forming height associated with the first position of the adjustment member is suitable, a surgeon can proceed to use the surgical stapling instrument to staple and/or incise tissue as described above. In the event, however, that the staple forming height is unsuitable, a surgeon, or other clinician, can move adjustment member 230 such that adjustment member 230 can permit anvil plate 134 to slide upwardly a different distance when anvil plate 134 contacts tissue positioned intermediate anvil 130 and staple cartridge 150. In at least one such circumstance, the distance in which anvil plate 134 is permitted to slide upwardly can be larger, thereby providing a larger forming height for the staples. Correspondingly, in other circumstances, the adjustment member can be moved such that anvil plate 134 can slide upwardly a shorter distance when anvil plate 134 contacts the tissue, for example, thereby providing a shorter staple forming height. While the term "upward", and the like, can mean vertically upward, the term is not so limited; rather, "upward" can mean any direction which is toward the base of the anvil and/or away from a staple cartridge, for example. In any event, adjustment member 230 can be moved between its first position, illustrated in FIG. 21, and a second position, illustrated in FIG. 22, in order to increase the staple forming height. As indicated by arrow "P" in FIG. 22, adjustment member 230 can be slid proximally in order to move adjustment member 230 between its first and second positions, although embodiments are envisioned where an adjustment member can be slid distally and/or any other suitable direction in order to adjust adjustment member 230. Once adjustment member 230 has been moved into its second position, referring to FIG. 22, first surface, or step, 231 can be positioned intermediate base 138 and second positioning surface 146 of anvil plate 134. In such a second position, first step 231 can once again define the amount of relative movement permitted between anvil plate 134 and anvil channel 136. In at least one embodiment, similar to the above, adjusting member 230 can act as a stop such that the distance between base 138 and tissue-contacting surface 148 on anvil plate 134 can be defined by a second distance 235.

Further to the above, adjustment member 230 can be moved between its second position, illustrated in FIG. 22, and a third position, illustrated in FIG. 23, in order to once again increase the staple forming height. As indicated by arrow "P" in FIG. 23, adjustment member 230 can be slid proximally in order to move adjustment member 230 between its second and third positions. Once adjustment member 230 has been moved into its third position, referring to FIG. 23, first surface, or step, 231 can be positioned intermediate base 138 and third positioning surface 147. In such a third position, first step 231 can once again define the amount of relative movement between anvil plate 134 and anvil channel 136. In at least one embodiment, similar to the above, adjusting member 230 can act as a stop such that the distance between base 138 and tissue-contacting surface 148 on anvil plate 134 can be defined by a third distance 236. While adjustment member 230 can be selectively moved between three positions as described above to provide three different staple forming heights, other embodiments are envisioned which comprise an adjustment member which can be moved between more than three positions to provide more than three different staple forming heights. For example, an adjustment member can be movable between four positions in order to provide four staple forming heights. Further embodiments are envisioned which comprise an adjustment member which can be moved between two positions to provide two staple forming heights. Furthermore, while surfaces, or steps, 231, 232, and 233 of adjustment member 230 are arranged in a descending order, other arrangements are envisioned in which the surfaces, or steps, are arranged in an ascending order. Other arrangements are envisioned in which the surfaces, or steps, are not necessarily arranged in either an ascending or a descending order. Similarly, positioning surfaces 145, 146, and 147 of anvil plate 134 can be arranged in an ascending order, a descending order (FIG. 20), and/or any other suitable order. Furthermore, while adjustment member 230 can be slid along an axis, other embodiments are envisioned where an adjustment member can be moved along any suitable path such as curved and/or curvi-linear paths, for example.

As described above, referring to FIG. 21, adjustment member 230 can comprise three surfaces, or steps, 231, 232, and 233 while anvil plate 134 can comprise three corresponding adjustment surfaces 145, 146, and 147. When adjustment member 230 is in its first position, for example, first surface 231 can be positioned such that it abuts or is adjacent to first adjustment surface 145, second surface 232 can be positioned such that it abuts or is adjacent to second adjustment surface 146, and third surface 233 can be positioned such that it abuts or is adjacent to third adjustment surface 147. As adjustment member 230 is slid relative to anvil plate 134, as described above and referring to FIGS. 22 and 23, surfaces 231, 232, and 233 of adjustment member 230 can be sequentially indexed relative to surfaces 145, 146, and 147 of anvil plate 134. In at least one such embodiment, an adjustment member can have the same number of steps as the number of positioning surfaces on an anvil plate. Other embodiments are envisioned where an adjustment member has more steps than positioning surfaces on the anvil plate. In at least one such embodiment, an anvil plate can include one positioning surface wherein the steps of an adjustment member can be selectively utilized to limit the upward movement of the anvil plate, for example. In various embodiments, referring generally to adjustment member 230 and anvil plate 134, an anvil plate may include one positioning surface, such as positioning surface 145, for example, where steps 231, 232, and 233 of adjustment member 230, for example, can be selectively positioned intermediate base 138 and positioning surface 145. In such embodiments, first step 231 can have a first thickness or height which can stop, or limit, the upward movement of anvil plate 134 so as to define a first staple forming height, second step 232 can have a second thickness or height which can stop, or limit, the upward movement of anvil plate 134 so as to define a second staple forming height, and, in addition, third step 233 can have a third thickness or height which can stop, or limit, the upward movement of anvil plate 134 so as to define a third staple forming height. In at least one embodiment, the thickness or height of steps 231, 232, and/or 233 can be measured between a back surface 237 of adjustment member 230 and a surface on the steps (231, 232, 233) which will contact anvil plate 134. In various embodiments, the difference in height, or thickness, between first step 231 and second step 232 can be the same, or at least substantially the same, as the difference in height, or thickness, between second step 232 and third step 233. In at least one such embodiment, as a result, the step heights can increase at a linear rate, or an at least substantially linear rate. In alternative embodiments, the difference in height, or thickness, between the first and second steps can be different than the difference in height, or thickness, between the second and the third steps. In at least one such embodiment, the first, second, and third steps may not increase or decrease in height, or thickness, at a linear rate; rather, although not illustrated, the steps may increase or decrease in height, or thickness, in a non-linear and/or geometric rate.

As described above, an adjustment member, such as adjustment member 230, for example, can be movable between two or more positions. In various embodiments, a surgical stapling instrument can include an actuator configured to move the adjustment member. In at least one embodiment, referring to FIGS. 17-20, surgical stapling instrument 100 can include actuator 250 which can be operably attached to adjustment member 230 such that a force can be applied to actuator 250 and transmitted to adjustment member 230. In certain embodiments, actuator 250 can include grasping portions, or handles, 252 which can be configured to be grasped by a surgeon, for example, in order to advance or retract adjustment member 230 within anvil 130 as described above. In certain embodiments, grasping portions 252 can extend from actuator body 251, wherein actuator body 251 can include one or more apertures, slots, or cavities 253 which can be configured to receive at least a portion of adjustment member 230. In at least one such embodiment, referring to FIG. 19, adjustment member 230 can include lock 254 extending therefrom, wherein at least a portion of lock 254 can be received within aperture 253 so as to retain actuator body 251 to adjustment member 230. In various embodiments, lock 254 can include one or more resilient, or flexible, legs 255 which can be deflected when they are inserted into aperture 253 but resiliently return, or at least partially return, to their unflexed position after feet 256 of legs 255 are sufficiently pushed through aperture 253. In at least one such embodiment, feet 256 can prevent, or at least inhibit, actuator body 251 from being detached from adjustment member 230.

In various embodiments, further to the above, surgical stapling instrument 100 can further include a detent mechanism which can be configured to hold, or releasably hold, actuator 250 and/or adjustment member 230 in position. In at least one embodiment, referring to FIG. 19, detent member 260 can be attached to actuator 250 wherein, in at least some embodiments, actuator body 251 can include one or more channels, grooves, or recesses 257 which can be configured to receive and/or retain a detent body 261 of detent member 260 therein. In at least one embodiment, detent body 261 can include one or more apertures 263, and/or any other suitable channels, slots, or grooves, which can be configured to receive one or more fasteners for securing detent body 261 to actuator 251, for example. Detent member 260 can further include detent legs 262 which can be configured to engage one or more recesses, apertures, or grooves 101 (FIGS. 2-7) in first frame portion 110, for example. More particularly, referring to FIGS. 2 and 3, each side flange 128 can include one or more recesses 101 (101a, 101b, and 101c) defined therein wherein detent legs 262 can be biased into engagement with the top surfaces of side flanges 128 such that detent legs 262 can be slid into, and slid out of, recesses 101. In the illustrated embodiment, each side flange can include three recesses 101 which can be configured to removably hold actuator 250 in a first, distal position, a second, intermediate position, and a third, proximal position, wherein the first, second, and third positions of actuator 250 can respectively correspond with the first, second, and third positions of adjustment member 230 described above. For example, when actuator 250 is in its first, distal position, detent legs 262 of detent member 260 can be positioned within recess 101a so as to removably retain actuator 250 and adjustment member 230 in their first positions. Upon the application of a sufficient force, actuator 250 can be moved proximally into its second position such that detent legs 162 are positioned within recess 101b and actuator 250 and adjustment member 230 are retained in their second positions. Similarly, upon the application of a sufficient force, actuator 250 can be moved proximally into its third position such that detent legs 162 are positioned within recess 101c and actuator 250 and adjustment member 230 are retained in their third positions. In various embodiments, detent legs 162 can be configured such that actuator 250 can be returned to its first and/or second positions.

As described above, adjustment member 230 can be moved along a pre-determined path between two or more positions by actuator 250. In various embodiments, surgical stapling instrument 100, for example, can include one or more guides for controlling or limiting the movement of adjustment member 230 and/or actuator 250. In some embodiments, adjustment member 230 can be closely received between side walls 137 of anvil 130 such that side walls 137 can guide adjustment member 230. In at least one such embodiment, side walls 137 can be configured to control or limit the lateral or side-to-side movement of adjustment member 230. In various embodiments, detent legs 162 of detent member 160 can comprise resilient members which can be configured to apply an upward biasing or pulling force on adjustment member 230 so as to position adjustment member 230 against, or at least adjacent to, base 138 and intermediate side walls 137. In certain embodiments, referring to FIG. 19, base 138 of anvil 130 can further include guide slot 149 which can be configured to receive at least a portion of adjustment member 230 and/or actuator 250 therein such that guide slot 149 can limit the movement of adjustment member 230 and actuator 250. In at least one such embodiment, lock 254 of adjustment member 230 can be configured to extend through guide slot 149 such that, when lock 254 is inserted into aperture 253 of actuator 250 as described above, base 138 of anvil 130 can be captured intermediate adjustment member 230 and actuator 250. In certain embodiments, guide slot 149 can be configured to limit the movement of lock 254 such that adjustment member 230 can be prevented, or at least inhibited, from being moved distally when adjustment member 230 is in its first, or distal-most, position and/or, similarly, prevented, or at least inhibited, from being moved proximally when adjustment member 230 is in its third, or proximal-most, position.

Figure 37:
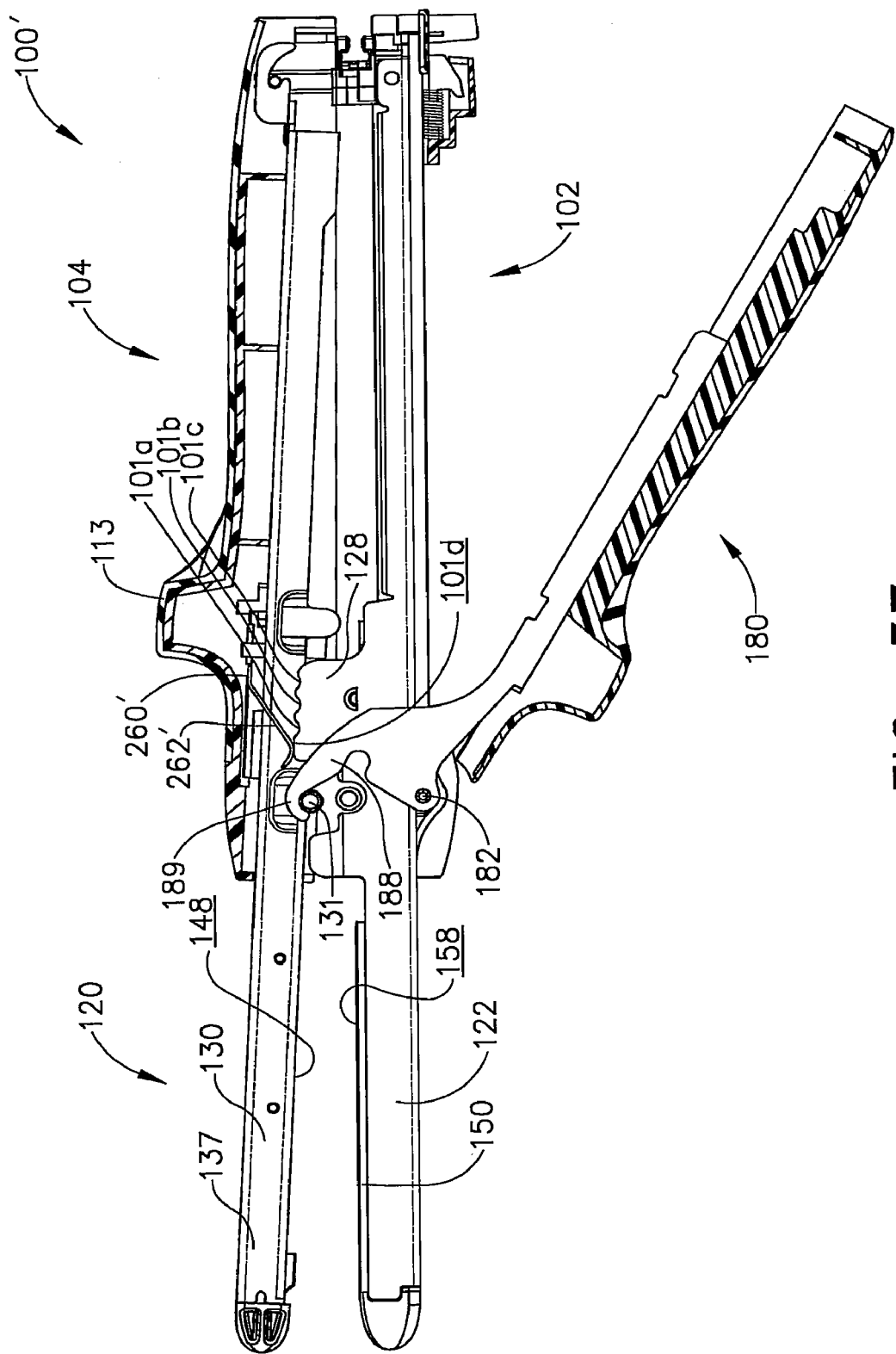
FIG. 37 is a partial cross-sectional view of a surgical stapling instrument including a spring configured to bias the distal end of a first handle portion away from the distal end of a second handle portion when the stapling instrument is in a partially-closed configuration.

In various embodiments, further to the above, a detent member, similar to detent member 260, for example, can be utilized to bias first handle portion 102 and second handle portion 104 away from one another. In at least one embodiment, referring to FIG. 37, surgical stapling instrument 100' can include a detent member 260' configured to position first handle portion 102 and second handle portion 104 such that a gap exists between anvil 130 and staple cartridge 150. Such a feature, as outlined above, can allow a surgeon to easily manipulate the surgical instrument without having to hold the first and second handle portions apart from one another. In certain embodiments, detent member 260' can be sufficiently mounted to second handle portion 104 such that detent legs 262' extending from detent member 260' can contact flanges 128 and, when compressed, apply a biasing force to the first and second handle portions. As seen in FIG. 37, legs 262' can contact surfaces 101d on flanges 128. In order to compress detent legs 262', latch mechanism 180 can be moved into a partially-closed position such that latch arms 188 can engage, and at least partially surround, latch projections 131. In this configuration, a surgeon can manipulate the instrument and, when satisfied with its position, move latch mechanism 180 into a closed position and further compress detent legs 262'. Similar to the above, detent member 260' can be affixed, or otherwise operably engaged with, actuator 250 such that, when actuator 250 is moved between its first, second, and third positions as described above, legs 262' can engage recesses 101a, 101b, and 101c, respectively. In at least one such embodiment, as a result, actuator 250 can have a pre-staged position in which actuator 250 is positioned distally with respect to its first position and, in addition, surfaces 101d can comprise pre-stage surfaces against which legs 262' can be positioned when actuator 250 is in its pre-staged position.

As outlined above, an adjustment member can be slid, or translated, between first and second positions so as to adjust the forming height of staples deployed by a surgical stapling instrument. In various embodiments, although not illustrated, an adjustment member can be configured to positively displace an anvil plate toward and/or away from an opposing staple cartridge, for example. In at least one such embodiment, a surgical stapling instrument can include one or more biasing members, such as springs, for example, configured to position the anvil plate against the adjustment member such that, when the adjustment member is moved between its first and second positions, the adjustment member can displace the anvil plate between first and second positions in order to set first and second staple forming heights. In various embodiments, as a result of the above, an adjustment member can be configured to cam a portion of an anvil into position. In at least one such embodiment, an adjustment member can be slid along an axis in order to positively displace an anvil plate. In other embodiments, a rotatable adjustment member can be configured to positively displace an anvil plate toward and/or away from a staple cartridge, for example.

Figure 25:
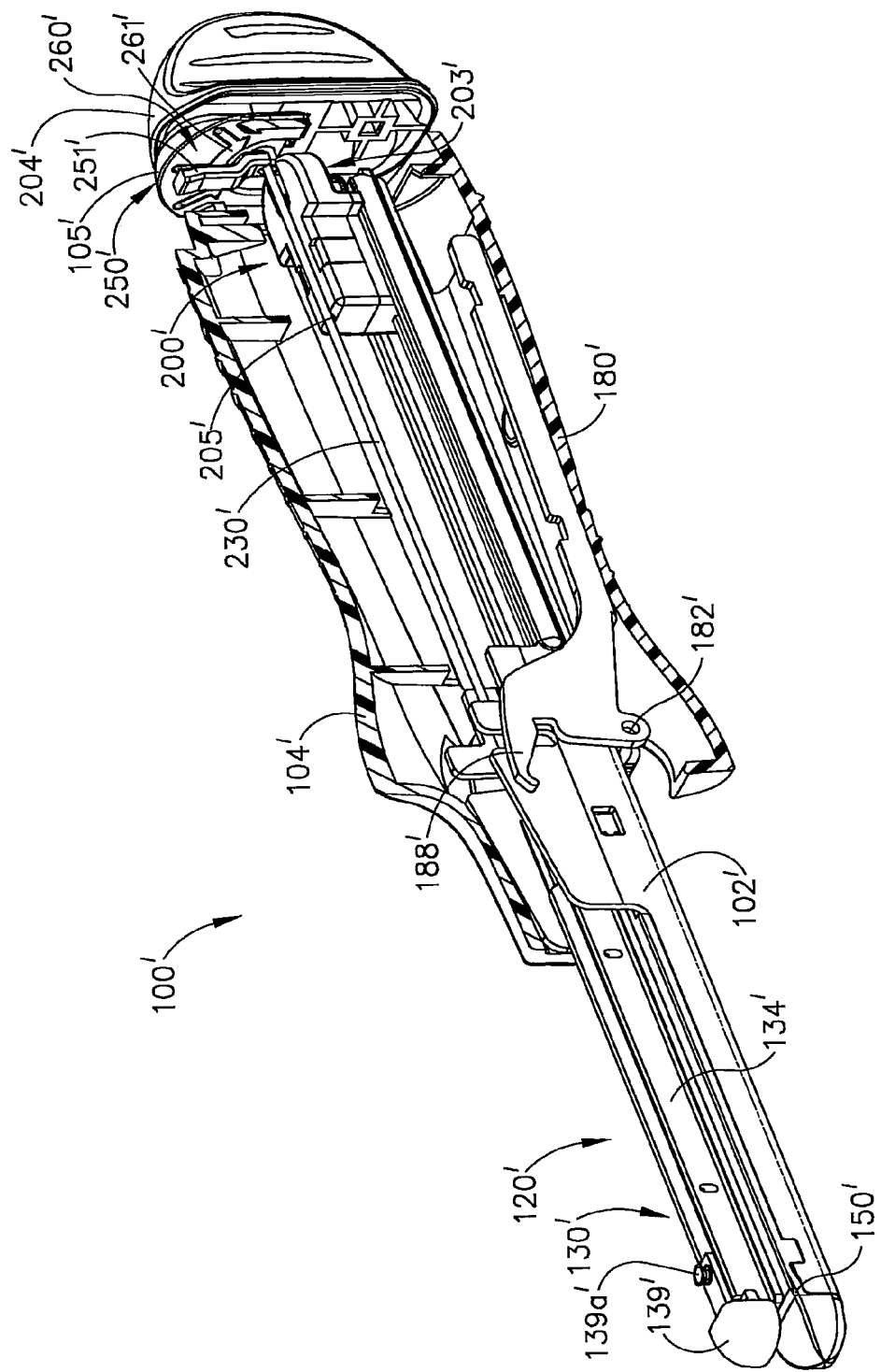
FIG. 25 is a cross-sectional view of the surgical stapling instrument of FIG. 24 taken along line 25-25 in FIG. 24.

Further to the above, as described in greater detail below, an adjustment member can be rotated to adjust the staple forming height. Referring to FIGS. 24-36, surgical instrument 100' can include, similar to the above, a first handle portion 102', a second handle portion 104', and a latching mechanism 180' which can be utilized to clamp tissue intermediate anvil 130' and staple cartridge 150'. Referring to FIG. 25, also similar to the above, latching mechanism 180' can be pivotably coupled to first portion 102' by one or more pivot pins 182', wherein latching mechanism 180' can include one or more latch arms 188' which can be configured to engage second portion 104' and latch the first and second handle portions together. Also similar to the above, referring to FIGS. 25 and 27, surgical instrument 100' can further include pusher bar assembly 200' which can be configured to advance a cutting member and/or staple sled within end-effector 120'. In at least one such embodiment, pusher bar assembly 200' can include a proximal end 203' and an actuator 204', wherein actuator 204' can be rotatably mounted to proximal end 203' and selectively positioned on first and second sides of stapling instrument 100'. In various embodiments, surgical stapling instrument 100' can comprise the same, or similar, features to those described in connection with surgical stapling instrument 100 and can be operated in the same manner, or a similar manner, as instrument 100 and, as a result, such details are not repeated herein.

Figure 27:
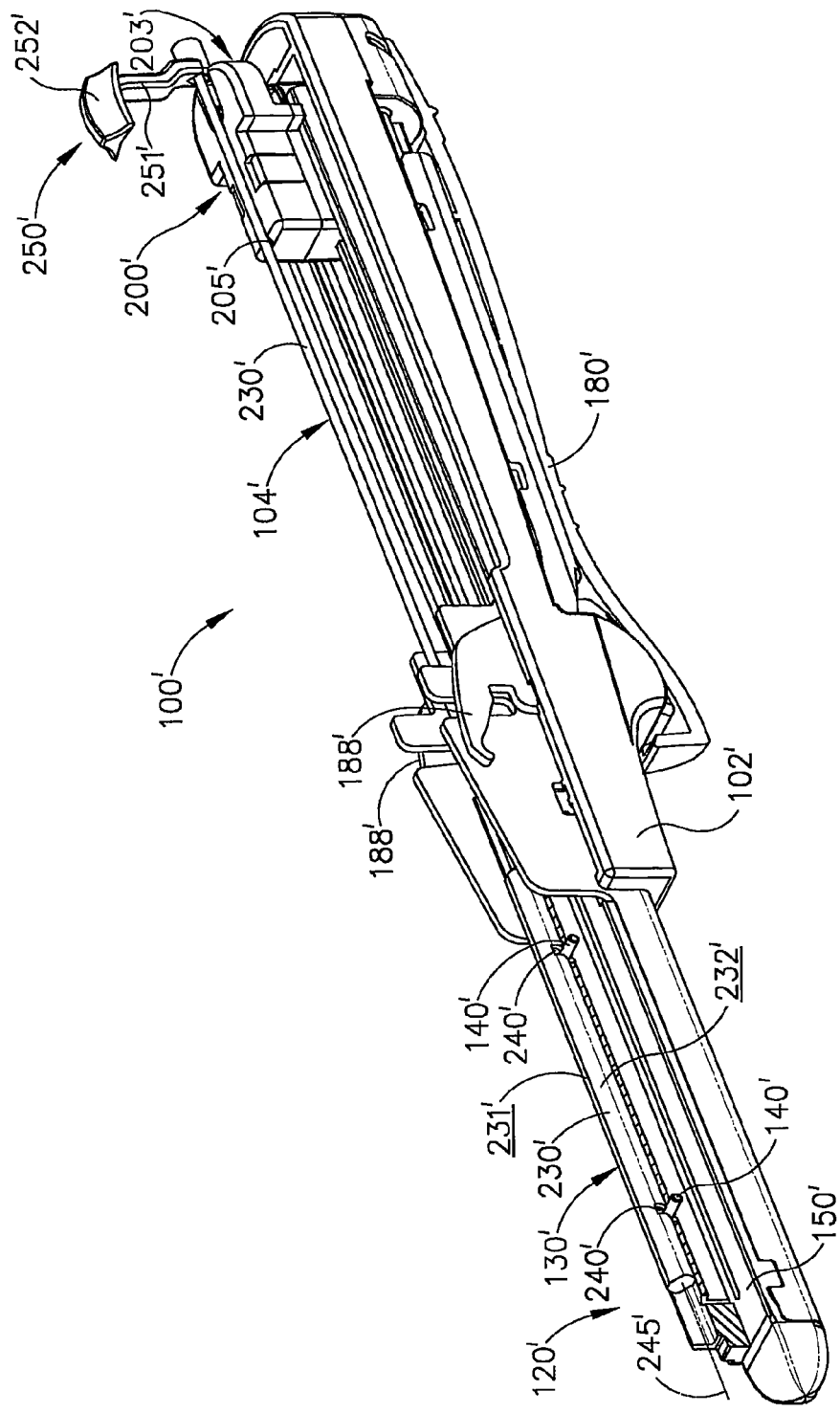
FIG. 27 is a perspective view of the surgical stapling instrument of FIG. 24 with some components removed and others shown in cross-section.
Figure 30:
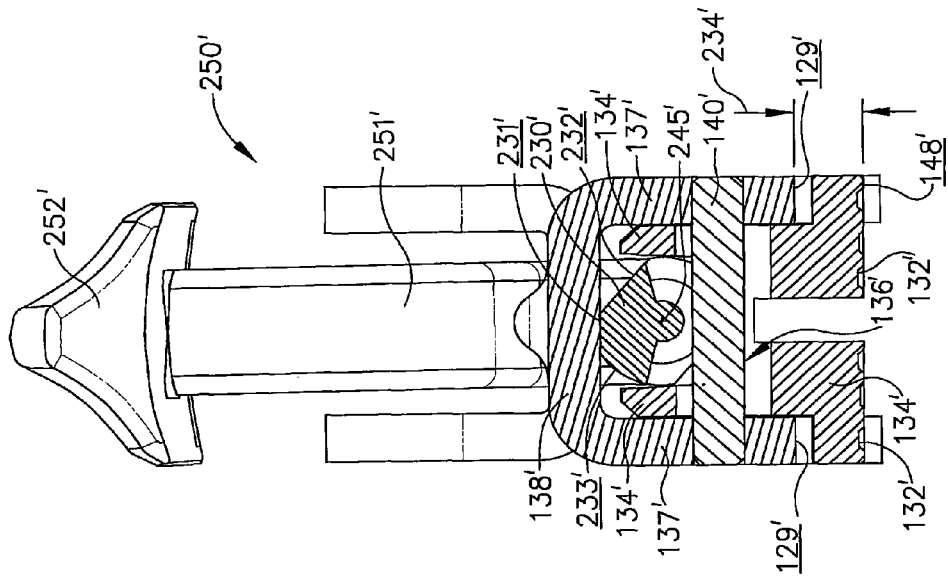
FIG. 30 is an end view of the surgical stapling instrument of FIG. 24 with some components removed and others shown in dashed lines illustrating the rotatable anvil adjustment member in the first orientation of FIG. 28.

In various embodiments, referring to FIG. 27, surgical instrument 100' can include a rotatable adjustment member 230' which can be selectively positioned in at least first and second positions so as to provide different staple forming heights. In certain embodiments, surgical instrument 100' can include an actuator 250' which can be operably connected to adjustment member 230' such that actuator 250' can move adjustment member 230' between at least its first and second positions. In at least one embodiment, referring to FIG. 28, actuator 250' can include actuator body 251' and grasping portion, or handle, 252'. Actuator body 251' can include an aperture 258' which can be configured to receive a proximal end 238' of adjustment member 230' such that rotational motion, torque, and/or forces can be transmitted between actuator 250' and adjustment member 230'. In at least one such embodiment, referring to FIG. 36, aperture 258' can comprise a non-circular profile and/or a profile which includes one or more flat drive surfaces configured to transmit rotational motion between actuator body 251' and actuator 230'. In certain embodiments, aperture 258' can be sized and configured to closely receive proximal end 238' of actuator 230'. In at least one embodiment, aperture 258' can be configured to receive proximal end 238' in a press-fit and/or snap-fit arrangement. In various embodiments, referring again to FIG. 28, handle portion 104' can include one or more slots 259' which can be configured to permit at least a portion of actuator body 251' to extend therethrough such that grasping portion 252' can be assembled to actuator body 251' with at least a portion of handle portion 104' positioned therebetween. In at least one such embodiment, second handle portion 104' can further include recess 253' which can be configured such that at least a portion, if not all, of grasping portion 252' is positioned within recess 253'. In certain embodiments, recess 253' can be configured such that grasping portion 252' does not extend above the top surface of second handle portion 104' although, in other embodiments, an upper portion of grasping portion 252' can extend above second handle portion 104, as illustrated in FIG. 30, such that grasping portion 252' can be easily accessed by a surgeon.

Figure 31:
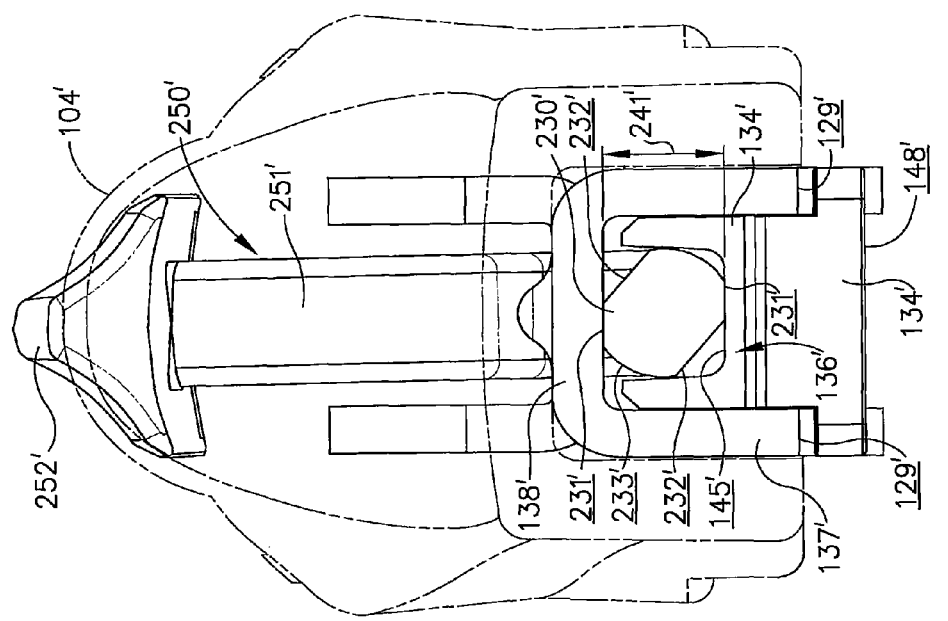
FIG. 31 is a cross-sectional end view of the surgical stapling instrument of FIG. 24 taken along line 31-31 in FIG. 24.
Figure 36:
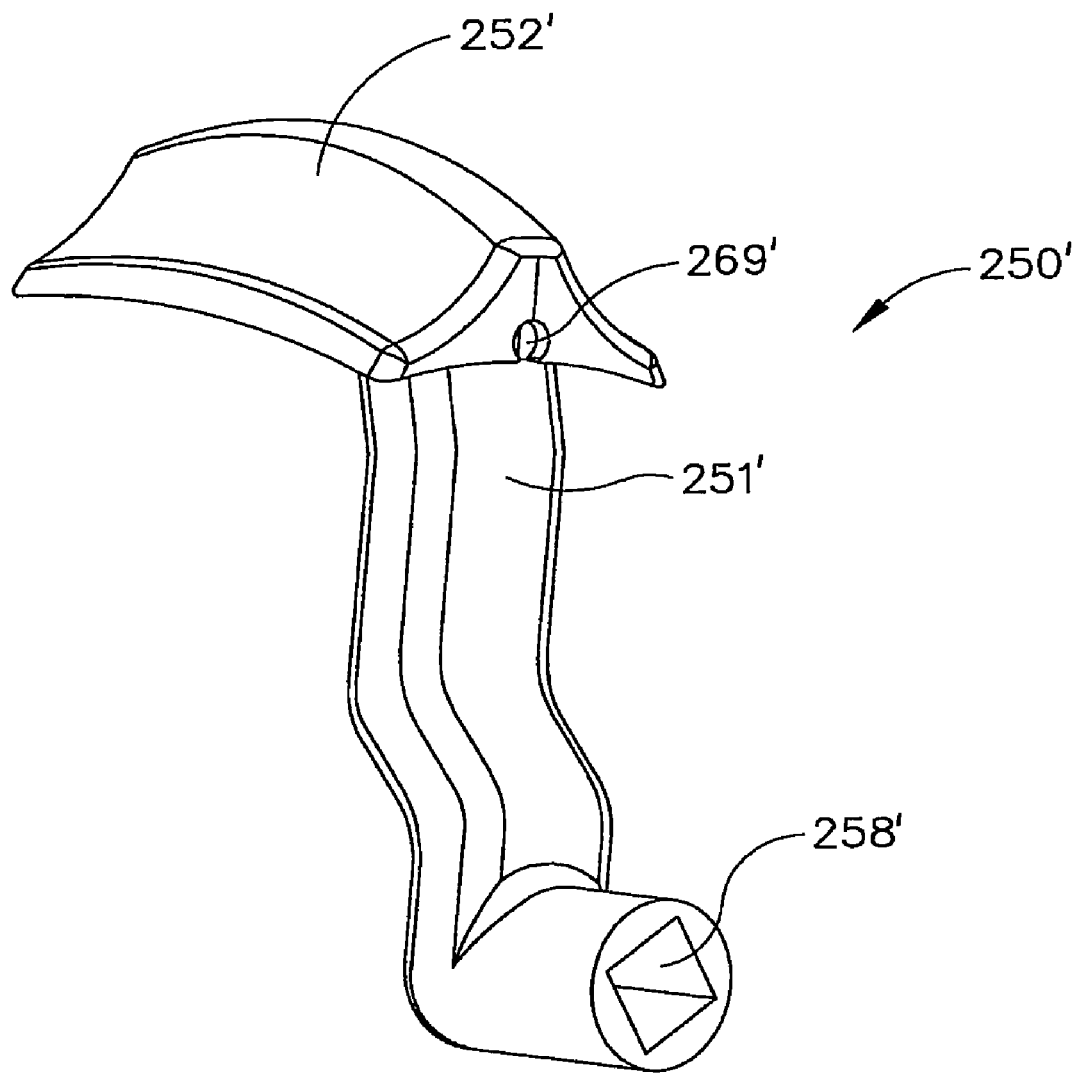
FIG. 36 is a perspective view of an actuator for rotating the anvil adjustment member of FIG. 28.

In various embodiments, as outlined above, an adjustment member can be rotatable between at least first and second positions in order to adjust the forming height of staples deployed by a surgical stapler. In certain embodiments, referring to FIG. 28, a surgical stapling instrument can include an adjustment member rotatably positioned within an anvil wherein the adjustment member can be configured to limit the relative movement of a movable anvil portion. In at least one such embodiment, surgical stapling instrument 100' can include an anvil plate 134' which can be slidably retained within anvil channel 136' by retention, or guide, pins 140', wherein guide pins 140' can be configured to allow anvil plate 134' to slide upwardly when anvil plate 134' comes into contact with tissue as described above. Referring to FIGS. 27, 30, and 31, adjustment member 230' can be positionable in a first position, or orientation, such that it can limit the upward movement of anvil plate 134' within anvil channel 136' and dictate the staple forming height of the staples. In at least one such embodiment, referring to FIGS. 30 and 31, adjustment member 230' can include opposing first surfaces 231' which can be positioned intermediate base 138' of anvil channel 136' and positioning surface 145' of anvil plate 134' such that, when positioning surface 145' contacts one of first surfaces 231', tissue-contacting surface 148' of anvil plate 134' can be positioned a first distance 234' away from a datum surface 129' on anvil 130', for example. Correspondingly, forming surfaces 132' can be positioned a first distance away from a staple cartridge such that, when staples are deployed from the staple cartridge, the staples can be deformed to a first staple height. Further to the above, a first diameter 241' can be defined between first surfaces 231' wherein the first diameter 241' can define the maximum upward position of anvil plate 134' within anvil channel 136'.

As indicated above, adjustment member 230' can be rotated in order to adjust the forming height of the staples. In various embodiments, adjustment member 230' can be rotated between its first position, or orientation, (FIGS. 30 and 31) and a second position, or orientation (FIGS. 32 and 33). In at least one embodiment, referring to FIGS. 32 and 33, handle 252' can be rotated in a direction indicated by arrow "A" in order to move adjustment member 230' between its first and second positions. Similar to the above, when actuator 230' is in its second position, or orientation, actuator 230' can limit the upward movement of anvil plate 134' within anvil channel 136' and dictate the staple forming height of the staples. In at least one such embodiment, referring to FIGS. 32 and 33, adjustment member 230' can include opposing second surfaces 232' which can be positioned intermediate base 138' and positioning surface 145' such that, when positioning surface 145' contacts one of second surfaces 232', tissue-contacting surface 148' of anvil plate 134' can be positioned a second distance 235' away from datum surface 129', for example. Correspondingly, forming surfaces 132' can be positioned a second distance away from a staple cartridge such that, when staples are deployed from the staple cartridge, the staples can be deformed to a second staple height. In various embodiments, similar to the above, a second diameter 242' can be defined between second surfaces 232', wherein second diameter 242' can define the maximum upward position of anvil plate 134' within anvil channel 136'. Although first surfaces 231' and second surfaces 232' can be defined by flat, or at least substantially flat, surfaces, other embodiments are envisioned in which the first and second surfaces 231' and 232' can include at least partially arcuate, or curved, contours. In any event, referring to FIG. 27, adjustment member 230' may include one or more clearance slots 240' which can be configured to provide clearance between actuator 230' and retention pins 140'. Clearance slots 240' can be configured to provide clearance between actuator 230' and retention pins 140' when actuator 230' is in its first position, second position, and/or any other suitable position.

In various embodiments, further to the above, adjustment member 230' can be rotated between its first position, or orientation, (FIGS. 30 and 31) and a third position, or orientation (FIGS. 34 and 35). In at least one embodiment, referring to FIGS. 34 and 35, handle 252' can be rotated in a direction indicated by arrow "B" in order to move adjustment member 230' between its first and third positions. Similar to the above, when actuator 230' is in its third position, or orientation, actuator 230' can limit the upward movement of anvil plate 134' within anvil channel 136' and dictate the staple forming height of the staples. In at least one such embodiment, referring to FIGS. 34 and 35, adjustment member 230' can include opposing third surfaces 233' which can be positioned intermediate base 138' and positioning surface 145' such that, when positioning surface 145' contacts one of third surfaces 233', tissue-contacting surface 148' of anvil plate 134' can be positioned a third distance 236' away from datum surface 129', for example. Correspondingly, forming surfaces 132' can be positioned a third distance away from a staple cartridge such that, when staples are deployed from the staple cartridge, the staples can be deformed to a third staple height. In various embodiments, similar to the above, a third diameter 243' can be defined between third surfaces 233', wherein third diameter 243' can define the maximum upward position of anvil plate 134' within anvil channel 136'. Referring once again to FIGS. 34 and 35, third surfaces 233' can be defined by an at least partially arcuate contour, although other embodiments are envisioned in which third surfaces 233' can include flat, or at least substantially flat, contours. In at least one embodiment, adjustment member 230' can be configured such that the largest distance, or diameter, between the arcuate third surfaces 233' can be utilized to define the third staple height.

As described above, referring to FIGS. 30 and 31, adjustment member 230' can be positioned in a first position, or orientation, to set a first forming height for the staples deployed by surgical stapling instrument 100'. As also described above, referring to FIGS. 32 and 33, actuator 250' can be utilized to move adjustment member 230' into its second position, or orientation, to set a second forming height for the staples. To do this, in at least one embodiment, a force can be applied to handle 252' which can cause handle 252', and adjustment member 230' attached thereto, to rotate in a direction indicated by arrow "A". In at least one embodiment, adjustment member 230' and/or actuator 250' can be sufficiently retained such that, when adjustment member 230' is rotated, adjustment member 230' can be rotated about an axis, such as axis 245' (FIG. 27), for example. In at least one embodiment, referring to FIG. 25, the proximal end 203' of pusher bar assembly 200' can include one or more grooves, channels, or recesses 205' which can be configured to receive and/or retain at least a portion of adjustment member 230' and/or actuator 250' therein. In any event, as illustrated in FIGS. 30-33, the second position, or orientation, of adjustment member 230' can allow anvil plate 134' to slide a larger distance within anvil channel 136' as compared to when adjustment member 230' is in its first position. In at least one embodiment, as a result, the second staple forming height can be larger than the first staple forming height. As also described above, referring to FIGS. 34 and 35, actuator 250' can be utilized to move adjustment member 230' into its third position, or orientation, to set a third forming height for the staples. To do this, in at least one embodiment, a force can be applied to handle 252' which can cause handle 252', and adjustment member 230' attached thereto, to rotate in a direction indicated by arrow "B". As illustrated in FIGS. 30, 31, 34, and 35, the third position, or orientation, of adjustment member 230' can allow anvil plate 134' to slide a smaller distance within anvil channel 136' as compared to when adjustment member 230' is in its first position. In at least one embodiment, as a result, the first and second staple forming heights can be larger than the third staple forming height. In at least one such embodiment, the first position of adjustment member 230', and actuator 250', can represent an intermediate position, wherein adjustment member 230' can be selectively moved into its second and third positions directly from its first position. In effect, the first position of adjustment member 230' can represent an intermediate staple height, wherein the second and third staple positions of adjustment member 230' can represent taller and shorter staple heights, respectively. In certain embodiments, referring to FIG. 24, surgical stapling instrument 100' can include one or more indicia thereon which can be configured to convey the staple forming heights, or at least relative forming heights, that can be selected. For example, second handle portion 104' can include a first indicium 245' which can indicate an intermediate, or first, staple height, a second indicium 246' which can indicate a taller, or second, staple height, and, in addition, a third indicium 247' which can indicate a shorter, or third, staple height.

In various embodiments, further to the above, one or more of first surfaces 231', second surfaces 232', and third surfaces 233' can comprise or define, or at least partially comprise or define, a perimeter, or circumference, of adjustment member 230'. As discussed above, owing to the first, second, and third diameters (241', 242', and 243') defined by the first, second, and third surfaces (231', 232', and 233'), respectively, the perimeter, or circumference, of adjustment member 230' may be non-circular. In certain embodiments, though, the perimeter, or circumference of adjustment member 230', may be symmetrical, substantially symmetrical, and/or non-symmetrical. In various embodiments, further to the above, an adjustment member can comprise a cam rotatably positioned intermediate base 138' of anvil 130' and adjustment surface 145' of anvil plate 134', for example. In at least one such embodiment, one or more of first surfaces 231', second surfaces 232', and third surfaces 233', for example, can comprise or define a cam profile which, similar to the above, can be configured to either positively position anvil plate 134' and/or provide a stop against which anvil plate 134' can be positioned. In any event, although not illustrated, various embodiments are envisioned in which an adjustment member can be slid and rotated in order to set two or more staple forming heights for staples deployed by a surgical stapling instrument. In at least one such embodiment, an adjustment member can comprise a cam profile which can be defined along the length of the adjustment member wherein longitudinal and/or rotational movement can be utilized to move the cam profile between at least first and second positions.

Figure 26:
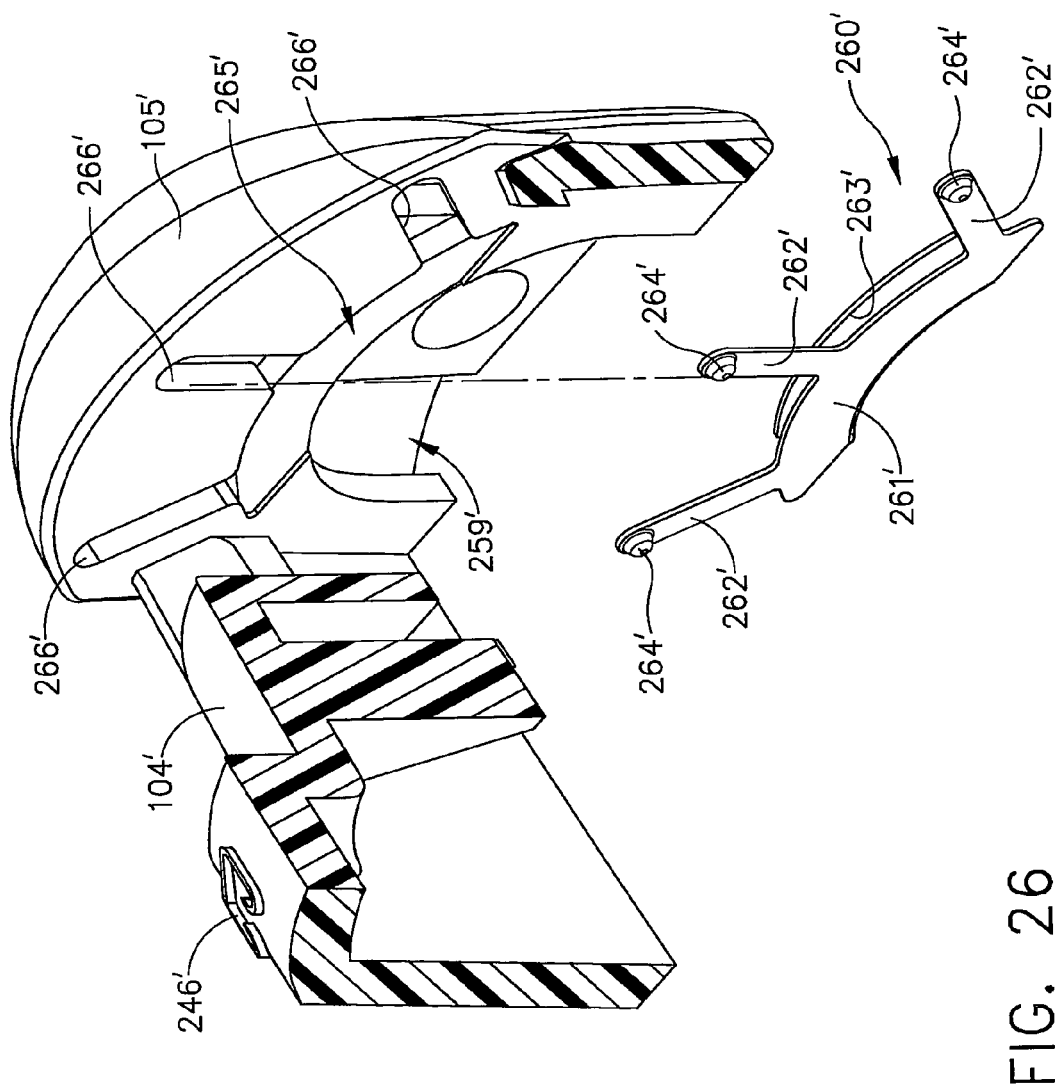
FIG. 26 is a partial exploded view of the proximal end of the surgical stapling instrument of FIG. 24 including a detent mechanism for releasably holding a rotatable anvil adjustment member in position.

In various embodiments, similar to the above, surgical instrument 100' can further include a detent mechanism configured to hold, or at least releasably hold, actuator 250' in position. In at least one embodiment, referring to FIGS. 25 and 26, surgical instrument 100' can further include detent member 260' comprising detent body 261' and one or more detent legs 262'. Referring to FIG. 26, detent body 261' can include one or more grooves, recesses, or channels 263' which can be configured to receive at least a portion of proximal end 105' of second handle portion 104' therein such that detent member 260' can be retained in position. In at least one such embodiment, proximal end 105' can further include one or more grooves, channels, or recesses 265' which can be configured to closely receive detent member 260'. In certain embodiments, at least a portion of detent body 261', such as channel 263', for example, can be press-fit, snap-fit, and/or otherwise suitably retained in recess 265'. As also illustrated in FIG. 26, each detent leg 262' of detent member 260' can include one or more projections 264' extending therefrom which can be configured to engage actuator body 251' and releasably hold actuator 250' in position. In at least one embodiment, referring to FIG. 36, actuator body 251' can include one or more recesses, or holes, 269' which can be configured to receive a projection 264'. When a projection 264' is positioned within recess 269', the projection can be configured to hold actuator 250' in its first position, for example, until a sufficient force is applied to actuator 250' so as to cause the projection 264' to be displaced out of recess 269'. More particularly, the force applied to actuator 250' can be transmitted to the projection 264' and, owing to cooperating surfaces between the projection 264' and recess 269', the detent leg 262' associated with the projection 264' can be flexed or moved proximally to allow actuator body 251' to be moved relative thereto. In order to accommodate such proximal movement, referring to FIG. 25, recess 265' can include elongate portions 266' which can each be configured to receive at least a portion of legs 262' such that legs 262' can move relative to handle portion 104'. As actuator 250' is moved into either its second or third position, actuator body 251' can contact a projection 264' extending from another leg 262' and deflect the leg 262' proximally such that, once actuator 250' is in its second or third positions, the leg 262' can spring forward, or distally, such that the projection 264' can be secured within recess 269'. In at least one embodiment, further to the above, the interaction between projections 264' and the sidewalls of recess 269' can be such that actuator 250' can be securely held in one of its first, second, and third positions, for example, yet permit actuator 250' to be moved upon a sufficient application of force. In such embodiments, the detent member 260' can prevent, or at least inhibit, actuator 250' and, correspondingly, adjustment member 230' from being unintentionally displaced.

As discussed above and as shown in FIG. 2, each side flange 128 of first handle portion 102 can include a notch, or recess, 127, for example, which can be configured to receive one or more latch projections 131, for example, extending from anvil 130, and/or any other suitable portion of second handle portion 104. As also discussed above, referring primarily to FIGS. 2 and 3, first handle portion 102 can further include latching mechanism 180 rotatably mounted thereto which can be utilized to engage latch projections 131 extending from second handle portion 104 and secure the first and second handle portions 102, 104 together. Latching mechanism 180 can include one or more latch arms 188 extending therefrom which can be configured to engage latch projections 131 and pull and/or secure projections 131 within recesses 127 as illustrated in FIG. 7. Referring to FIG. 6, at least one of latch arms 188 can include a distal hook 189 which can be configured to wrap around at least a portion of projections 131 so as to encompass or surround, or at least partially encompass or surround, projections 131. In at least one embodiment, latch arms 188 can act as an over-center latch to maintain latching mechanism 180 in its latched, or closed, position.

Figure 38:
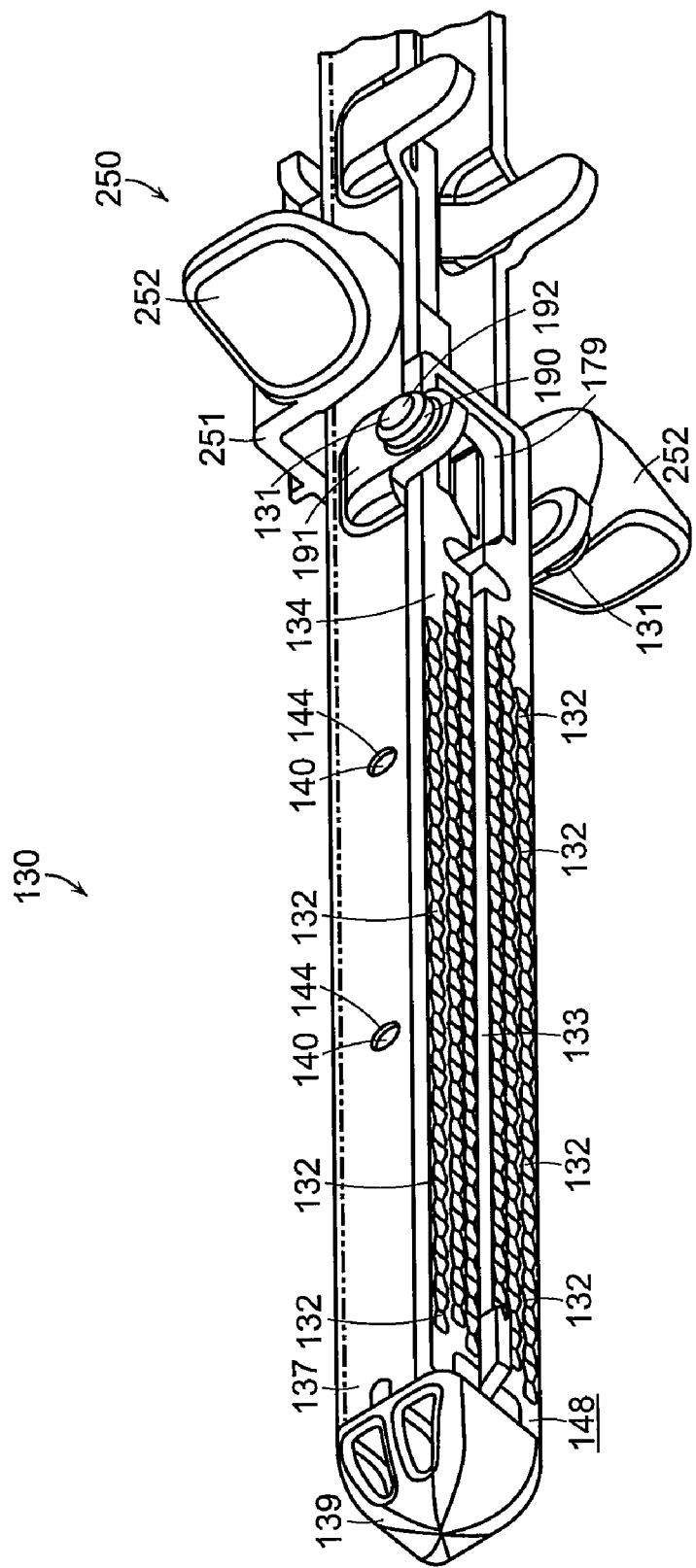
FIG. 38 is a similar perspective view of the surgical stapling instrument of FIG. 1 to that of FIG. 17.

In various embodiments, referring now to FIG. 38, each projection 131 can comprise a slot, or groove, 190 positioned intermediate sidewall 191 and an enlarged end, or head, 192 of projection 131, wherein the slot 190 can be configured to receive at least a portion of latch arm 188. More particularly, in at least one embodiment, the slot 190 can have a width which is greater than the width of the latch arm 188 such that, when the latch arm 188 is engaged with the projection 131, the latch arm 188 can enter into slot 190. In some circumstances, the width of each slot 190 may be slightly larger than the width of a latch arm 188 such that the latch arm is closely received within the slot 190. In various circumstances, the slot 190, the sidewall 191, and the head 192 of projection 131 can be sized and configured so as to prevent, or at least limit, relative lateral movement, i.e., movement away from or to the sides of anvil 130, between latch arm 188 and projection 131. Further to the above, however, the latch arms 188 can slide longitudinally within the grooves 190 as the latch arms 188 move the projections 131 into the recesses 127 in first portion 102. Owing to such relative sliding movement between latch arms 188 and projections 131, frictional forces can be generated therebetween which can resist the movement of latch arms 188. In various circumstances, the magnitude of such frictional forces can be significant when the normal, or perpendicular, contact forces between the latch arms 188 and the sidewalls of groove 190 are large. In many circumstances, as a result, the operator of the surgical instrument has to overcome these frictional forces when actuating clamping mechanism 180.

Figure 39:
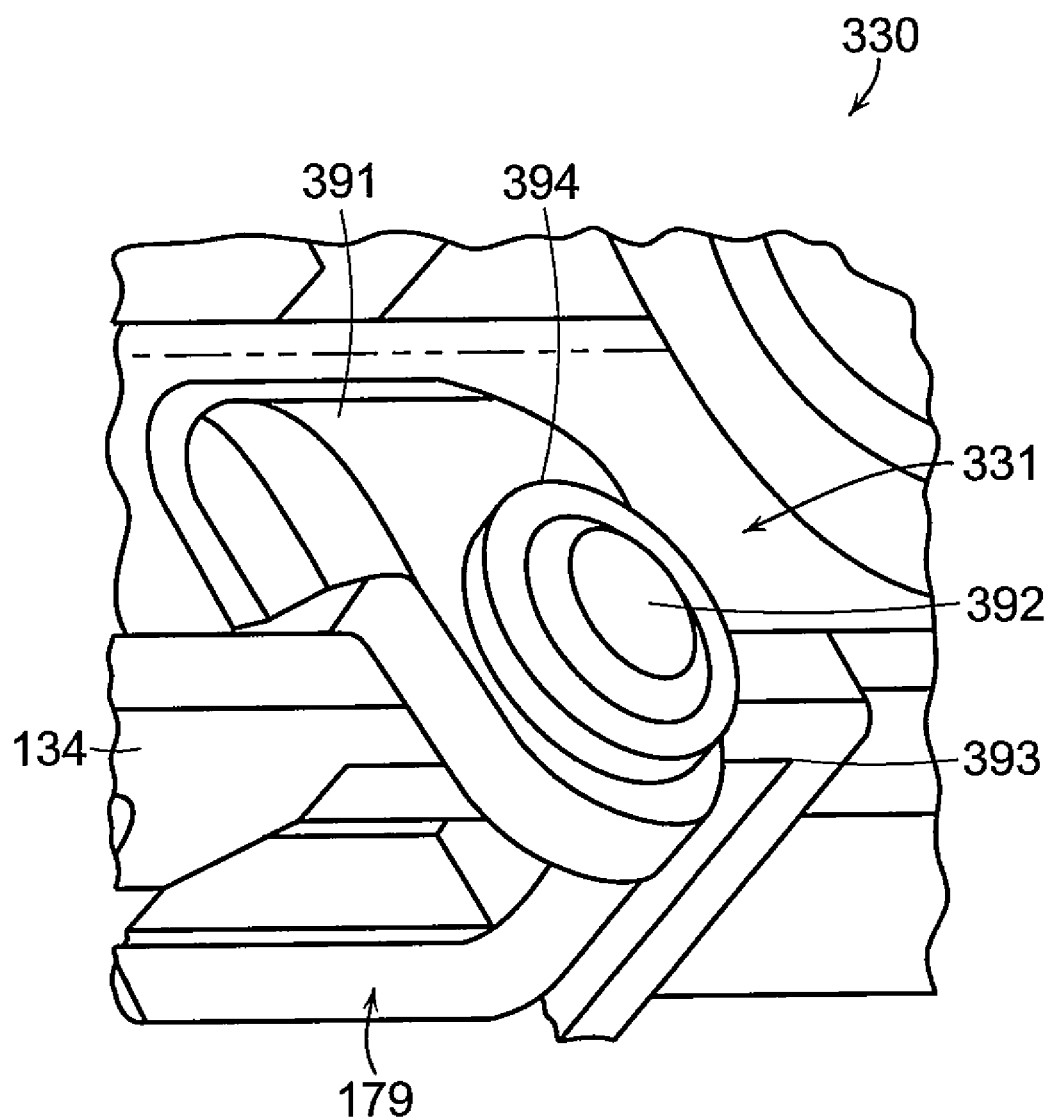
FIG. 39 is a detail view of a latch projection extending from an anvil of a surgical stapling instrument in accordance with at least one alternative embodiment of the present invention.
Figure 40:
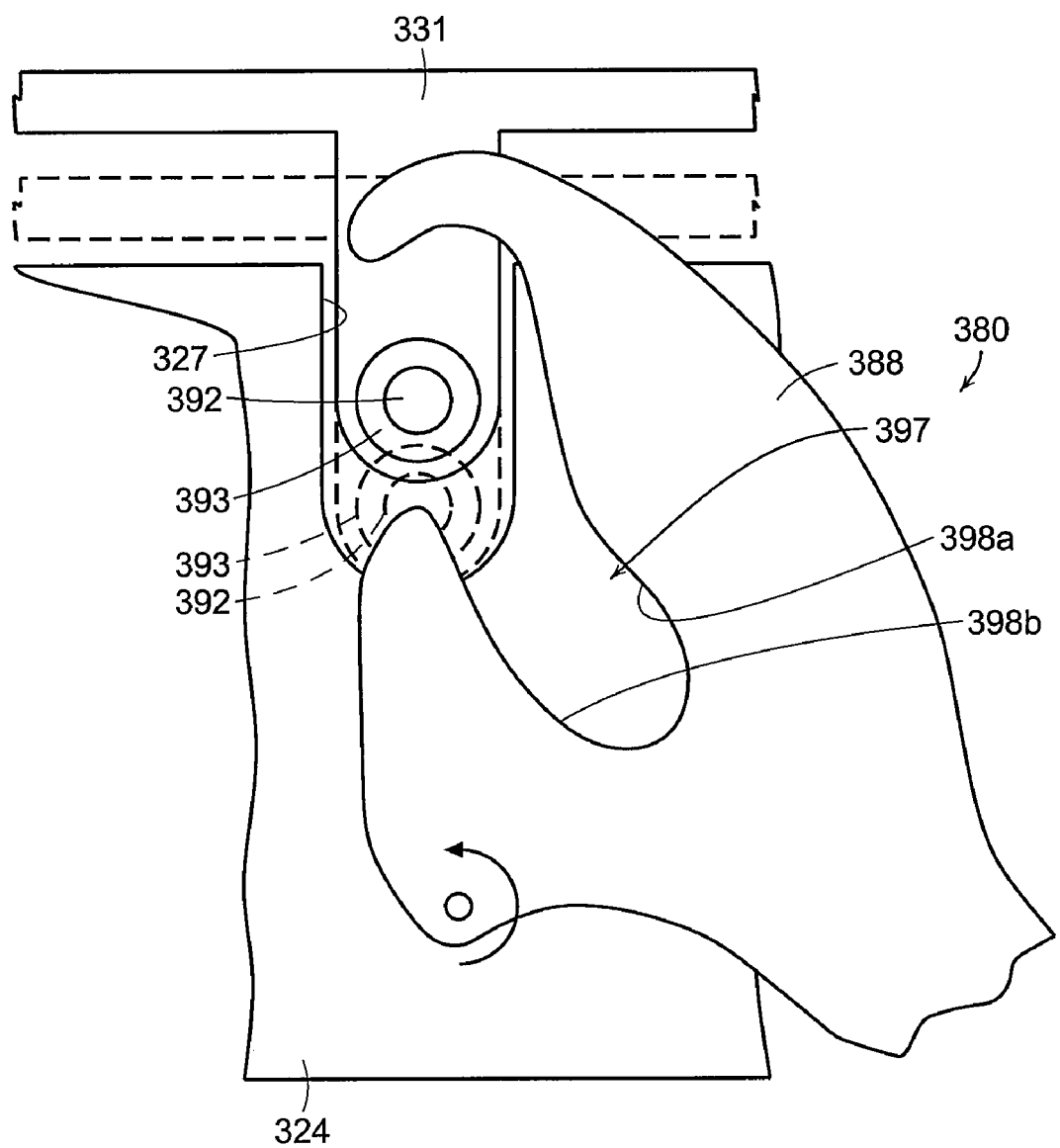
FIG. 40 is a diagram illustrating the latch projection of FIG. 39 and a latch configured to engage the latch projection and move the latch projection into a latch recess.

In various alternative embodiments, referring now to FIGS. 39 and 40, a surgical instrument can comprise one or more latch projections having a rotatable bearing which can reduce the magnitude of the friction forces between the latch arms of a latching mechanism and the latch projections. In at least one embodiment, an anvil 330, which can be substantially similar to anvil 130 in many respects, can comprise a latch projection 331 extending from each side thereof, wherein each latch projection 331 can comprise a rotatable bearing 393. In use, the latch arms 188 of latching mechanism 180, for example, can contact the rotatable bearings 393 in order to position the latch projections 331 in recesses 127. In various circumstances, the latch arms 188 can slide across the surface, or outer diameter, of bearings 393; however, as bearings 393 can rotate relative to the latch arms 188, the magnitude of the frictional forces between the latch arms 188 and projections 331 can be lower than the magnitude of the frictional forces between latch arms 188 and projections 131. Owing to such lower frictional forces, a lower closing, or clamping, force may be required to actuate clamping mechanism 180, for example.

Figure 41:
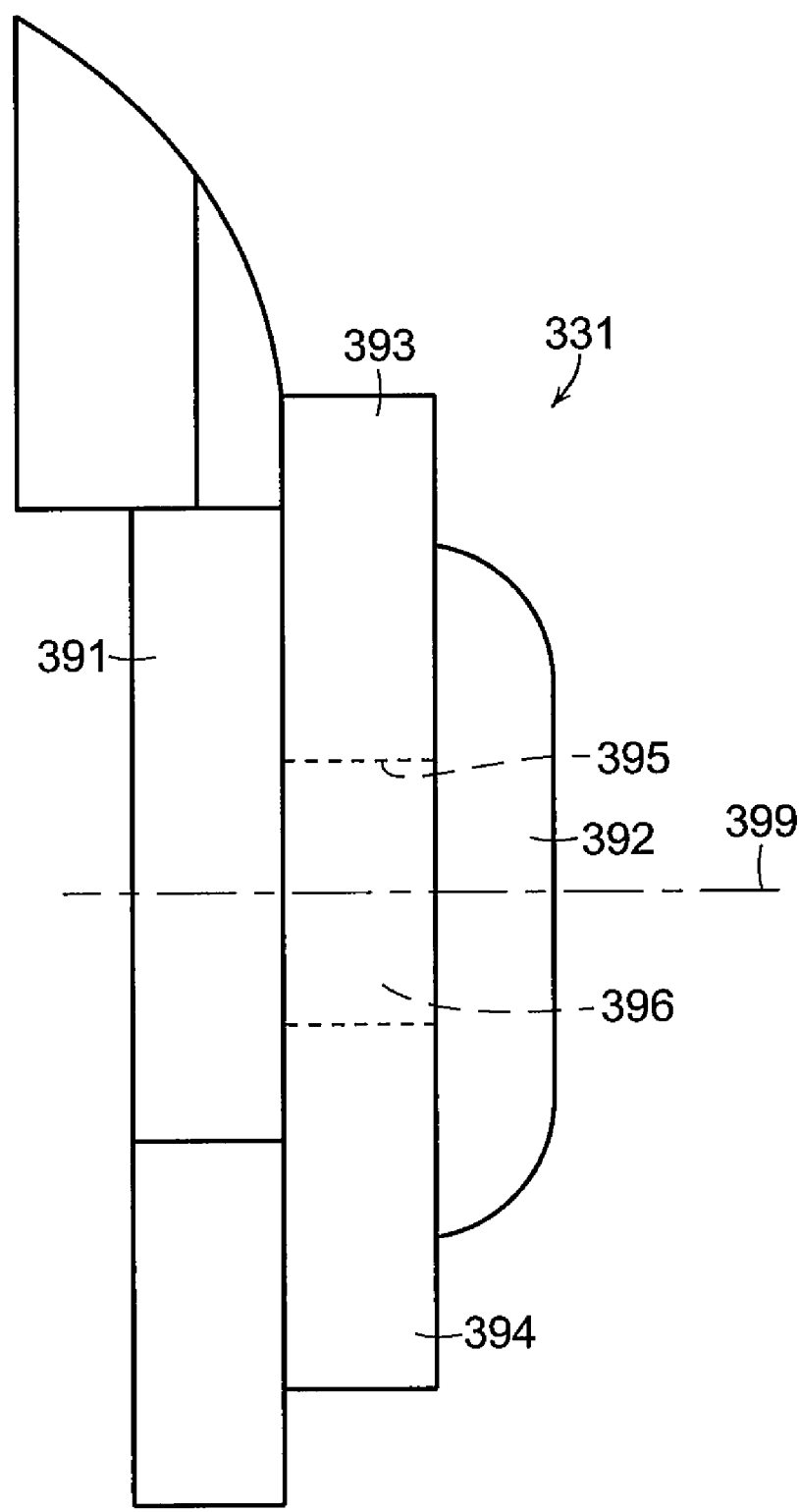
FIG. 41 is an elevational view of the latch projection of FIG. 39.

In various embodiments, referring primarily to FIG. 41, each rotatable bearing 393 can comprise a circular, or round, outer diameter 394 and, in addition, a circular, or round, bearing aperture 395 extending therethrough. In certain embodiments, each projection 331 can further comprise a shaft portion 396 extending from sidewall 391 and an enlarged end, or head, 392 extending from shaft portion 396, wherein, as illustrated in FIG. 31, the shaft portion 396 can extend through the bearing aperture 395 of rotatable bearing 393. In various embodiments, the shaft portion 396 can comprise a circular, or round, outer diameter which can be closely received within bearing aperture 395 such that there is little, if any, relative radial movement therebetween. The diameter of the bearing aperture 395, however, may be sufficiently larger than the outer diameter of shaft portion 396 such that bearing 393 can rotate relative to shaft portion 396 about an axis 399. In various embodiments, the rotatable bearing 393 can be retained on shaft portion 396 by the enlarged head 392. More particularly, in at least one embodiment, the enlarged head 392 may be larger than, or define a larger diameter than, the diameter of bearing aperture 395 such that rotatable bearing 393 cannot slide off the end of shaft portion 396. In certain embodiments, the sidewall 391 and the head 392 can define a gap distance therebetween and, in addition, the bearing 393 can comprise a width, wherein the gap distance can be larger than the width of bearing 393. In at least one embodiment, the gap distance may be slightly larger than the width of bearing 393 such that bearing 393 does not tilt, or at least substantially tilt, relative to axis 399, for example.

As discussed above, the latch arms 188 of latching mechanism 180 can be configured to engage bearings 393 and position bearings 393 within recesses 127. In various alternative embodiments, referring primarily to FIG. 40, a surgical instrument can comprise a latching mechanism 380 which can comprise first and second latch arms 388 extending therefrom on opposite sides of anvil 331 and staple cartridge channel 324. In use, similar to the above, the latch arms 388 can contact bearings 393 in order to move bearings 393 into recesses 327 in staple cartridge channel 324 and move anvil 331 toward staple cartridge channel 324. Such movement is illustrated with phantom lines in FIG. 41. In various embodiments, each latch arm 388 can at least partially define a groove, or slot, 397 therein, wherein each slot 397 can be configured to receive a bearing 393. In at least one embodiment, a slot 397 can comprise a first drive surface, or sidewall, 398a which can be positioned against bearing 393 and, as a closing force is applied to latching mechanism 380, the latch arm 388 can apply a closing force to the bearing 393. In such circumstances, the bearing 393 can move further into slot 397 as latching mechanism 380 is rotated into its closed position. In various circumstances, the slot 397 can further comprise a second drive surface, or sidewall, 398b which can be positioned against another and/or opposite side of bearing 393 such that an opening force can be applied to the bearing 393 via latch arm 388. As the latching mechanism 380 is moved into its open position, the bearing 393 can move out of slot 397. In any event, the first drive surface 398a and the second drive surface 398b can define a slot width therebetween which can be larger than the outside diameter of bearing 393 such that bearing 393 can move within slot 397. In some embodiments, the slot width may be slightly larger than the outside diameter of bearing 393. In at least one embodiment, at least portions of the first drive surface 398a and the second drive surface 398b can be parallel, or at least substantially parallel, to one another. In at least one such embodiment, at least portions of the first drive surface 398a can be positioned opposite the second drive surface 398b.

As described above, a surgical stapling instrument can be configured to deform one or more surgical staples between a first, undeployed, configuration and a second, deployed, configuration. In various embodiments, referring now to FIG. 39, a surgical staple, such as staple 400, for example, can comprise a base 402, a first leg, or deformable member, 404 extending from base 402, and, in addition, a second leg, or deformable member, 406 extending from base 402. In certain embodiments, the base 402, the first leg 404, and the second leg 406 can be comprised of a continuous wire, wherein, in at least one embodiment, the first leg 404 and the second leg 406 can each be bent in a direction which is perpendicular to the base 402 prior to staple 400 being inserted into and deformed by a surgical stapler. More particularly, the staple 400 can be manufactured such that base 402 is oriented along a baseline 401 and such that the legs 404 and 406 are oriented along lines 409 and 411, respectively, which are perpendicular, or at least substantially perpendicular, to the baseline 401. In various embodiments, the first leg 404 can be positioned at a first end of base 402 and the second end 406 can be positioned at a second end of base 402, wherein, in at least one embodiment, a mid-line 403 can be defined which extends through a midpoint of base 402 and which extends in a direction which is perpendicular to baseline 401. The staple 400 can be configured such that the base 402, first leg 404, and second leg 406 lie, or at least substantially lie, in the same, or common, plane when the staple 400 is in its first, or undeployed, configuration. In such embodiments, the baseline 401, along which the base 402 is oriented, and the perpendicular lines 409 and 411, along which the legs 404 and 406 are oriented, can lie in the same plane.

Figure 51:
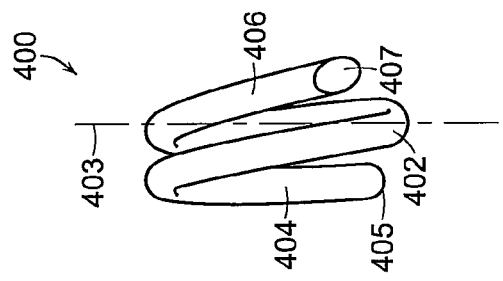
FIG. 51 is a side view of the surgical staple of FIG. 49 in the deformed shape of FIG. 50.
Figure 52:
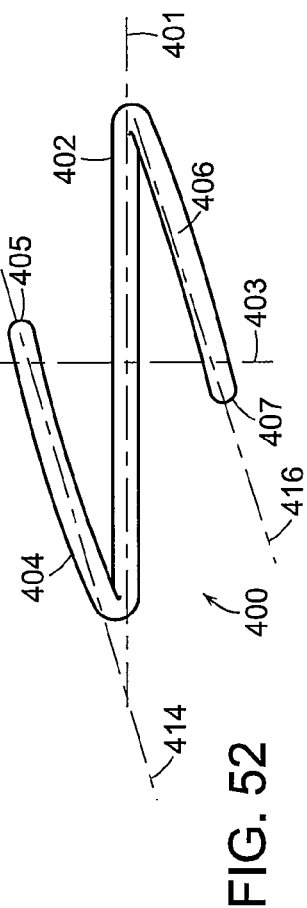
FIG. 52 is a plan view of the surgical staple of FIG. 49 in the deformed shape of FIG. 50.

In various embodiments, further to the above, the continuous wire comprising the base 402, the first leg 404, and the second leg 406 can be comprised of titanium and/or stainless steel, for example. In at least one embodiment, the first leg 404 can comprise a first end 405 and the second leg 406 can comprise a second end 407, wherein the ends 405 and 407 can each comprise a sharp, or chisel, tip which can be configured to puncture bone and/or tissue. In use, the staple 400 can be deformed by a surgical stapler in order to capture tissue, for example, within the staple 400. In various embodiments, the staple 400 can be deployed from a staple cartridge such that the ends 405 and 407 of staple legs 404 and 406, respectively, contact an anvil positioned opposite the staple 400. In such circumstances, a first compressive force F1 can be applied to the first leg 404 and a second compressive force F2 can be applied to the second leg 406 while the base 402 is supported by at least a portion of the staple cartridge. As described in greater detail below, the anvil can comprise a staple pocket which can apply the first compressive force F1 to the first leg 404 such that the end 405 of staple leg 404 is moved toward the base 402. Similarly, the staple pocket can apply the second compressive force F2 to the second staple leg 406 such that the end 407 of staple leg 404 is also moved toward base 402. In addition to the above, as also discussed in greater detail below, referring now to FIGS. 50-52, the staple pocket can bend the first staple leg 404 to a first side of base 402 and the second staple leg 406 to a second, or opposite, side of base 402.

Figure 49:
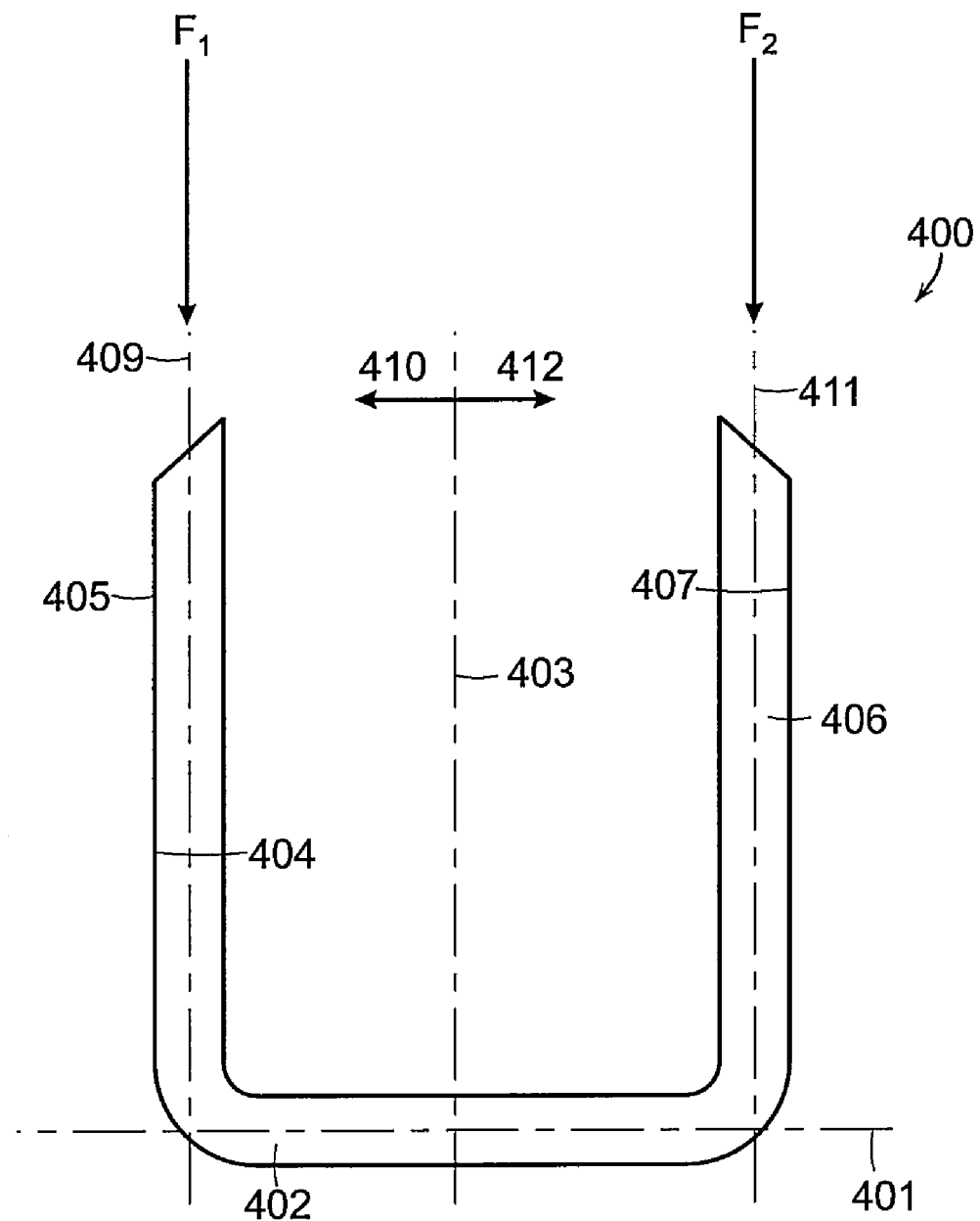
FIG. 49 is an elevational view of a surgical staple in an undeformed shape.
Figure 50:
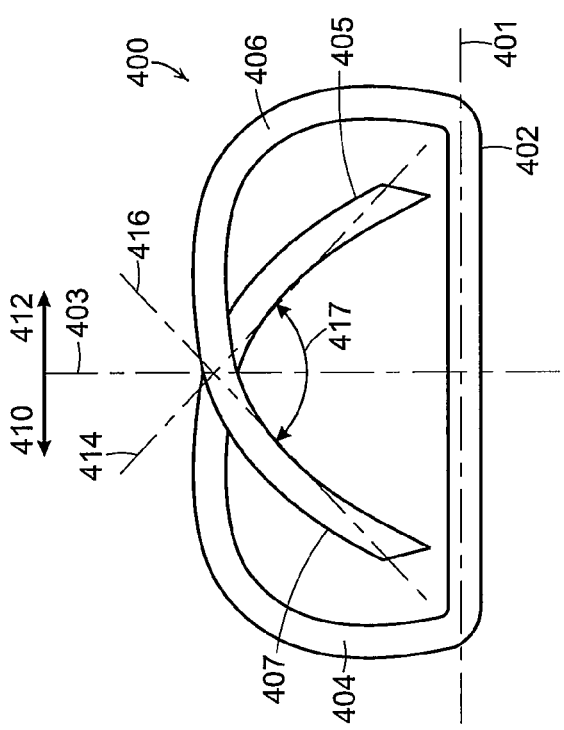
FIG. 50 is an elevational view of the surgical staple of FIG. 49 in a deformed shape in accordance with at least one embodiment of the present invention.

In various embodiments, referring to FIGS. 49 and 50, the first leg 404 of staple 400 can be bent such that the end 405 of the first leg 404 is moved toward the base 402 and toward the second leg 406 when the first leg 404 is deformed by the first compressive force F1. In at least one embodiment, the end 405 can be moved from a first side 410 of midline 403, as illustrated in FIG. 49, to a second side 412 of midline 403, as illustrated in FIG. 50. Similarly, the second leg 406 of staple 400 can be bent such that the end 407 of the second leg 406 is moved toward the base 402 and toward the first leg 404 when the second leg 406 is deformed by the second compressive force F2. In at least one embodiment, the end 407 can be moved from a second side 412 of midline 403, as illustrated in FIG. 49, to a first side 410 of midline 403, as illustrated in FIG. 50. In the deployed, or deformed, configuration of staple 400, as illustrated in FIG. 50, the ends 405 and 407 of staple legs 404 and 406 can extend across the midline 403 in such a way that they form an angle therebetween. More particularly, the end 405 of the first leg 404, when it is in its deformed configuration, can extend along or with respect to a first axis 414 and, similarly, the end 407 of the second leg 406, when it is in its deformed configuration, can extend along or with respect to a second axis 416 such that the first axis 414 and the second axis 416 define an angle 417 therebetween. In some embodiments, the angle 417 may be approximately 90 degrees, for example. In certain embodiments, the angle 417 may be in a range between approximately 0.1 degrees and approximately 89 degrees, for example. In various embodiments, the angle 417 may be greater than 90 degrees, while, in at least one embodiment, the angle 417 may be greater than approximately 90 degrees but less than 180 degrees, for example.

In various embodiments, further to the above, the first axis 414 and the second axis 416 can, in various embodiments, be oriented, or crossed, at a transverse angle with respect to each other, i.e., at least when the staple 400 is viewed from the side or elevational view of FIG. 50. More particularly, upon reviewing FIG. 52, it becomes evident that, although axes 414 and 416 extend in transverse directions when viewed from the side (FIG. 50), the axes 414 and 416 may not, in at least one embodiment, actually intersect one another. In such embodiments, when viewing the staple 400 from the top or bottom (FIG. 52), for example, the axes 414 and 416 may extend in parallel, or at least substantially parallel, directions. Furthermore, in various embodiments, the reader will note that the first axis 414 and the second axis 416 are not perpendicular with baseline 401. Stated another way, the end 405 of first staple leg 404 and the end 407 of second staple leg 406 are not pointing directly downwardly toward base 402 and baseline 401. In at least one such embodiment, the first axis 414 and the second axis 416 can each extend at an acute angle with respect to baseline 401, for example.

Figure 42:
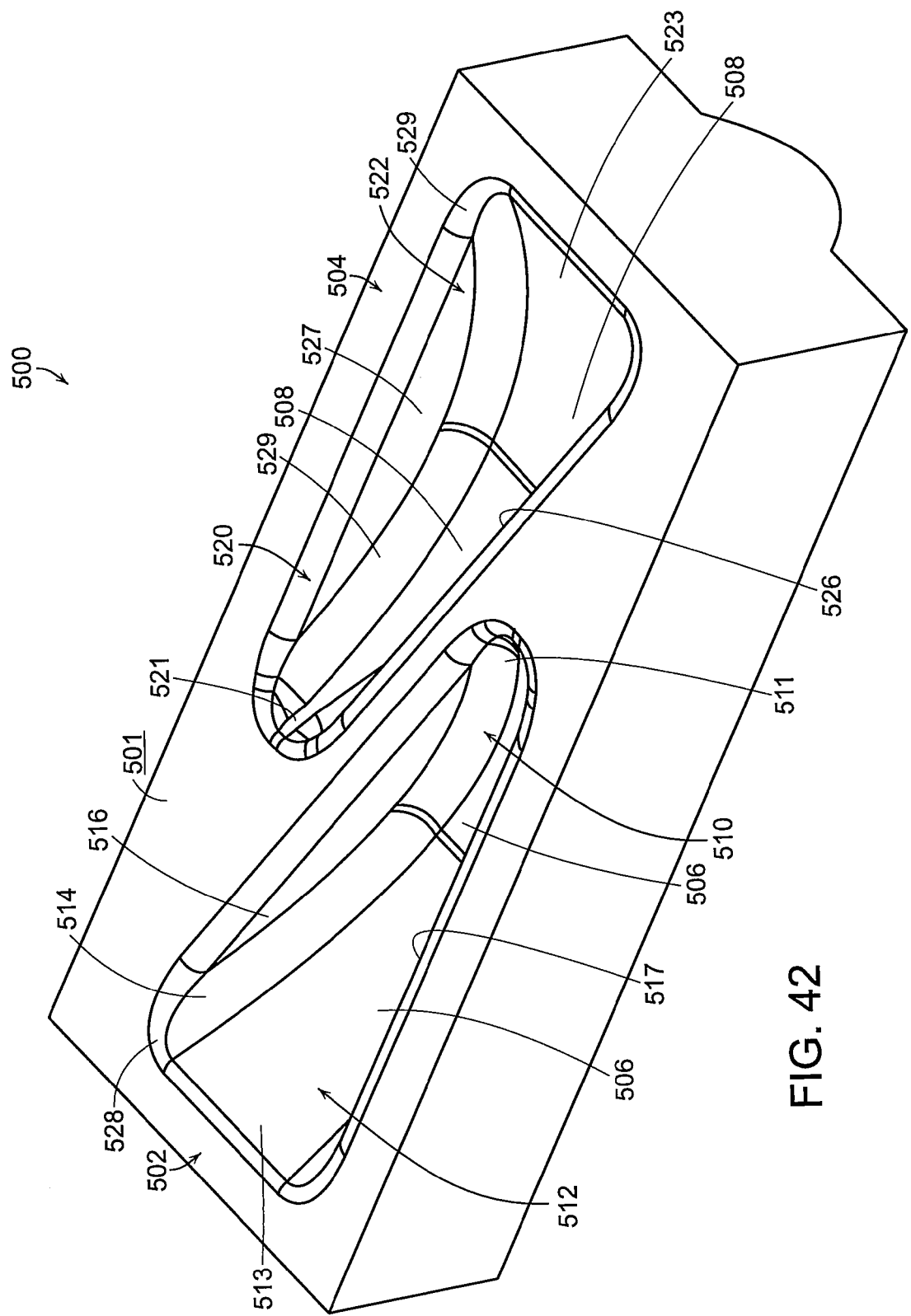
FIG. 42 is a perspective view of a staple pocket in accordance with at least one embodiment of the present invention.

As described above, a surgical instrument can be configured to deform the staple 400 of FIG. 49, for example, between an undeformed shape (FIG. 49) and a deformed shape (FIG. 50). In various embodiments, as also described above, the surgical instrument can comprise an anvil having a staple pocket configured to receive and deform at least a portion of the staple. In certain embodiments, referring now to FIG. 42, an anvil can comprise a tissue-contacting surface 501 and a plurality of staple pockets 500 formed therein, wherein each staple pocket 500 can be configured to deform a staple 400. In various embodiments, each staple pocket 500 can comprise a longitudinal axis 599 (FIG. 43) and, in addition, a first forming cup 502 and a second forming cup 504 positioned relative to the longitudinal axis 599. In use, the first forming cup 502 can be configured to receive the first staple leg 404 of staple 400 and the second forming cup 504 can be configured to receive the second staple leg 406. More particularly, in at least one embodiment, the staple pocket 500 can be positioned relative to the staple 400 such that, as the staple 400 is ejected from a staple cartridge, for example, the end 405 of first leg 404 can enter the first forming cup 502 and the end 407 of second leg 406 can enter the second forming cup 504. Further to the above, the end 405 of first staple leg 404 can contact the base 506 of first forming cup 502 such that the first compressive force F1 can be applied to the first leg 404 and, similarly, the end 407 of second staple leg 406 can contact the base 508 of second forming cup 504 such that the second compressive force F2 can be applied to the second leg 406.

Figure 46:
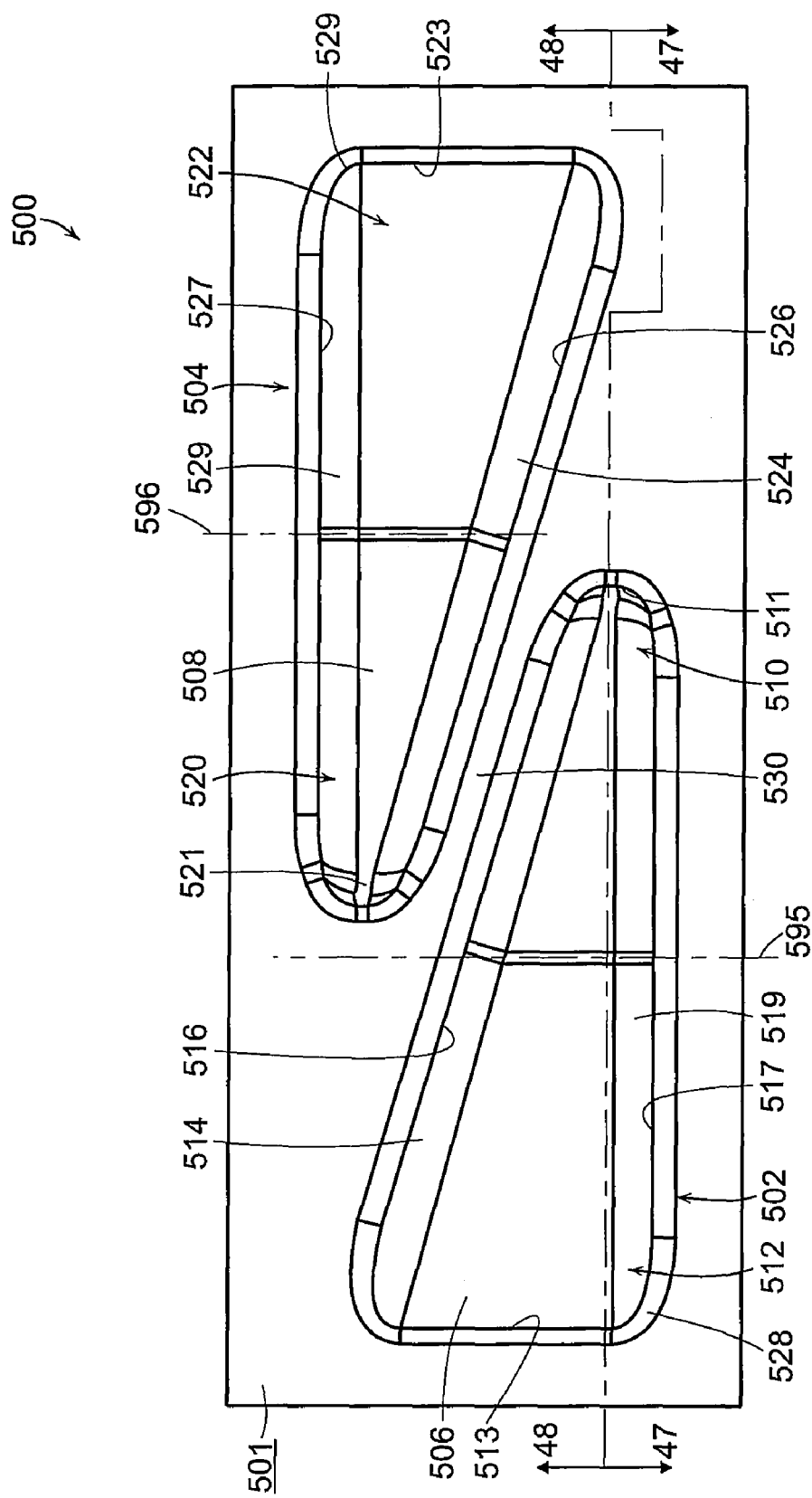
FIG. 46 is another top view of the staple pocket of FIG. 42.
Figure 47:
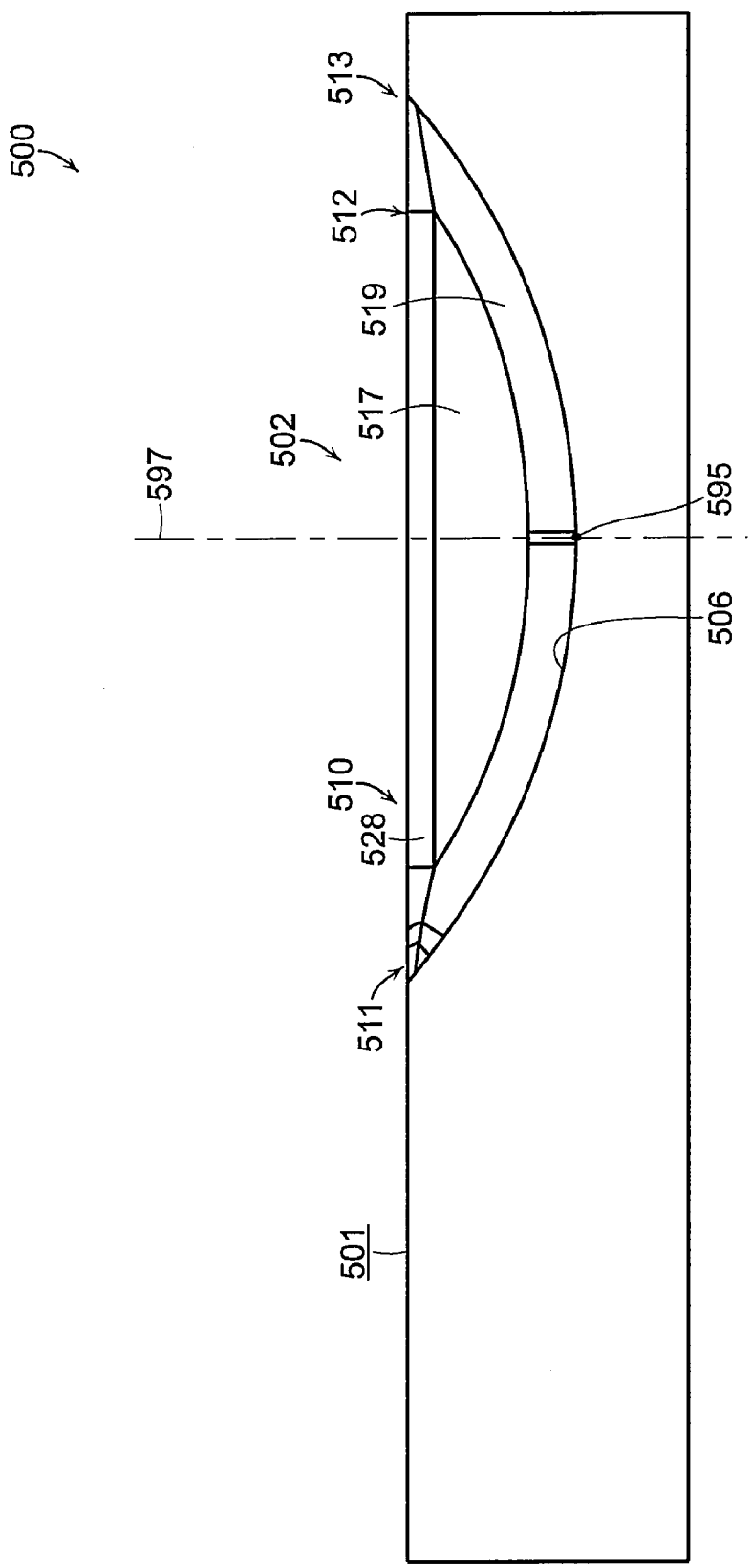
FIG. 47 is a cross-sectional view of the staple pocket of FIG. 42 taken along line 47-47 in FIG. 46.
Figure 48:
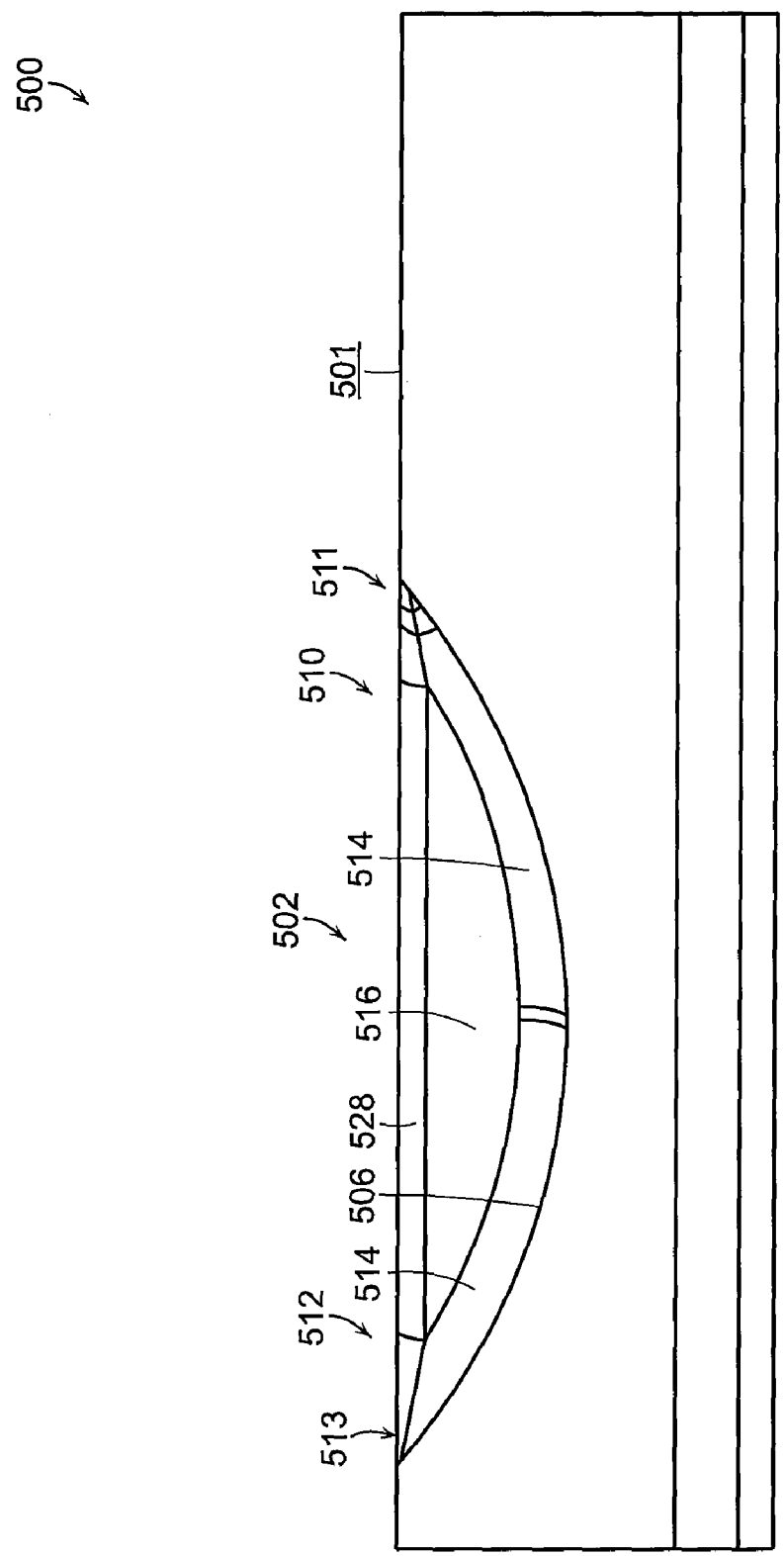
FIG. 48 is a cross-sectional view of the staple pocket of FIG. 42 taken along line 48-48 in FIG. 46.

In various embodiments, further to the above, the first forming cup 502 can comprise an inside portion 510 and an outside portion 512, wherein, when the end 405 of first staple leg 404 enters into the first forming cup 502, the end 405 can enter into the outside portion 512. Upon entering into the outside portion 512 of forming cup 502, the end 405 can contact base 506 and, owing to a concave curve of base 506, the end 405 can be directed inwardly toward the inside portion 510. More particularly, referring now to FIGS. 46-48, the base 506 can be curved toward tissue-contacting surface 501 such that, as the staple leg 404 contacts the base 506, the end 405 can be directed downwardly, i.e., away from tissue-contacting surface 501, and inwardly along the curved concave surface toward an inflection point 595. In various embodiments, the inflection point 595 can represent the point in which the concave surface of base 506 will begin to deflect the end 405 of first leg 404 upwardly toward the tissue-contacting surface 501. In various embodiments, the radius of curvature, r, of the concave surface can be constant, or at least substantially constant, in the longitudinal direction along the length thereof as illustrated in FIGS. 47 and 48. In certain embodiments, the radius of curvature r of the concave surface of base 506 can be consistent across the width of base 506 between a first interior sidewall 516 and a first exterior sidewall 517. In any event, as the end 405 of first leg 404 is advanced into the inside portion 510 of forming cup 502, the end 405 can come into contact with a radius transition 514 positioned intermediate the base 506 and the first interior sidewall 516. In such embodiments, the radius transition 514 can be configured to direct the end 405 against the first interior sidewall 516.

Figure 43:
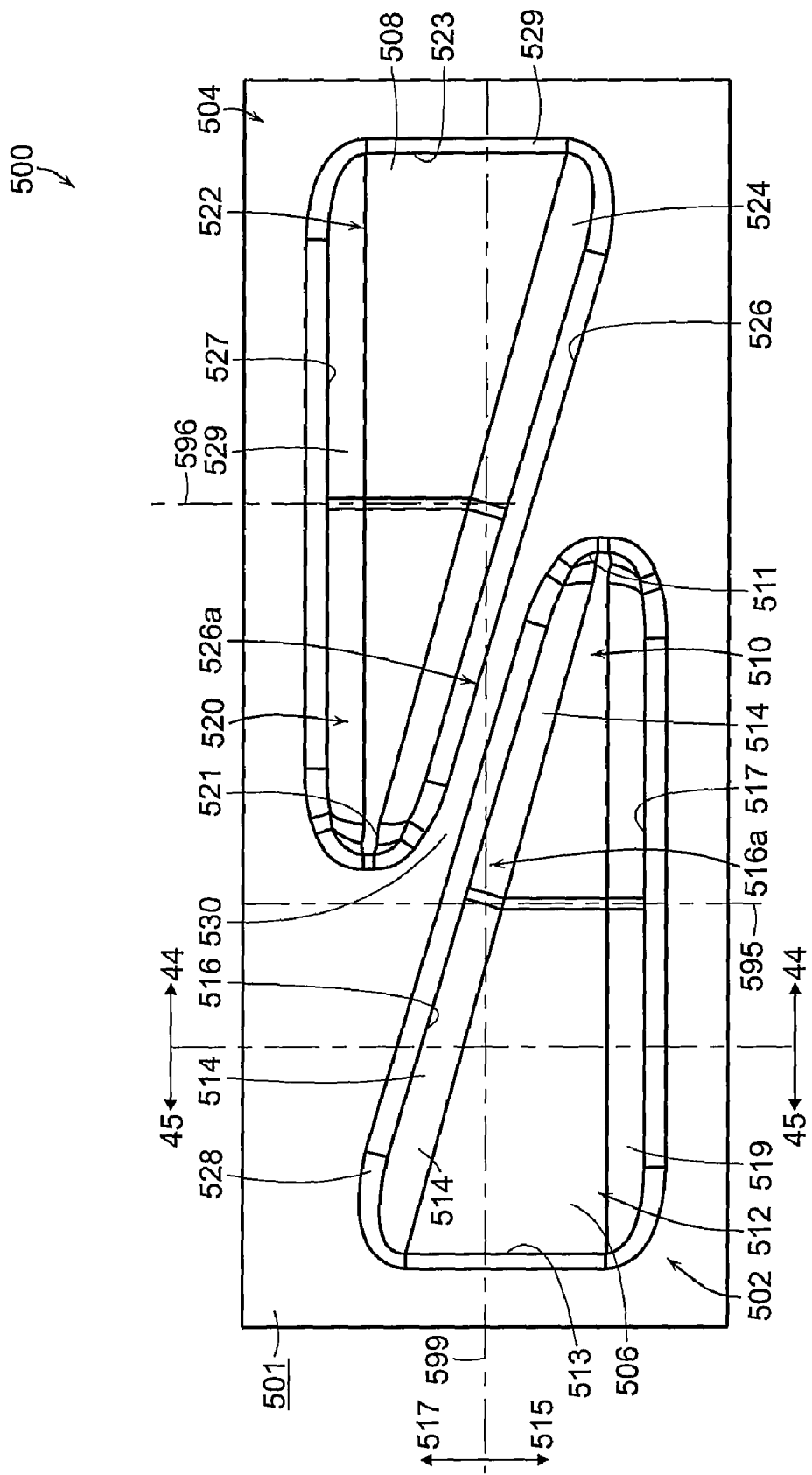
FIG. 43 is a top view of the staple pocket of FIG. 42.

As illustrated in FIG. 43, further to the above, the first interior sidewall 516 can be oriented at an angle with respect to staple pocket longitudinal axis 599. In certain embodiments, the first interior sidewall 516 can be oriented at an acute angle, such as 10 degrees, for example, with respect to longitudinal axis 599. In various embodiments, the first interior sidewall 516 and the longitudinal axis 599 may be neither perpendicular nor parallel to one another. In any event, the first interior sidewall 516 can extend through the axis 599 such that a first portion of the first interior sidewall 516 is positioned on a first side 515 of axis 599 and a second portion of the first interior sidewall 516 is positioned on a second side 517 of axis 599. In various embodiments, as a result, the first interior sidewall 516 can extend between the first outside portion 512 and the first inside portion 510. When the end 405 of first leg 404 contacts the first interior sidewall 516, as described above, the end 405 can be directed along the first interior sidewall 516 and away from longitudinal axis 599 such that the staple leg 404 is bent away from the common plane of staple 400 toward the first side 515 of axis 599. As the end 405 of first leg 404 is directed along, or bent by, the first interior sidewall 516, as described above, the staple leg 404 can also be directed, or bent, by base 506. Stated another way, the first sidewall 516 and the first base 506 can co-operate to deform the first staple leg 404 such that end 405 is re-directed toward the base 402 and, at the same time, to a first side of the base 402 as described above. At some point during the insertion of first staple leg 404 into first forming cup 502, the end 405 of first staple leg 404 can emerge from the first inside portion 510 of first forming cup 502 and, as the staple leg 404 is further deformed by the staple pocket 500, the end 405 can be directed along the first axis 414 (FIG. 50) as described above.

In various embodiments, further to the above, the first interior sidewall 516 can extend along an interior side of the first base 506, wherein, in at least one embodiment, the first forming cup 502 can further comprise a first exterior sidewall 517 extending along an opposite side of the first base 506. In certain embodiments, similar to the above, the first forming cup 502 can further comprise a transition radius 519 positioned intermediate the base 506 and the exterior sidewall

517. In at least one embodiment, referring now to FIG. 43, the exterior sidewall 517 can extend in a direction which is parallel, or at least substantially parallel, to the staple pocket longitudinal axis 599. As also illustrated in FIG. 43, the first interior sidewall 516 and the first exterior sidewall 517 can extend in directions which are transverse to one another. In at least one embodiment, the interior sidewall 516 can extend at an acute angle, such as approximately 15 degrees, for example, with respect to the exterior sidewall 517. In various embodiments, as a result, the outside portion 512 of first forming cup 502 can be wider than the inside portion 510. In at least one such embodiment, the width of the outside portion 512 and the inside portion 510 can taper between a first width and a second width.

In various embodiments, referring once again to FIG. 43, the outside portion 512 of first forming cup 502 can comprise a first outside wall 513 which can extend in a direction which is perpendicular to the first exterior wall 517 and/or the longitudinal axis 599 and can define the outermost portion of forming cup 502. In at least one embodiment, further to the above, the width of the first outside wall 513 can be such that the outside portion 512 can capture the end 405 of first leg 404 and guide it into the inside portion 510 of cup 502 as described above. In at least one such embodiment, the first outside wall 513 can be at least as twice as wide as the diameter of the first leg 404. In certain embodiments, the first forming cup 502 can further comprise a channeling surface 528 surrounding the first inner portion 510 and the first outer portion 512 which can be configured to guide the staple leg 404 into and/or out of the forming cup 502. In various embodiments, the inside portion 510 can further comprise an inside wall 511 which can define the innermost portion of forming cup 502. Similar to the above, the inside wall 511 can also define the narrowest portion of forming cup 502. In at least one embodiment, the width of the inside wall 511 may be the same, or at least substantially the same, as the diameter of first leg 404 such that the inside wall 511 can control the location in which the end 405 emerges from staple forming cup 502.

In various embodiments, further to the above, the second forming cup 504 can comprise an inside portion 520 and an outside portion 522, wherein, when the end 407 of second staple leg 406 enters into the second forming cup 504, the end 407 can enter into the outside portion 522. Upon entering into the outside portion 522 of forming cup 504, the end 407 can contact base 508 and, owing to a concave curve of base 508, the end 407 can be directed inwardly toward the inside portion 520. More particularly, similar to the above, the base 508 can be curved toward tissue-contacting surface 501 such that, as the staple leg 406 contacts the base 508, the end 407 can be directed downwardly, i.e., away from tissue-contacting surface 501, and inwardly along the curved concave surface toward an inflection point 596. In various embodiments, the inflection point 596 can represent the point in which the concave surface of base 508 will begin to deflect the end 407 of second leg 406 upwardly toward the tissue-contacting surface 501. In various embodiments, the radius of curvature, r, of the concave surface can be constant, or at least substantially constant, in the longitudinal direction along the length thereof, similar to the base 506 of first forming cup 502 illustrated in FIGS. 47 and 48. In any event, as the end 407 of second leg 406 is advanced into the inside portion 520 of forming cup 504, the end 407 can come into contact with a radius transition 524 positioned intermediate the base 508 and a second interior sidewall 526. In such embodiments, the radius transition 524 can be configured to direct the end 407 against the second interior sidewall 526.

As illustrated in FIG. 43, further to the above, the second interior sidewall 526 can be oriented at an angle with respect to staple pocket longitudinal axis 599. In certain embodiments, the second interior sidewall 526 can be oriented at an acute angle, such as 10 degrees, for example, with respect to longitudinal axis 599. In various embodiments, the second interior sidewall 526 and the longitudinal axis 599 may be neither perpendicular nor parallel to one another. In any event, the second interior sidewall 526 can extend through the axis 599 such that a first portion of the second interior sidewall 526 is positioned on a first side 515 of axis 599 and a second portion of the second interior sidewall 526 is positioned on a second side 517 of axis 599. In various embodiments, as a result, the second interior sidewall 526 can extend between the second outside portion 522 and the second inside portion 520. When the end 407 of second leg 406 contacts the interior sidewall 526, as described above, the end 407 can be directed along the interior sidewall 526 such that the staple leg 406 is bent away from the common plane of staple 400 toward the second side 517 of axis 599. As the end 407 of second leg 406 is directed along, and bent by, the interior sidewall 526, as described above, the staple leg 406 can also be directed, and bent, by base 508. Stated another way, the second interior sidewall 526 and the second base 508 can co-operate to deform the second staple leg 406 such that end 407 is re-directed toward the base 402 and, at the same time, toward a second, or opposite, side of the base 402 as described above. At some point during the insertion of second staple leg 406 into second forming cup 504, the end 407 of second staple leg 406 can emerge from the second inside portion 520 of second forming cup 504 and, as the staple leg 406 is further deformed by the staple pocket 500, the end 407 can be directed along the second axis 416 (FIG. 50) as described above.

In various embodiments, further to the above, the second interior sidewall 526 can extend along an interior side of the second base 508, wherein, in at least one embodiment, the second forming cup 504 can further comprise a second exterior sidewall 527 extending along an opposite side of the second base 508. In certain embodiments, similar to the above, the second forming cup 504 can further comprise a transition radius 529 positioned intermediate the base 508 and the exterior sidewall 527. In at least one embodiment, referring now to FIG. 43, the exterior sidewall 527 can extend in a direction which is parallel, or at least substantially parallel, to the staple pocket longitudinal axis 599. As also illustrated in FIG. 43, the second interior sidewall 526 and the second exterior sidewall 527 can extend in directions which are transverse to one another. In at least one embodiment, the interior sidewall 526 can extend at an acute angle, such as approximately 15 degrees, for example, with respect to the exterior sidewall 527. In various embodiments, as a result, the outside portion 522 of second forming cup 504 can be wider than the inside portion 520. In at least one such embodiment, the width of the outside portion 522 and the inside portion 520 can taper between a first width and a second width.

In various embodiments, referring once again to FIG. 43, the outside portion 522 of second forming cup 504 can comprise a second outside wall 523 which can extend in a direction which is perpendicular to the second exterior wall 527 and/or the longitudinal axis 599 and can define the outermost portion of forming cup 504. In at least one embodiment, further to the above, the width of the second outside wall 523 can be such that the outside portion 522 can capture the end 407 of second leg 406 and guide it into the inside portion 520 of cup 504 as described above. In at least one such embodiment, the second outside wall 523 can be at least as twice as wide as the diameter of the second leg 406. In certain embodiments, the second forming cup 504 can further comprise a channeling surface 529 surrounding the second inner portion 520 and the second outer portion 522 which can be configured to guide the staple leg 406 into and/or out of the forming cup 504. In various embodiments, the inside portion 520 can further comprise an inside wall 521 which can define the innermost portion of forming cup 504. Similar to the above, the inside wall 521 can also define the narrowest portion of forming cup 504. In at least one embodiment, the width of the inside wall 521 may be the same, or at least substantially the same, as the diameter of second leg 406 such that the inside wall 521 can control the location in which the end 407 emerges from staple forming cup 504.

Figure 44:
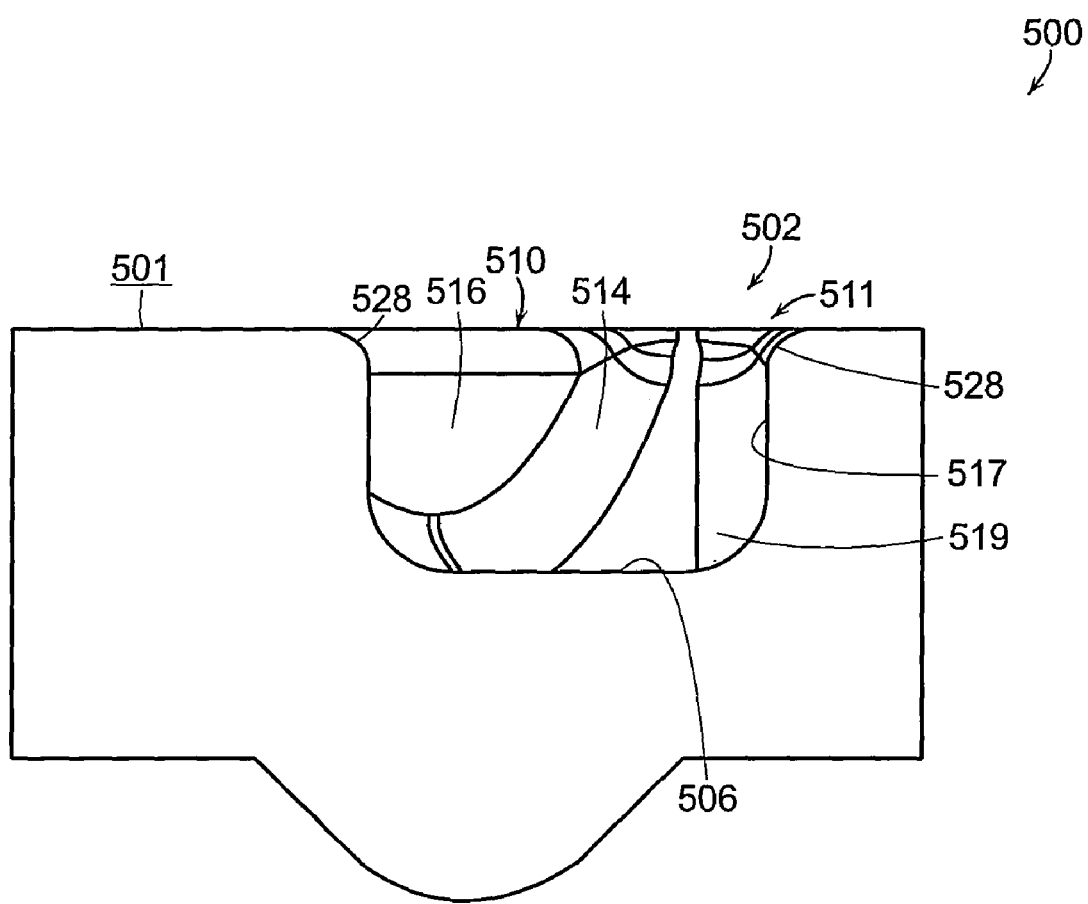
FIG. 44 is a cross-sectional view of the staple pocket of FIG. 42 taken along line 44-44 in FIG. 43.
Figure 45:
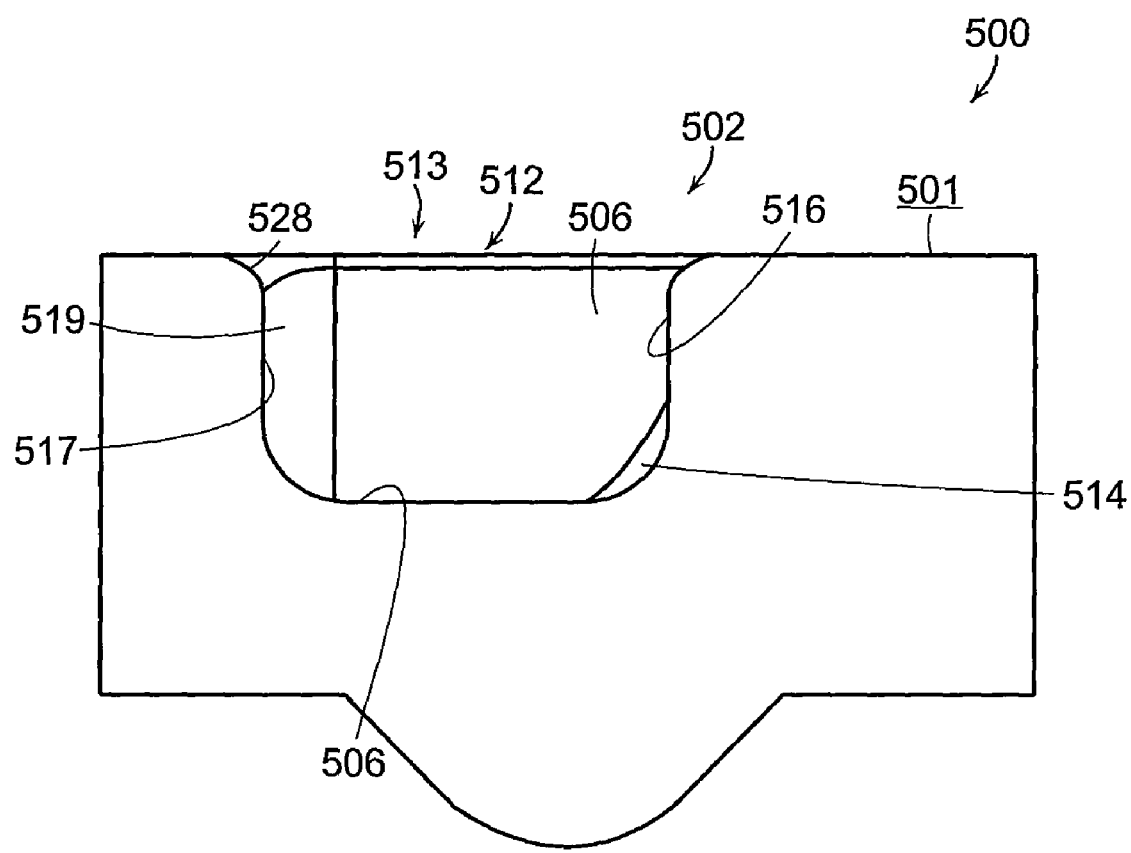
FIG. 45 is a cross-sectional view of the staple pocket of FIG. 42 taken along line 45-45 in FIG. 43.

As discussed above, referring again to FIGS. 43-45, the first forming cup 502 can comprise a first interior sidewall 516 and the second forming cup 504 can comprise a second interior sidewall 526. As illustrated in FIG. 43, the first inside portion 510 of forming cup 502 can be positioned in close proximity to, or close relation to, the second inside portion 520 of forming cup 504 such that the first interior sidewall 516 can be positioned adjacent to the second interior sidewall 526. In at least one embodiment, the first interior portion 510, or at least a substantial portion thereof, can be offset from the staple pocket longitudinal axis 599 in the first direction 515 while the second interior portion 520, or at least a substantial portion thereof, can be offset from the longitudinal axis 599 in the second direction 517. In various embodiments, the staple pocket 500 can comprise a wall 530 positioned intermediate the first inside portion 510 and the second inside portion 520, wherein a first side of wall 530 can comprise the first interior sidewall 516 and wherein a second side of wall 530 can comprise the second interior sidewall 526. In at least one such embodiment, the first interior sidewall 516 can be parallel, or at least substantially parallel to, the second interior sidewall 526. More particularly, in at least one embodiment, the first interior sidewall 516 can define a first plane and the second interior sidewall 526 can define a second plane, wherein the first plane and the second plane can be parallel, or at least substantially parallel, to one another. In various embodiments, referring again to FIGS. 44 and 45, the first interior sidewall 516 can be perpendicular, or at least substantially perpendicular, to the tissue-contacting surface 501 and, similarly, the second interior sidewall 526 can be perpendicular, or at least substantially perpendicular, to the tissue-contacting surface 501.

In various embodiments, further to the above, the first interior sidewall 516 can comprise a first vertical portion 516a which is perpendicular, or at least substantially perpendicular, to the tissue-contacting surface 501. In at least one embodiment, the first vertical portion 516a can extend through, or transect, the longitudinal axis 599. In various embodiments, the first vertical portion 516a can extend along the entirety of, or only a portion of, the first interior sidewall 516. Similarly, the second interior sidewall 526 can comprise a second vertical portion 526a which is perpendicular, or at least substantially perpendicular, to the tissue-contacting surface 501. In at least one embodiment, such a second vertical portion 526a can extend through, or transect, the longitudinal axis 599. In various embodiments, the second vertical portion 526a can extend along the entirety of, or only a portion of, the second interior sidewall 526. During the deployment of staple 400, further to the above, the end 405 of first leg 404 can be in contact with the first vertical portion 516a of first interior sidewall 516 at the same time the end 407 of second leg 406 is in contact with the second vertical portion 526a of second interior sidewall 526. In such circumstances, the first vertical portion 516a and the second vertical portion 526a can comprise a vertical trap. More particularly, the vertical portions 516a and 526a can co-operate to control, deflect, and bend the staple legs 404 and 406 in opposite directions, i.e., in directions to the sides of a common plane, as described above, when the legs 404 and 406 come into contact with the interior sidewalls 516 and 526 of forming cups 502 and 504, respectively. For example, referring again to FIG. 52, the first vertical portion 516a can be configured to deflect and bend the staple leg 404 to a first side of base 402 and the second vertical portion 526a can be configured to deflect and bend the staple leg 406 to a second, or opposite, side of base 402.

In various embodiments, further to the above, the vertical trap comprising vertical portions 516a and 526a can extend along the entire length of the first and second interior sidewalls 516 and 526, while, in other embodiments, the vertical trap may extend along only a portion of the sidewalls 516 and 526. In at least one embodiment, the vertical trap can be approximately 0.05 inches long, i.e., the overlap of the first vertical surface 516a and the second vertical surface 526a can be approximately 0.05 inches, for example, along the lengths of interior surfaces 516 and 526. In various embodiments, the length of the vertical trap can be between approximately 0.03 inches and approximately 0.10 inches, for example. In certain embodiments, the length of the vertical trap can be approximately twice the radius of curvature (r) of the curved concave surface of base 506, for example. In various embodiments, the length of the vertical trap can be approximately equal to the radius of curvature (r) of base 506, for example. In at least one embodiment, the length of the vertical trap can be between approximately 0.5*r and approximately 2*r, for example. In various embodiments, further to the above, the vertical trap can extend through the longitudinal axis 599 of staple pocket 500 such that, in at least one embodiment, at least a portion of the vertical trap can be positioned on a first side and/or a second side of axis 599. In certain embodiments, the vertical trap can extend through the central portions of the first and second forming cups 502 and 504.

In various embodiments, the first interior sidewall 516 can further comprise a first angled portion which, in at least one embodiment, can be oriented at an acute angle with respect to the tissue-contacting surface 501. In at least one such embodiment, the first angled portion can be positioned outwardly with respect to the first vertical portion 516a. In certain embodiments, the first interior sidewall 516 can comprise an angled portion positioned toward the outside portion 512 which can become progressively more perpendicular toward the inside portion 510 of the first forming cup 502 until the angled portion transitions into the first vertical portion 516a. In various embodiments, the second interior sidewall 526 can further comprise a second angled portion which, in at least one embodiment, can be oriented at an acute angle with respect to the tissue-contacting surface 501. In at least one such embodiment, the second angled portion can be positioned outwardly with respect to the second vertical portion 526a. In certain embodiments, the second interior sidewall 526 can comprise an angled portion positioned toward the outside portion 522 which can become progressively more perpendicular toward the inside portion 520 of the second forming cup 504 until the angled portion transitions into the second vertical portion 526a.

Figure 52A:
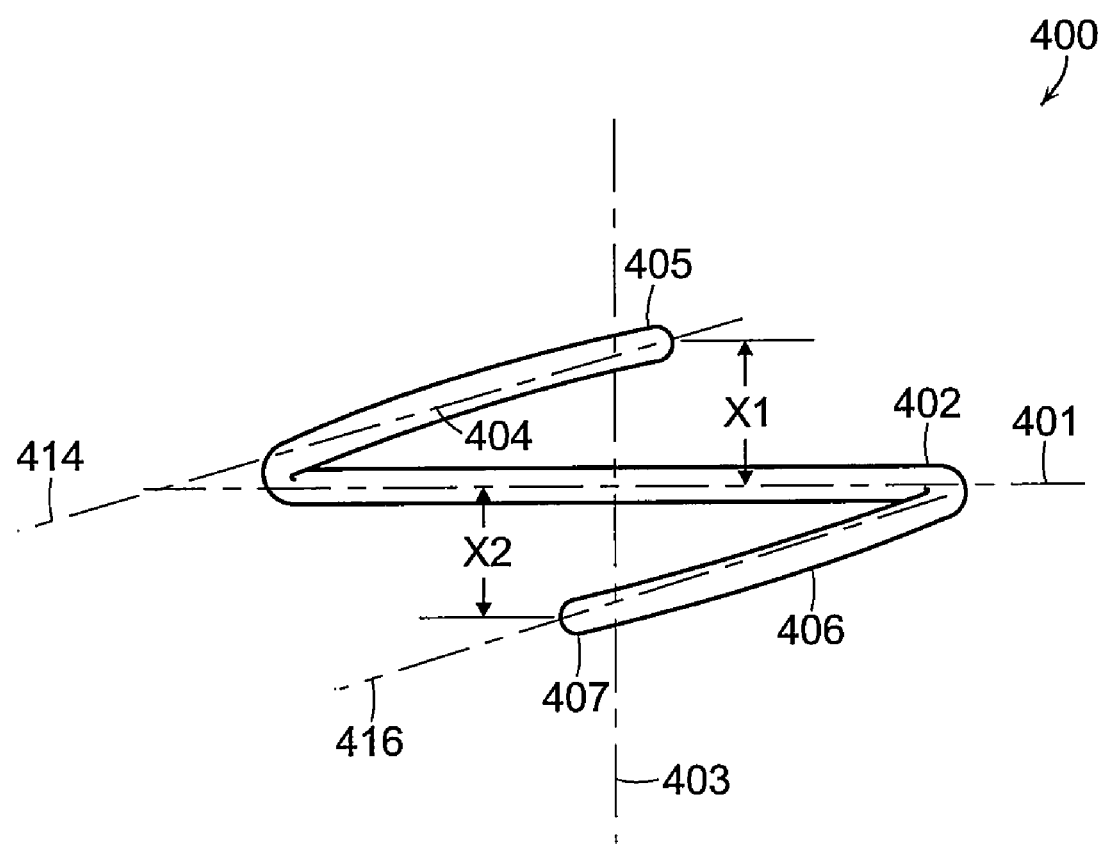
FIG. 52A is another plan view of the surgical staple of FIG. 49 in the deformed shape of FIG. 50.
Figure 54:
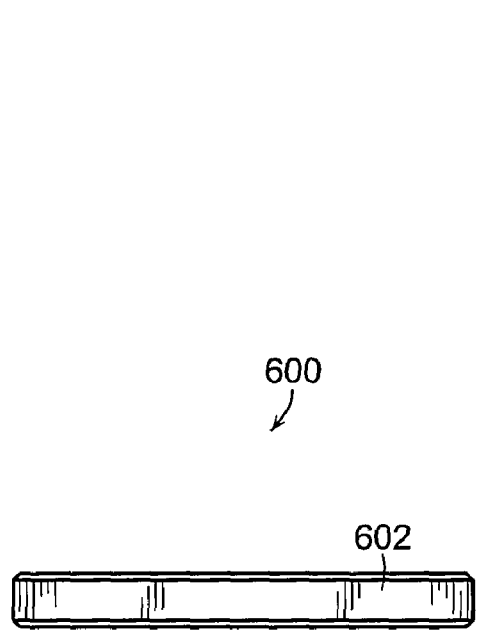
FIG. 54 is a bottom view of the surgical staple of FIG. 53 in an undeformed shape.
Figure 53:
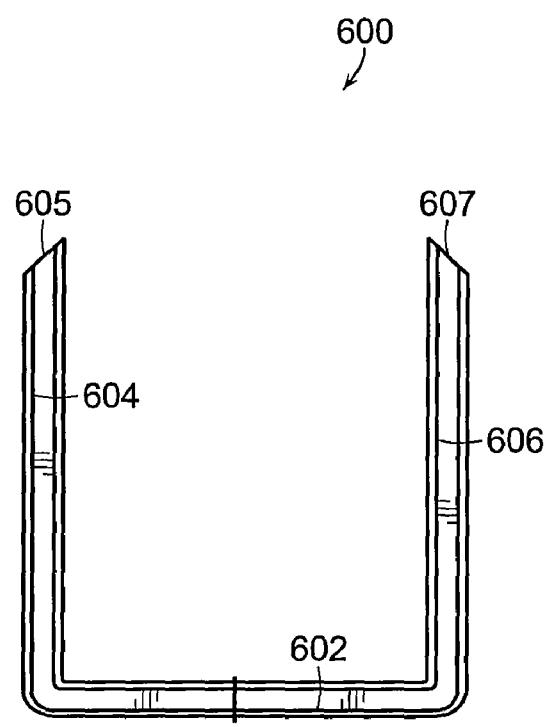
FIG. 53 is an elevational view of a surgical staple in an undeformed shape.

In various embodiments, referring now to FIG. 52A, the staple pocket 500 can be configured to deform the first staple leg 404 such that the first end 405 is deflected a first distance X1 from baseline 401. Similarly, the second staple leg 406 can be deformed such that the second end 407 is deflected a second distance X2 from baseline 401. In certain embodiments, the distance X1 and the distance X2 can be the same, or at least substantially the same. In various other embodiments, the distances X1 and X2 can be different. In at least one such embodiment, the first leg 404 can be deformed such that the first end 405 is positioned closer to base 402 than the second end 407, for example. In such embodiments, the first axis 414 of deformed staple leg 404 and the second axis 416 of deformed staple leg 406 may be non-parallel. More particularly, in at least one embodiment, the first axis 414 can extend at a first angle with respect to baseline 401 and the second axis 416 can extend at a second angle with respect to baseline 401 wherein the second angle is different than the first angle. In various embodiments, the first leg 404 and the second leg 406 can extend across midline 403 at different angles. In certain other embodiments, the first leg 404 and the second leg 406 can be extend at different angles with respect to baseline 401 although one or both of the legs 404 and 406 may not extend across the midline 403.

In various embodiments, further to the above, a surgical stapler can comprise a staple pocket which can be configured to deform one staple leg of staple 400 such that it lies within, or substantially within, a common plane with base 402 and, in addition, deform the other staple leg of staple 400 to a side of base 402 as described above. In at least one embodiment, the first leg 404 can be deformed such that it extends through midline 403 in a direction which is co-planar, or at least substantially co-planar, with base 402 and, in addition, the second leg 406 can be deformed such that it extends through midline 403 in a direction which is transverse to the plane. Stated another way, in at least one embodiment, axis 414 and baseline 401 of staple 400 can be coplanar, or at least nearly co-planar, with one another while second axis 416 can extend in a direction which extends through such a plane. In certain embodiments, at least one of the first leg 404 and the second leg 406 may not extend through the midline 403.

In various embodiments, further to the above, the staple pocket 500 can be configured to deform the staple legs 404 and 406 of staple 400 simultaneously, or at least substantially simultaneously. In at least one embodiment, the base 506 of first forming cup 502 can contact end 405 of first staple leg 404 at the same time, or at least substantially the same time, that the base 508 of second forming cup 504 contacts end 407 of second staple leg 406. In certain other embodiments, a staple pocket can be configured to deform the staple legs 404 and 406 sequentially. In at least one such embodiment, a first forming cup can be brought into contact with the first staple leg 404 before a second forming cup is brought into contact with the second staple leg 406, for example. In various alternative embodiments, although not illustrated, a surgical staple can comprise more than two staple legs, such as three staple legs or four staple legs, for example, and a staple pocket can comprise a corresponding quantity of staple forming cups for deforming the staple legs.

In various embodiments, further to the above, the wire comprising the surgical staple 400 can comprise a circular, or at least substantially circular, cross-section. In various other embodiments, referring now to FIGS. 53-56, a surgical staple, such as staple 600, for example, can comprise a non-circular cross-section. In at least one embodiment, the staple 600 can comprise a base 602, a first leg 604, and a second leg 606, wherein the base 602 and legs 604 and 606 can be comprised of a continuous wire. In various embodiments, the continuous wire can comprise a rectangular cross-section, for example. In at least one embodiment, referring to FIG. 56, the rectangular cross-section can comprise a base (b) and a height (h), wherein the base (b) can be defined relative to a central lateral axis (x), and wherein the height (h) can be defined relative to a central longitudinal axis (y). In various circumstances, the rectangular cross-section can be defined as having two moments of inertia, i.e., a first moment of inertia (Ix) defined with respect to axis (x) and a second moment of inertia (Iy) defined with respect to axis (y). In at least one circumstance, the first moment of inertia (Ix) can be calculated as $(b*h^3)/12$ while the second moment of inertia (Iy) can be calculated as $(h*b^3)/12$. Although staple 600 comprises a rectangular, or at least substantially rectangular cross-section, any other suitable non-circular cross-section can be utilized, such as oblate, elliptical, and/or trapezoidal cross-sections, for example.

Figure 55:
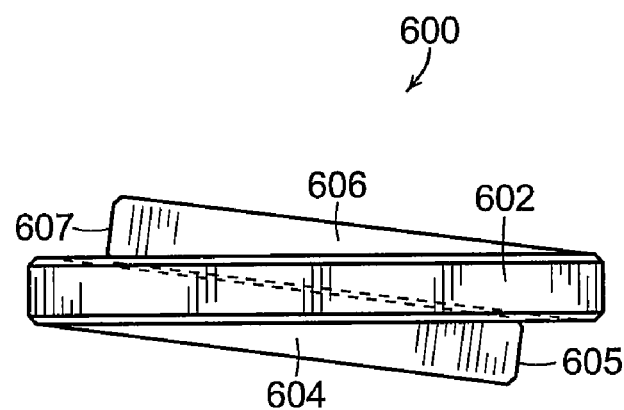
FIG. 55 is a bottom view of the surgical staple of FIG. 53 in a deformed shape in accordance with at least one embodiment of the present invention.
Figure 56:
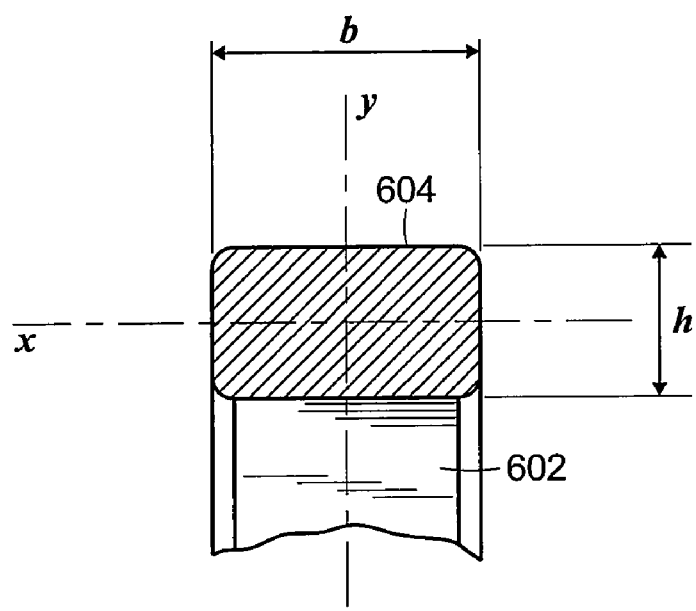
FIG. 56 is a partial cross-sectional view of the surgical staple of FIG. 53.

As illustrated in FIG. 56, the base (b) of surgical staple 600 is larger than the height (h) and, in view of the above, the moment of inertia (Iy) of the rectangular cross-section is larger than the moment of inertia (Ix). In various embodiments, as a result, the moment of inertia ratio, i.e., Iy/Ix, of the rectangular cross-section can be greater than 1.0. In certain embodiments, the moment of inertia ratio can be between approximately 2.0 and approximately 2.7, for example. In certain other embodiments, the moment of inertia ratio can be between approximately 1.1 and approximately 3.0, for example. As a result of the above, the leg 604 is more likely to bend about axis (x) than about axis (y) when a force, such as compressive load F1, for example, is applied to the leg 604. In any event, absent all other considerations, the leg 604, in such embodiments, is more likely to bend within a common plane defined by the staple 600 when it is in its undeformed state than bend to a side of staple base 602. In various embodiments, however, a surgical stapler comprising an anvil and staple pocket in accordance with the embodiments described herein, such as staple pocket 500, for example, can be utilized to cause the legs 604 and 606 of staple 600 to bend out of their common plane when they are deformed. In such embodiments, this lateral deflection can occur despite the fact that the moment of inertia Iy, which resists such twisting, is greater than the moment of inertia 1x. As illustrated in FIG. 55, the first leg 604 of staple 600 can be deformed such that it is bent relative to both axis (x) and axis (y) of its cross-section and, as a result, the first staple leg 604 can be twisted or deformed such that the end 605 of first staple leg 604 is positioned on a first side of base 602. Similarly, the second leg 606 can be deformed such that it is bent relative to both axis (x) and axis (y) of its cross-section and, as a result, the second staple leg 606 can be twisted or deformed such that the end 607 of second staple leg 606 is positioned on a second side of base 602.

Figure 57:
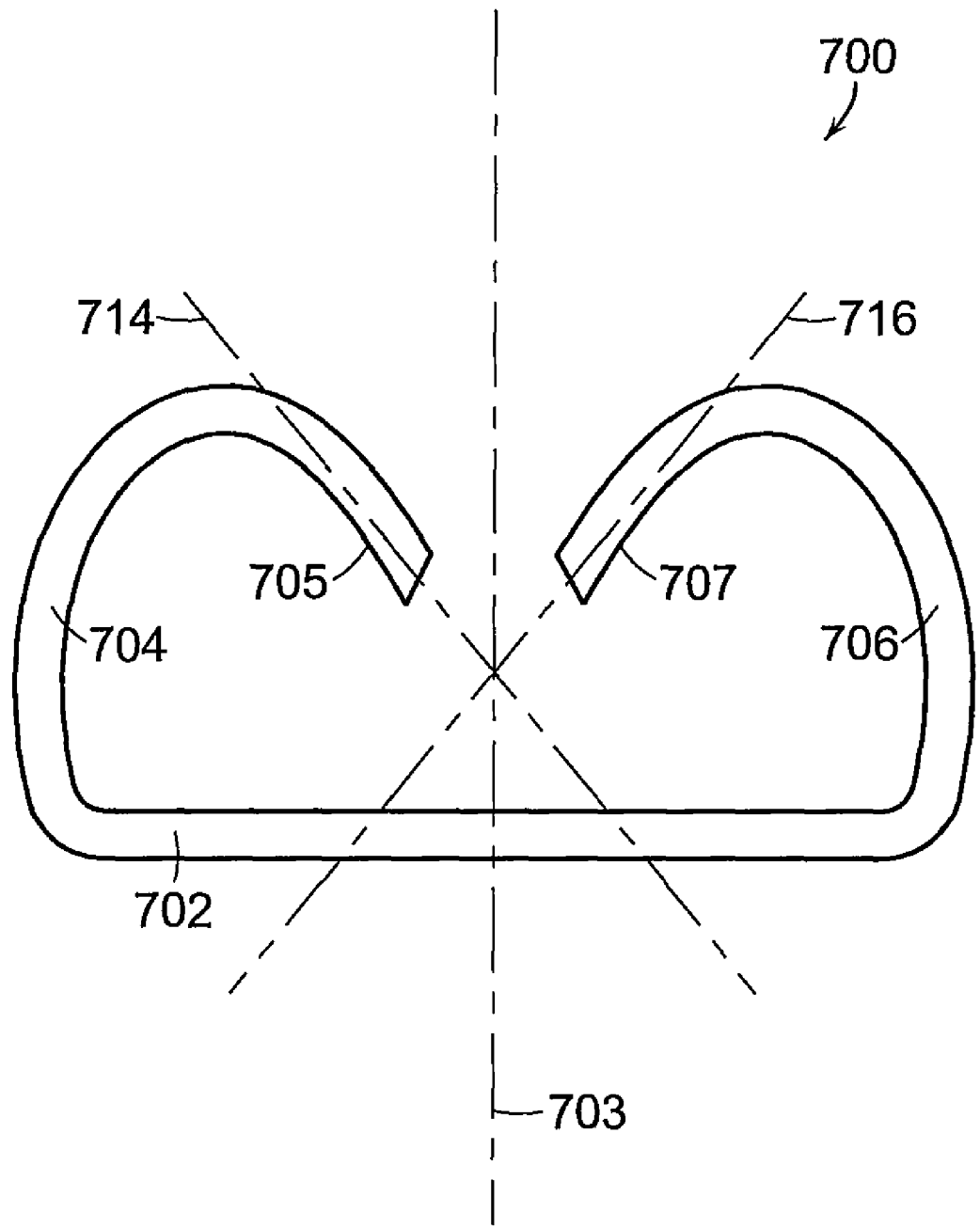
FIG. 57 is an elevational view of a surgical staple in a deformed shape in accordance with at least one embodiment of the present invention.

In various embodiments, referring now to FIG. 57, a surgical staple, such as surgical staple 700, for example, can comprise a base 702 and, in addition, a first leg 704 and a second leg 706 extending from base 702. In certain embodiments, similar to the above, the base 702, the first leg 704, and the second leg 706 can lie, or at least substantially lie, in a common plane when the staple 700 is an undeformed, or undeployed, configuration, i.e., a configuration prior to being deformed by an anvil of a surgical stapler, for example. In the deformed or deployed configuration of staple 700, as illustrated in FIG. 57, the first leg 704 can be deformed such that end 705 points toward base 702 and second leg 706. More particularly, in at least one embodiment, the end 705 can lie along, or with respect to, a first axis 714 which is oriented at angle with respect to midline 703. Similarly, the second leg 706 can be deformed such that end 707 points toward base 702 and first leg 704. More particularly, in at least one embodiment, the end 707 can lie along, or with respect to, a second axis 716 which is oriented at angle with respect to midline 703. In various embodiments, the ends 705 and 707 of legs 704 and 706 may not cross mid-line 703. In certain embodiments, similar to the above, the end 705 of first leg 704 may be deformed such that it extends to a first side of base 702 and the end 707 of second leg 706 may be deformed such that it extends to a second, or opposite, side of base 702 such that legs 704 and 706 are not entirely positioned in-plane with base 702 in their deformed configuration, for example.

Figure 58:
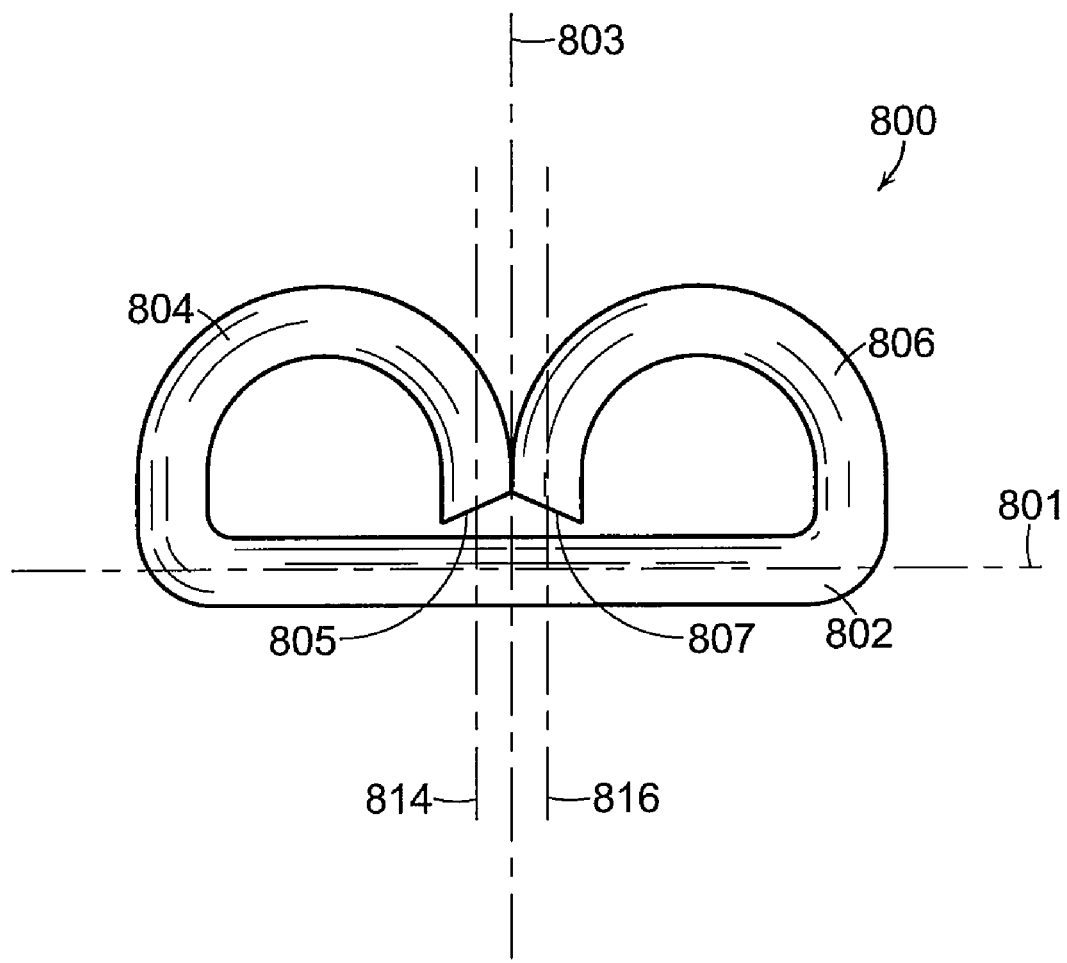
FIG. 58 is an elevational view of a surgical staple in a deformed shape.

In various embodiments, a surgical staple, such as staple 800 (FIG. 58), for example, can comprise a base 802, a first leg 804, and a second leg 806, wherein the staple 800 can comprise a substantially U-shaped configuration in its undeformed, or undeployed, configuration. In at least one such embodiment, legs 804 and 806 can extend in a perpendicular, or at least substantially perpendicular, direction with respect to base 802. In various circumstances, the staple 800 can be deformed into a B-shaped configuration as illustrated in FIG. 58. In at least one such embodiment, the first leg 804 can be bent downwardly toward base 802 such that axis 814 extending through end 805 is perpendicular, or at least substantially perpendicular, to baseline 801. Similarly, the second leg 806 can be bent downwardly toward base 802 such that axis 816 extending through end 807 is perpendicular, or at least substantially perpendicular, to baseline 801. In at least one such circumstance, the legs 804 and 806 can be bent such that axes 814 and 816 are parallel, or at least substantially parallel, to one another. In various embodiments, referring again to FIG. 58, the staple legs 804 and 806 can be deformed such that they do not cross centerline 803. The staple legs 804 and 806 can be deformed such that they remain in-plane, or at least substantially in-plane, with base 802.

Various examples described below are envisioned which incorporate one or more aspects of the various embodiments described above. Such examples are exemplary and various aspects of various embodiments described in this application can be combined in a single embodiment. In each of the examples described below, the surgical staple can comprise a base defining a baseline, a first leg and a second leg which extend from the base, and a midline midway between the first leg and the second leg.

EXAMPLE 1

A surgical staple can be deformed such that:

| First Leg | Second Leg |
|---|---|
| Crosses the midline (FIG. 50) | Crosses the midline (FIG. 50) |
| Extends in-plane, or substantially in-plane, with the base (FIG. 58) | Extends out of plane with the base (FIG. 52) |
| The end extends in a non-perpendicular direction with the baseline (FIG. 50) | The end extends in a non-perpendicular direction with the baseline (FIG. 50) |

EXAMPLE 2

A surgical staple can be deformed such that:

| First Leg | Second Leg |
|---|---|
| Crosses the midline (FIG. 50) | Crosses the midline (FIG. 50) |
| Extends out of plane with the base (FIG. 52) to the same side of the base as the second leg, the distance X1 being different than X2 (FIG. 52A) | Extends out of plane with the base (FIG. 52) to the same side of the base as the first leg, the distance X1 being different than X2 (FIG. 52A) |
| The end extends in a non-perpendicular direction with the baseline (FIG. 50) | The end extends in a non-perpendicular direction with the baseline (FIG. 50) |

EXAMPLE 3

A surgical staple can be deformed such that:

| First Leg | Second Leg |
|---|---|
| Does not cross the midline (FIG. 57) | Does not cross the midline (FIG. 57) |
| Extends out of plane with the base (FIG. 52) to a first side of the base, the distance X1 being different than X2 (FIG. 52A) | Extends out of plane with the base (FIG. 52) to a second side of the base, the distance X1 being different than X2 (FIG. 52A) |
| The end extends in a non-perpendicular direction with the baseline (FIG. 50) | The end extends in a non-perpendicular direction with the baseline (FIG. 50) |

EXAMPLE 4

A surgical staple can be deformed such that:

| First Leg | Second Leg |
|---|---|
| Does not cross the midline (FIG. 57) | Does not cross the midline (FIG. 57) |
| Extends out of plane with the base (FIG. 52) to the same side of the base as the second leg, the distance X1 being different than X2 (FIG. 52A) | Extends out of plane with the base (FIG. 52) to the same side of the base as the second leg, the distance X1 being different than X2 (FIG. 52A) |
| The end extends in a non-perpendicular direction with the baseline (FIG. 50) | The end extends in a non-perpendicular direction with the baseline (FIG. 50) |

EXAMPLE 5

A surgical staple can be deformed such that:

| First Leg | Second Leg |
|---|---|
| Does not cross the midline (FIG. 57) | Does not cross the midline (FIG. 57) |
| Extends in-plane, or substantially in-plane, with the base (FIG. 58) | Extends out of plane with the base (FIG. 52) |
| The end extends in a perpendicular direction with the baseline (FIG. 58) | The end extends in a non-perpendicular direction with the baseline (FIG. 50) |

EXAMPLE 6

A surgical staple can be deformed such that:

| First Leg | Second Leg |
|---|---|
| Crosses the midline (FIG. 50) | Does not cross the midline (FIG. 57) |
| Extends out of plane with the | Extends out of plane with the |

-continued

| First Leg | Second Leg |
| --- | --- |
| base (FIG. 52) to a first side of the base, the distance X1 being different than X2 (FIG. 52A) The end extends in a non-perpendicular direction with the baseline (FIG. 50) | base (FIG. 52) to a second side of the base, the distance X1 being different than X2 (FIG. 52A) The end extends in a non-perpendicular direction with the baseline (FIG. 50) |

EXAMPLE 7

A surgical staple can be deformed such that:

| First Leg | Second Leg |
| --- | --- |
| Crosses the midline (FIG. 50) Extends out of plane with the base (FIG. 52) to the same side of the base as the second leg, the distance X1 being different than X2 (FIG. 52A) The end extends in a non-perpendicular direction with the baseline (FIG. 50) | Does not cross the midline (FIG. 57) Extends out of plane with the base (FIG. 52) to the same side of the base as the second leg, the distance X1 being different than X2 (FIG. 52A) The end extends in a non-perpendicular direction with the baseline (FIG. 50) |

EXAMPLE 8

A surgical staple can be deformed such that:

| First Leg | Second Leg |
| --- | --- |
| Crosses the midline (FIG. 50) Extends out of plane with the base (FIG. 52) The end extends in a non-perpendicular direction with the baseline (FIG. 50) | Does not cross the midline (FIG. 57) Extends in-plane, or substantially in-plane, with the base (FIG. 58) The end extends in a perpendicular direction to the baseline (FIG. 58) |

EXAMPLE 9

A surgical staple can be deformed such that:

| First Leg | Second Leg |
| --- | --- |
| Crosses the midline (FIG. 50) Extends in-plane, or substantially in-plane, with the base (FIG. 58) The end extends in a non-perpendicular direction with the baseline (FIG. 50) | Does not cross the midline (FIG. 57) Extends out of plane with the base (FIG. 52) The end extends in a non-perpendicular direction with the baseline (FIG. 50) |

Several of the deformed staples described above comprise one or more staple legs which cross the mid-line of the staple base. In various embodiments, as a result, the deformed staple legs may at least partially overlap with one another. More particularly, the deformed staple legs, when viewed from the side, may co-operate to traverse the staple base from one end to the other leaving no gap therebetween. Such embodiments can be particularly useful, especially when used to staple vascular tissue. More specifically, the overlapping staple legs can compress blood vessels within the tissue regardless of where the blood vessels extend through the staple. Staples having gaps between the legs, or legs which do not extend along the entire length of the staple base when deformed, may not be able to properly compress every blood vessel in the tissue and, as a result, one or more blood vessels may leak.

In various embodiments, further to the above, a surgical instrument can be configured to deploy a plurality of staples 400 in the manner described above and illustrated in FIGS. 50-52. In at least one such embodiment, the surgical stapler can deploy the staples 400 in a sequential manner along a staple path and/or in a simultaneous manner, for example. In certain embodiments, a surgical instrument can be configured to deploy a plurality of staples 600 in the manner described above and illustrated in FIG. 55. In at least one such embodiment, similar to the above, the surgical stapler can deploy the staples 600 in a sequential manner along a staple path and/or in a simultaneous manner, for example. In various embodiments, further to the above, a surgical instrument can be configured to deploy a plurality of staples 700 in the manner described above and illustrated in FIG. 57. In at least one such embodiment, the surgical stapler can deploy the staples 700 in a sequential manner along a staple path and/or in a simultaneous manner, for example.

In various embodiments, further to the above, a surgical staple can be comprised of titanium, such as titanium wire, for example. In certain embodiments, a surgical staple can be comprised of an alloy comprising titanium, aluminum, and/or vanadium, for example. In at least one embodiment, the surgical staple can be comprised of surgical stainless steel and/or an alloy comprised of cobalt and chromium, for example. In any event, the surgical staple can be comprised of metal, such as titanium, and a metal oxide outer surface, such as titanium oxide, for example. In various embodiments, the metal oxide outer surface can be coated with a material. In certain embodiments, the coating material can be comprised of polytetrafluoroethylene (PTFE), such as Teflon®, and/or a tetrafluoroethylene (TFE) such as ethylene-tetrafluoroethylene (ETFE), perfluoroalkoxyethylene-tetrafluoroethylene (PFA), and/or Fluorinated Ethylene Propylene (FEP), for example. Certain coatings can comprise silicon. In various embodiments, such coating materials can prevent, or at least inhibit, further oxidation of the metal. In certain embodiments, the coating materials can provide one or more lubricious surfaces against which the anvil, or staple pockets, can contact the staples in order to reduce the friction force therebetween. In various circumstances, lower friction forces between the staples and the staple pockets can reduce the force required to deform the staples.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A surgical stapler, comprising:
a first handle portion comprising:
    a staple cartridge channel configured to receive a staple cartridge; and
    a latch rotatably coupled to said staple cartridge channel;
a second handle portion comprising:
    a frame;
    an anvil; and
    a latch projection, wherein said first handle portion further comprises a recess configured to receive said latch projection, wherein said latch is configured to engage said latch projection and position said latch projection within said recess to move said first handle portion and said second handle portion toward one another, and wherein said latch projection comprises:
        a shaft portion extending from said frame;
        an enlarged portion extending from said shaft portion; and
        a rotatable bearing comprising a bearing aperture, wherein said shaft portion extends through said bearing aperture, wherein said rotatable bearing is rotatable about said shaft portion, wherein said rotatable bearing is positioned intermediate said frame and said enlarged portion, and wherein said latch is configured to contact said rotatable bearing when said latch engages said latch projection; and
wherein said latch comprises a latch projection slot configured to receive said latch projection, wherein said latch projection slot comprises a first sidewall and a second sidewall, wherein said first sidewall is positioned opposite said second sidewall, wherein said first sidewall is configured to apply a closing force to said bearing in order to move said first handle portion and said second handle portion toward one another, and wherein said second sidewall is configured to apply an opening force to said bearing in order to move said first handle portion and said second handle portion away from one another.

2. The surgical stapler of claim 1, wherein said bearing comprises an outer diameter, wherein said first sidewall and said second sidewall define a slot width therebetween, and wherein said outer diameter is slightly smaller than said slot width.

3. A surgical stapler, comprising:
a first handle portion comprising:
    a staple cartridge channel configured to receive a staple cartridge; and
    a latch rotatably coupled to said staple cartridge channel;
a second handle portion comprising:
    a frame;
    an anvil; and
    a latch projection, wherein said first handle portion further comprises a recess configured to receive said latch projection, wherein said latch is configured to engage said latch projection and position said latch projection within said recess to move said first handle portion and said second handle portion toward one another and wherein said latch projection comprises:
        a shaft portion extending from said frame;
        an enlarged portion extending from said shaft portion; and
        a rotatable bearing comprising a bearing aperture, wherein said shaft portion extends through said bearing aperture, wherein said rotatable bearing is rotatable about said shaft portion, wherein said rotatable bearing is positioned intermediate said frame and said enlarged portion, and wherein said latch is configured to contact said rotatable bearing when said latch engages said latch projection; and
wherein said bearing aperture comprises a circular inner profile, wherein said shaft portion comprises a circular outer profile, and wherein said circular outer profile defines an outer diameter which is slightly smaller than an inner diameter defined by said circular inner profile of said bearing aperture.

4. A surgical stapler, comprising:
a first handle portion comprising:
    a staple cartridge channel configured to receive a staple cartridge; and
    a latch rotatably coupled to said staple cartridge channel;
a second handle portion comprising:
    a frame;
    an anvil; and
    a latch projection, wherein said first handle portion further comprises a recess configured to receive said latch projection, wherein said latch is configured to engage said latch projection and position said latch projection within said recess to move said first handle portion and said second handle portion toward one another, and wherein said latch projection comprises:
        a shaft portion extending from said frame;
        an enlarged portion extending from said shaft portion; and
        a rotatable bearing comprising a bearing aperture, wherein said shaft portion extends through said bearing aperture, wherein said rotatable bearing is rotatable about said shaft portion, wherein said rotatable bearing is positioned intermediate said frame and said enlarged portion, and wherein said latch is configured to contact said rotatable bearing when said latch engages said latch projection; and
wherein said bearing aperture is defined by an aperture diameter, and wherein said enlarged portion is defined by a diameter which is larger than said aperture diameter.

5. A surgical stapler, comprising:
a first handle portion comprising a staple cartridge channel configured to receive a staple cartridge;
a second handle portion comprising an anvil;
a rotatable latch;
a latch projection, wherein said latch is rotatably coupled to one of said first handle portion and said second handle portion and wherein said latch projection extends from the other of said first handle portion and said second handle portion, wherein said latch is configured to engage said latch projection to move said first handle portion and said second handle portion toward one another, wherein said latch projection comprises a rotatable bearing, and wherein said latch is configured to contact said rotatable bearing when said latch engages said latch projection; and wherein said projection further comprises a shaft portion and an enlarged portion extending from said shaft portion, wherein said bearing comprises a bearing aperture, wherein said shaft portion extends through said bearing aperture, wherein said rotatable bearing is rotatable about said shaft portion, and wherein said enlarged portion is configured to retain said rotatable bearing on said shaft portion.

6. The surgical stapler of claim 5, wherein said bearing aperture comprises a circular inner profile, wherein said shaft portion comprises a circular outer profile, and wherein said circular outer profile defines an outer diameter which is slightly smaller than an inner diameter defined by said circular inner profile of said bearing aperture.

7. The surgical stapler of claim 5, wherein said bearing aperture is defined by an aperture diameter, and wherein said enlarged portion is defined by a diameter which is larger than said aperture diameter.

8. A surgical stapler, comprising:
a first handle portion comprising a staple cartridge channel configured to receive a staple cartridge;
a second handle portion comprising an anvil;
a rotatable latch;
a latch projection, wherein said latch is rotatably coupled to one of said first handle portion and said second handle portion and wherein said latch projection extends from the other of said first handle portion and said second handle portion, wherein said latch is configured to engage said latch projection to move said first handle portion and said second handle portion toward one another, wherein said latch projection comprises a rotatable bearing, and wherein said latch is configured to contact said rotatable bearing when said latch engages said latch projection; and
wherein said latch comprises a latch projection slot configured to receive said latch projection, wherein said latch projection slot comprises a first sidewall and a second sidewall, wherein said first sidewall is positioned opposite said second sidewall, wherein said first sidewall is configured to apply a closing force to said bearing in order to move said first handle portion and said second handle portion toward one another, and wherein said second sidewall is configured to apply an opening force to said bearing in order to move said first handle portion and said second handle portion away from one another.

9. The surgical stapler of claim 8, wherein said bearing comprises an outer diameter, wherein said first sidewall and said second sidewall define a slot width therebetween, and wherein said outer diameter is slightly smaller than said slot width.

10. A stapler assembly, comprising:
a first handle portion comprising:
a staple cartridge channel configured to receive a staple cartridge; and
a latch rotatably coupled to said staple cartridge channel;
a second handle portion comprising:
a frame;
an anvil;
a pivot; and
a rotatable bearing having a circular drive surface, wherein said rotatable bearing is rotatably mounted onto said pivot, wherein said latch is configured to capture said rotatable bearing and slide across said circular drive surface of said rotatable bearing to position said first handle portion and said second handle portion in a closed configuration relative to one another, and wherein said rotatable bearing is configured to rotate about said pivot as said latch slides across said circular drive surface.

11. The stapler assembly of claim 10, wherein said latch further comprises a slot configured to receive said rotatable bearing, wherein said slot comprises a first sidewall and a second sidewall, wherein said first sidewall is positioned opposite said second sidewall, wherein said first sidewall is configured to apply a closing force to said rotatable bearing in order to move said first handle portion and said second handle portion toward one another, and wherein said second sidewall is configured to apply an opening force to said rotatable bearing in order to move said first handle portion and said second handle portion away from one another.

12. A stapler assembly, comprising:
a first handle portion comprising a staple cartridge channel configured to receive a staple cartridge;
a second handle portion comprising an anvil;
a rotatable latch;
a pivot; and
a rotatable bearing having a circular drive surface, wherein said latch is rotatably coupled to one of said first handle portion and said second handle portion, wherein the other of said first handle portion and said second handle portion comprises said pivot and said rotatable bearing, wherein said rotatable bearing is rotatably mounted onto said pivot, wherein said latch is configured to catch said rotatable bearing and slide across said circular drive surface to move said first handle portion and said second handle portion toward one another, and wherein said rotatable bearing is configured to rotate about said pivot as said latch slides across said circular drive surface.

13. The stapler assembly of claim 12, wherein said latch further comprises a slot configured to receive said rotatable bearing, wherein said slot comprises a first sidewall and a second sidewall, wherein said first sidewall is positioned opposite said second sidewall, wherein said first sidewall is configured to apply a closing force to said rotatable bearing in order to move said first handle portion and said second handle portion toward one another, and wherein said second sidewall is configured to apply an opening force to said rotatable bearing in order to move said first handle portion and said second handle portion away from one another.

* * * * *